US010902952B2

(12) United States Patent
Lucas et al.

(10) Patent No.: US 10,902,952 B2
(45) Date of Patent: *Jan. 26, 2021

(54) MOBILE SUPPLEMENTATION, EXTRACTION, AND ANALYSIS OF HEALTH RECORDS

(71) Applicant: Tempus Labs, Chicago, IL (US)

(72) Inventors: Michael Ryan Lucas, Chicago, IL (US); Jonathan Ozeran, Chicago, IL (US); Jason L Taylor, Chicago, IL (US); Louis E. Fernandes, Chicago, IL (US); Daniel Neems, Chicago, IL (US); Hunter Lane, Chicago, IL (US); Eric Lefkofsky, Glencoe, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/531,005

(22) Filed: Aug. 2, 2019

(65) Prior Publication Data

US 2020/0126663 A1    Apr. 23, 2020

Related U.S. Application Data

(63) Continuation of application No. 16/289,027, filed on Feb. 28, 2019, now Pat. No. 10,395,772.

(Continued)

(51) Int. Cl.
*G16H 50/20*    (2018.01)
*G16H 30/40*    (2018.01)
(Continued)

(52) U.S. Cl.
CPC ......... *G16H 50/20* (2018.01); *G06K 9/00469* (2013.01); *G06K 9/00483* (2013.01);
(Continued)

(58) Field of Classification Search
CPC ........ G16H 10/60; G16H 50/20; G16H 15/00; G16H 10/20; G16H 40/20; G16H 50/30;
(Continued)

(56) References Cited

U.S. PATENT DOCUMENTS

| 9,031,926 B2 | 5/2015 | Milward et al. |
| 9,208,217 B2 | 12/2015 | Milward et al. |
| 2015/0213194 A1* | 7/2015 | Wolf .................. G06K 9/00442 705/3 |

OTHER PUBLICATIONS

"Algorithm Implementation/Strings/Levenshtein distance," Wikibooks, last edited on Jan. 5, 2019, 39 pages. Retrieved from Internet. URL: https://en.wikibooks.org/wiki/Algorithm_Implementation/Strings/Levenshtein_distance#Python.
(Continued)

*Primary Examiner* — Joseph D Burgess
(74) *Attorney, Agent, or Firm* — Quarles & Brady LLP

(57) ABSTRACT

A system, method, and mobile device application are configured to capture, with a mobile device, a document such as a next generation sequencing (NGS) report that includes NGS medical information about a genetically sequenced patient. At least some of the information is extracted from the document using an entity linking engine, and the extracted information is provided into a structured data repository where it is accessible to provide information regarding the patient specifically as well as collectively as part of a cohort of patients with similar genetic variants, medical histories, or other commonalities. In one aspect, the document is matched to a template model, and the document is processed using one or more masks segregating the template model, and therefore the document, into a series of distinct subregions.

29 Claims, 30 Drawing Sheets

Related U.S. Application Data

(60) Provisional application No. 62/774,854, filed on Dec. 3, 2018, provisional application No. 62/746,997, filed on Oct. 17, 2018.

(51) Int. Cl.
*G06Q 40/08* (2012.01)
*G16H 50/70* (2018.01)
*G06K 9/64* (2006.01)
*G06K 9/00* (2006.01)
*G06K 9/62* (2006.01)

(52) U.S. Cl.
CPC .......... *G06K 9/628* (2013.01); *G06K 9/6262* (2013.01); *G06K 9/64* (2013.01); *G06Q 40/08* (2013.01); *G16H 30/40* (2018.01); *G16H 50/70* (2018.01); *G06K 2209/01* (2013.01)

(58) Field of Classification Search
CPC ........ G16H 50/50; G16H 20/10; G16H 30/20; G16H 40/63; G16H 40/67; G16H 80/00; G16H 10/65; G16H 30/40; G16H 50/70; G16H 20/00; G16H 10/40; G16H 20/17; G16H 50/00; G16H 70/00; G06F 19/00; G06F 19/321; G06F 19/36; G06F 19/3456; G06F 19/3418; G06F 19/325; G06F 19/3468; G06F 19/3462; G06F 19/30; G06F 19/32; G06F 19/324; G06F 19/3475; G06F 19/3481; G06Q 50/24; G06Q 50/22
See application file for complete search history.

(56) References Cited

OTHER PUBLICATIONS

"Amazon Textract—Easily extract text and data from virtually any document," AMAZON, Nov. 28, 2018, 6 pages. Retrieved from Internet. URL: https://aws.amazon.com/textract/.
"CliNER," Text Machine Lab 2014, Nov. 10, 2017, 2 pages. Retrieved from Internet. URL: http://text-machine.cs.uml.edu/cliner/.
"Clinithink CLiX CNLP (Harness unstructured data to drive value across the healthcare continuum)," Clinithink Limited, 2015, 1 page. Retrieved from Internet. URL: http://clinithink.com/wp-content/uploads//2015/01/Clinithink-CLiX-CNLP-Sell-Sheet-US.pdf.
"Evernote Scannable on the App Store," Jun. 18, 2018, 3 pages. Retrieved from Internet. URL: https://itunes.apple.com/us/app/evemote-scannable/id883338188?mt=8.
"I2E: The world's leading Text Mining platform," 2019 Linguamatics, Aug. 14, 2018, 5 pages. Retrieved from Internet. URL: https://www.linguamatics.com/products-services/about-i2e.
"PHP: levenshtein—Manual," latest comment dated in 2014, 32 pages. Retrieved from Internet. URL: http://www.php.net/levenshtein.
"Talk:Algorithm Implementation/Strings/Levenshtein distance," Wikibooks, last edited on Nov. 2, 2016, 2 pages. Retrieved from Internet. URL: https://en.wikibooks.org/wiki/Talk:Algorithm_Implementation/Strings/Levenshtein_distance#Bug_in_vectorized_(5th)_version.
"Why cTAKES? See the animation below for a sampling of cTAKES capabilities," The Apache Software Foundation, Apr. 25, 2017, 1 page. Retrieved from Internet. URL: http://ctakes.apache.org/whycTAKES.html.
Aronson, Alan "MetaMap—A Tool for Recognizing UMLS Concepts in Text," Jan. 11, 2019, 2 pages. Retrieved from Internet. URL: https://metamap.nlm.nih.gov/.
Balatero, David (dbalatero/levenshtein-ffi) "Fast string edit distance computation, using the Damerau-Levenshtein algorithm," GitHub, Inc., latest comment dated on Aug. 10, 2014, 2 pages. Retrieved from Internet. URL: https://github.com/dbalatero/levenshtein-ffi.
Chen, Huizhong et al. "Robust Text Detection in Natural Images With Edge-Enhanced Maximally Stable Extremal Regions," 2011 18th IEEE International Conference on Image Processing, Sep. 11-14, 2011, 4 pages.
Choi, Edward et al. "Doctor AI: Predicting Clinical Events via Recurrent Neural Networks," Proceedings of Machine Learning for Healthcare 2016, JMLR W&C Track vol. 56, 2016, pp. 1-18.
Choi, Edward et al. "Coarse-to-Fine Question Answering for Long Documents," Proceedings of the 55th Annual Meeting of the Association for Computational Linguistics, Vancouver, Canada, Jul. 30-Aug. 4, 2017, pp. 209-220.
Collobert, Ronan et al. "Natural Language Processing (Almost) from Scratch," Journal of Machine Learning Research 12, (2011) pp. 2493-2537.
Conneau, Alexis et al. "Very Deep Convolutional Networks for Text Classification," arXiv:1606.01781 [cs.CL], Jan. 27, 2017, 10 pages.
Das, Rajarshi et al. "Chains of Reasoning over Entities, Relations, and Text using Recurrent Neural Networks," Proceedings of the 15th Conference of the European Chapter of the Association for Computational Linguistics: vol. 1, Valencia, Spain, Apr. 3-7, 2017, pp. 132-141.
De Bruijn, Berry et al. "Machine-learned solutions for three stages of clinical information extraction: the state of the art at i2b2 2010," 18 J. Am. Med. Inform. Assoc. 2011, May 12, 2011, pp. 557-562.
Dozat, Timothy et al. "Deep Biaffine Attention for Neural Dependency Parsing," Published as a conference paper at ICLR 2017, arXiv:1611.01734 [cs.CL], Mar. 10, 2017, pp. 1-8.
Genthial, Guillaum "Sequence Tagging with Tensorflow (bi-LSTM + CRF with character embeddings for NER and POS)," Guillaume Genthial blog, Apr. 5, 2017, 23 pages.
He, Dafang et al. "Multi-scale Multi-task FCN for Semantic Page Segmentation and Table Detection," IEEE, 2017 14th IAPR International Conference on Document Analysis and Recognition, Nov. 9-15, 2017, pp. 254-261.
He, Luheng et al. "Deep Semantic Role Labeling: WhatWorks and What's Next" Proceedings of the 55th Annual Meeting of the Association for Computational Linguistics, Vancouver, Canada, Jul. 30-Aug. 4, 2017, pp. 473-483.
Kavasidis, I. et al. "A Saliency-based Convolutional Neural Network for Table and Chart Detection in Digitized Documents," Submitted to IEEE Transactions on Multimedia, Apr. 17, 2018, pp. 1-13.
Kim, Youngjun et al. "A Study of Concept Extraction Across Different Types of Clinical Notes," AMIA Annu Symp Proc. 2015; Nov. 5, 2015, pp. 737-746.
Lafferty, John et al. "Conditional Random Fields: Probabilistic Models for Segmenting and Labeling Sequence Data," Proceedings of the 18th International Conference on Machine Learning 2001 (ICML 2001), Jun. 28, 2001, pp. 282-289.
Lample, Guillaume et al. "Neural Architectures for Named Entity Recognition," Association for Computational Linguistics, Proceedings of NAACL-HLT 2016, San Diego, California, Jun. 12-17, 2016, pp. 260-270.
Lang, Francois-Michel et al. "Increasing UMLS Coverage and Reducing Ambiguity via Automated Creation of Synonymous Terms: First Steps toward Filling UMLS Synonymy Gaps," Semantic Scholar, 2017, pp. 1-26.
Laserson, Jonathan et al. "TextRay: Mining Clinical Reports to Gain a Broad Understanding of Chest X-rays," arXiv:1806.02121 [cs.CV], Jun. 6, 2018, 13 pages.
Lee, Kenton et al. "End-to-end Neural Coreference Resolution," arXiv:1707.07045 [cs.CL], Dec. 15, 2017, 10 pages.
Lei, Tao et al. "Rationalizing Neural Predictions," arXiv:1606.04155 [cs.CL], Nov. 2, 2016, 11 pages.
Ling, Yuan et al. "Learning to Diagnose: Assimilating Clinical Narratives using Deep Reinforcement Learning," Proceedings of the the 8th International Joint Conference on Natural Language Processing, Taipei, Taiwan, Nov. 27-Dec. 1, 2017, pp. 895-905.
Lipton, Zachary et al. "Learning to Diagnose With LSTM Recurrent Neural Networks," ICLR 2016, arXiv:1511.03677 [cs.LG], pp. 1-18.

(56) References Cited

OTHER PUBLICATIONS

Ma, Xuezhe et al. "End-to-end Sequence Labeling via Bi-directional LSTM-CNNs-CRF," arXiv:1603.01354v5 [cs.LG], May 29, 2016, 12 pages.

MacKenzie, Andrei (andrei-m/levenshtein.js) "Levenshtein distance between two given strings implemented in JavaScript and usable as a Node.js module," GitHub, Inc., latest comment dated on Feb. 2, 2018, 9 pages. Retrieved from Internet. URL: https://gist.github.com/andrei-m/982927.

Mihalcea, Rada et al. "Part IV Graph-Based Natural Language Processing" excerpted from a book "Graph-Based Natural Language Processing and Information Retrieval," Cambridge University Press, First Published 2011 (Reprinted 2012), 63 pages.

Mysore, Sheshera S. "Segmentation of Non-text Objects with Connected Operators" Msheshera, May 21, 2017, 2 pages. Retrieved from Internet. URL: http://msheshera.github.io/non-text-segment-connected-operators.html.

Narasimhan, Karthik et al. "Improving Information Extraction by Acquiring External Evidence with Reinforcement Learning," arXiv:1603.07954v3 [cs.CL], Sep. 27, 2016, 12 pages.

Neelakantan, Arvind et al. "Learning Dictionaries for Named Entity Recognition using Minimal Supervision," Proceedings of the 14th Conference of the European Chapter of the Association for Computational Linguistics, Gothenburg, Sweden, Apr. 26-30, 2014, pp. 452-461.

Peters, Matthew. E. et al. "Semi-supervised sequence tagging with bidirectional language models," arXiv:1705.00108v1 [cs.CL], Apr. 29, 2017, 10 pages.

Prakash, Aaditya et al. "Condensed Memory Networks for Clinical Diagnostic Inferencing," arXiv:1612.01848v2 [cs.CL], Jan. 3, 2017, 8 pages.

Sager, Naomi et al. "Natural Language Processing and the Representation of Clinical Data," Journal of the American Medical Informatics Association, vol. 1, No. 2, Mar./Apr. 1994, pp. 142-160.

Sambyal, Nitigya et al. "Automatic Text Extraction and Character Segmentation Using Maximally Stable Extremal Regions," arXiv:1608.03374 [cs.CV], Aug. 11, 2016, 6 pages.

Tsou, Ching-Huei et al. "Watson for Patient Record Analytics (aka Watson EMRA)," IBM Research, Aug. 2017, 5 pages. Retrieved from Internet. URL: https://researcher.watson.ibm.com/researcher/view_group.php?id=7664.

Wu, Yonghui et al. "A Study of Neural Word Embeddings for Named Entity Recognition in Clinical Text," AMIA Annual Symp. Proc. 2015; Published online Nov. 5, 2015, pp. 1326-1333.

Zhang, Yuan et al. "Aspect-augmented Adversarial Networks for Domain Adaptation" sentiarXiv:1701.00188v2 [cs.CL], Sep. 25, 2017, 14 pages.

* cited by examiner

| Field | Value |
|---|---|
| Text | "The patient was given Tylenol 50mg at 10:35am." |
| Medication | Tylenol |
| Active Ingredient | acetaminophen |
| Dosage | 50mg |
| Date Administered | 01/01/2001 10:35:01 am CST |
| Document | Progress Note 01_01_01.pdf |
| Page | 3 |
| UMLS CUI | C1234567 |
| UMLS_AUI | RXNORM#12345 |

FIG. 6

MOBILE SUPPLEMENTATION, EXTRACTION, AND ANALYSIS OF HEALTH RECORDS

CROSS-REFERENCE TO RELATED APPLICATIONS

This application is a continuation of U.S. patent application Ser. No. 16/289,027, filed Feb. 28, 2019, which claims the benefit of priority to U.S. Provisional Application No. 62/746,997, filed Oct. 17, 2018, and to U.S. Provisional Application No. 62/774,854, filed Dec. 3, 2018, the contents of each of which are incorporated by reference herein in their entirety.

BACKGROUND

Field of the Invention

A system and method implemented in a mobile platform are described herein that facilitate the capture of documentation, along with the extraction and analysis of data embedded within the data.

Description of the Related Art

In the medical field, physicians often have a wealth of knowledge and experience to draw from when making decisions. At the same time, physicians may be limited by the information they have in front of them, and there is a vast amount of knowledge about which the physician may not be aware or which is not immediately recallable by the physician. For example, many treatments may exist for a particular condition, and some of those treatments may be experimental and not readily known by the physician. In the case of cancer treatments, in particular, even knowing about a certain treatment may not provide the physician with "complete" knowledge, as a single treatment may be effective for some patients and not for others, even if they have the same type of cancer. Currently, little data or knowledge is available to distinguish between treatments or to explain why some patients respond better to certain treatments than do other patients.

One of the tools from which physicians can draw besides their general knowledge in order to get a better understanding of a patient's condition is the patient's electronic health record ("EHR") or electronic medical record ("EMR"). Those records, however, may only indicate a patient's historical status with respect to a disease, such as when the patient first presented with symptoms, how it has progressed over time, etc. Current medical records may not provide other information about the patient, such as their genetic sequence, gene mutations, variations, expressions, and other genomic information. Conversely, for those patients that have undergone genetic sequencing or other genetic testing, the results of those tests often consist of data but little to no analysis regarding the significance of that data. Without the ability to understand the significance of that report data and how it relates to their patients' diagnoses, the physicians' abilities to make informed decisions on potential treatment protocols may be hindered.

Services exist that can provide context or that can permit detailed analysis given a patient's genetic information. As discussed, however, those services may be of little use if the physician does not have ready access to them. Similarly, even if the physician has access to more detailed patient information, such as in the form of a lab report from a lab provider, and also has access to another company that provides analytics, the value of that data is diminished if the physician does not have a readily available way to connect the two.

Further complicating the process of ensuring that a physician has ready access to useful information, with regard to the capture of patient genetic information through genetic testing, the field of next generation sequencing ("NGS") for genomics is new. NGS involves using specialized equipment such as a next generation gene sequencer, which is an automated instrument that determines the order of nucleotides in DNA and/or RNA. The instrument reports the sequences as a string of letters, called a read. An analyst then compares the read to one or more reference genomes of the same genes, which is like a library of normal and variant gene sequences associated with certain conditions. With no settled NGS standards, different NGS providers have different approaches for sequencing patient genomics and, based on their sequencing approaches, generate different types and quantities of genomics data to share with physicians, researchers, and patients. Different genomic datasets exacerbate the task of discerning meaningful genetics-treatment efficacy insights, as required data may not be in a normalized form, was never captured, or simply was never generated.

Another issue that clinicians also experience when attempting to obtain and interpret aspects of EMRs and EHRs is that conventional EHR and EMR systems lack the ability to capture and store critical components of a patient's history, demographics, diagnosis, treatments, outcomes, genetic markers, etc., because many such systems tend to focus on billing operations and compliance with regulatory requirements that mandate collection of a certain subset of attributes. This problem may be exacerbated by the fact that parts of a patient's record which may include rich and meaningful data (such as diagnoses and treatments captured in progress or follow-up notes, flow sheets, pathology reports, radiology reports, etc.) remain isolated, unstructured, and inaccessible within the patient's record as uncatalogued, unstructured documents stored in accompanying systems. Conventional methods for identifying and structuring this data are reliant on human analysts reviewing documents and entering the data into a record system manually. Many conventional systems in use lack the ability to mine and/or uncover this information, leading to gaps in data accessibility and inhibiting a physician's ability to provide optimal care and/or precision medicine.

What is needed are an apparatus, system, and/or method that address one or more of these challenges.

BRIEF SUMMARY

In one aspect, a method includes the steps of: capturing, with a mobile device, a next generation sequencing (NGS) report comprising a NGS medical information about a sequenced patient; extracting at least a plurality of the NGS medical information using an entity linking engine; and providing the extracted plurality of the NGS medical information into a structured data repository.

In another aspect, a method includes the steps of: receiving an electronic representation of a medical document; matching the document to a template model; extracting features from the template model using one or more masks to generate a plurality of expected information types; for each extracted feature, processing the document as a sequence of one or more masked regions by applying the one or more masks; and identifying health information from the one or more masked regions, and verifying the identified health information applies to the expected information types.

In yet another aspect, a method includes the steps of capturing an image of a document using the camera on a mobile device, transmitting the captured image to a server, receiving health information abstracted from the document from the server, and validating an accuracy of the abstracted health information.

In still another, a system provides mechanisms for automatically processing clinical documents in bulk, identifying and extracting key characteristics, and generating machine learning models that are refined and optimized through the use of continuous training data.

BRIEF DESCRIPTION OF THE FIGURES

FIG. 6 is an exemplary table representing a structured result;

DETAILED DESCRIPTION

Figure 1:
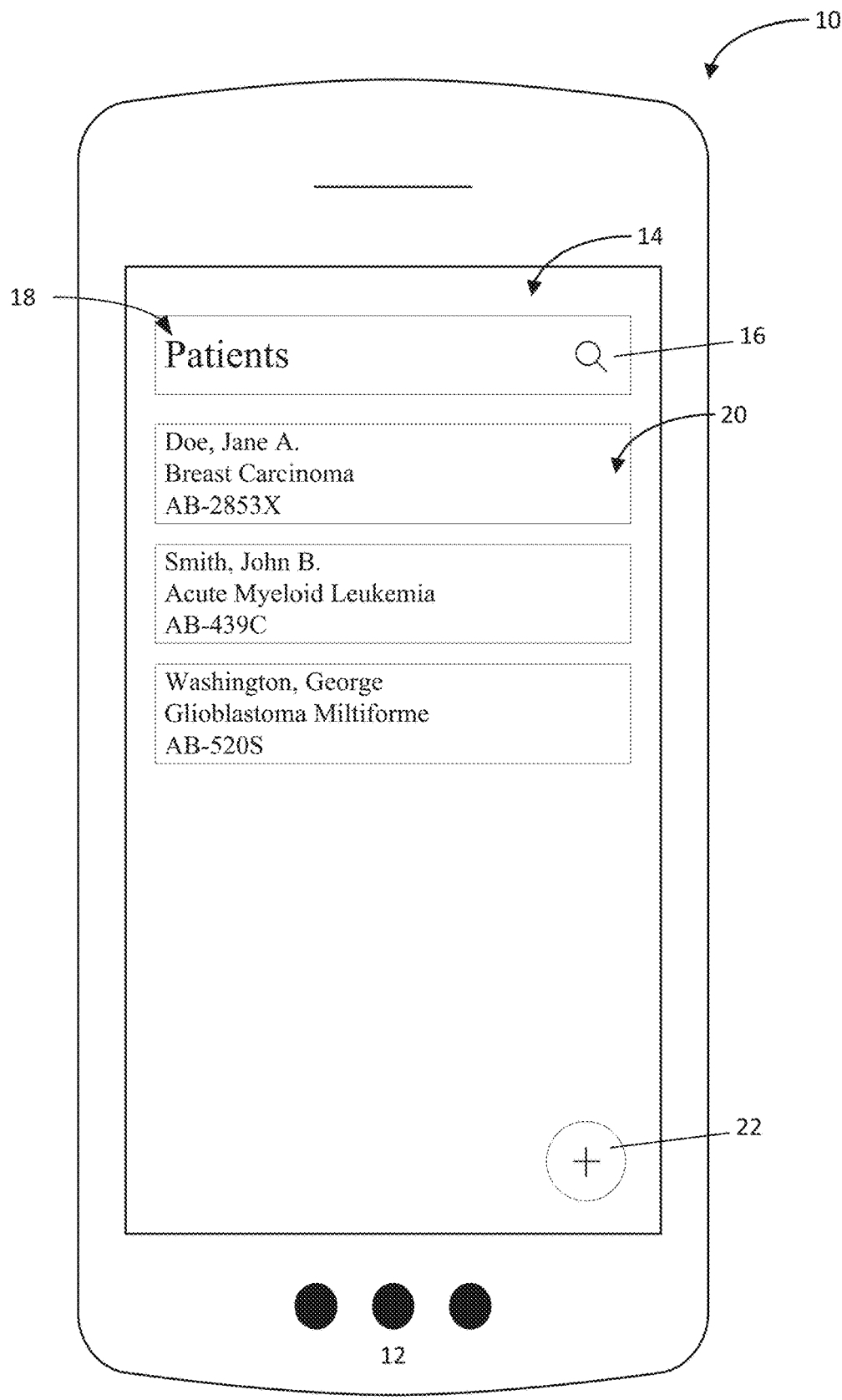
FIG. 1 is a depiction of a home screen of a mobile clinician assistant application.

With reference to FIG. 1, the present disclosure describes an application interface 10 that physicians can reference easily through their mobile or tablet device 12. Through the application interface 10, reports a physician sees may be supplemented with aggregated data (such as de-identified data from other patients' reports) to provide critical decision informing statistics or metrics right to their fingertips. While a mobile or tablet device 12 is referenced herein throughout for the sake of simplicity and consistency, it will be appreciated that the device running the application interface 10 may include any device, such as a personal computer or other hardware connected through a server hosting the application, or devices such as mobile cameras that permit the capturing of digital images for transfer to another hardware system connected through a server hosting the application.

An exemplary device may be any device capable of receiving user input and capturing data a physician may desire to compare against an exemplary cohort to generate treatment recommendations. An exemplary cohort may be a patient cohort, such as a group of patients with similarities; those similarities may include diagnoses, responses to treatment regimens, genetic profiles, and/or other medical, geographic, demographic, clinical, molecular, or genetic features.

Generating a report supplement may be performed by a physician by opening or starting-up the application, following prompts provided by the applications to capture or upload a report or EMR, and validating any fields from the report that the application automatically populated for accuracy. Once captured, the patient's data may be uploaded to server and analyzed in real time; furthermore, cohort statistics relating to the patient's profile may be delivered to the application for the physician's reference and review. The details of this implementation, and more, will be discussed with reference to the Figures below.

In one embodiment, as seen in FIG. 1, a home screen 14 of a mobile application is displayed on the mobile device 12. The home screen 14 may provide access to patient records through a patient interface 18 that may provide, for one or more patients, patient identification information 20, such as the patient's name, diagnosis, and record identifiers, enabling a user (physician or staff) to identify a patient and to confirm that the record selected by the user and/or presented on the mobile device 12 relates to the patient that the user wishes to analyze. In the event that a desired patient is not displayed on the patient interface 18, the home screen 14 may also include a search indicator 16 that, upon selection by the user, receives text input such as a patient's name, unique identifier, or diagnosis, that permits the user to filter the patients by the search criteria of the text input to search for a specific patient. The mobile device 12 may include a touch screen, through which a user may select a desired patient by touching the area on the application interface that includes the desired patient identification information 20. A cursor (not shown) may appear on the screen where the user touches to emphasize touch or gestures received.

Alternative home screens may be implemented that provide a user with options to perform other functions, as well as to access a patient identification information screen, and it will be appreciated that exemplary embodiments referenced herein are not intended to limit the interface 10 of the application in function or design.

Staying with FIG. 1, a user may add a new patient by selecting a corresponding "add patient" icon 22 on the application or through gesture recognition. Exemplary gestures may include swiping across the screen of the mobile device 12 to the left or right, using several fingers to scroll or swipe, tapping or holding down on a portion of the patient interface 18 not occupied by patient identification 20, or any other designated gesture. Alternatively, if no patient data is present in the patient interface 18, the interface may default to adding a user once active. Adding a patient may either be performed manually, by entering patient information into the application, or automatically by uploading patient data into the application. Furthermore, automatic uploading may be implemented by capturing an image of patient data at the mobile device 12, such as from a report, as disclosed below with reference to FIG. 2.

Figure 2:
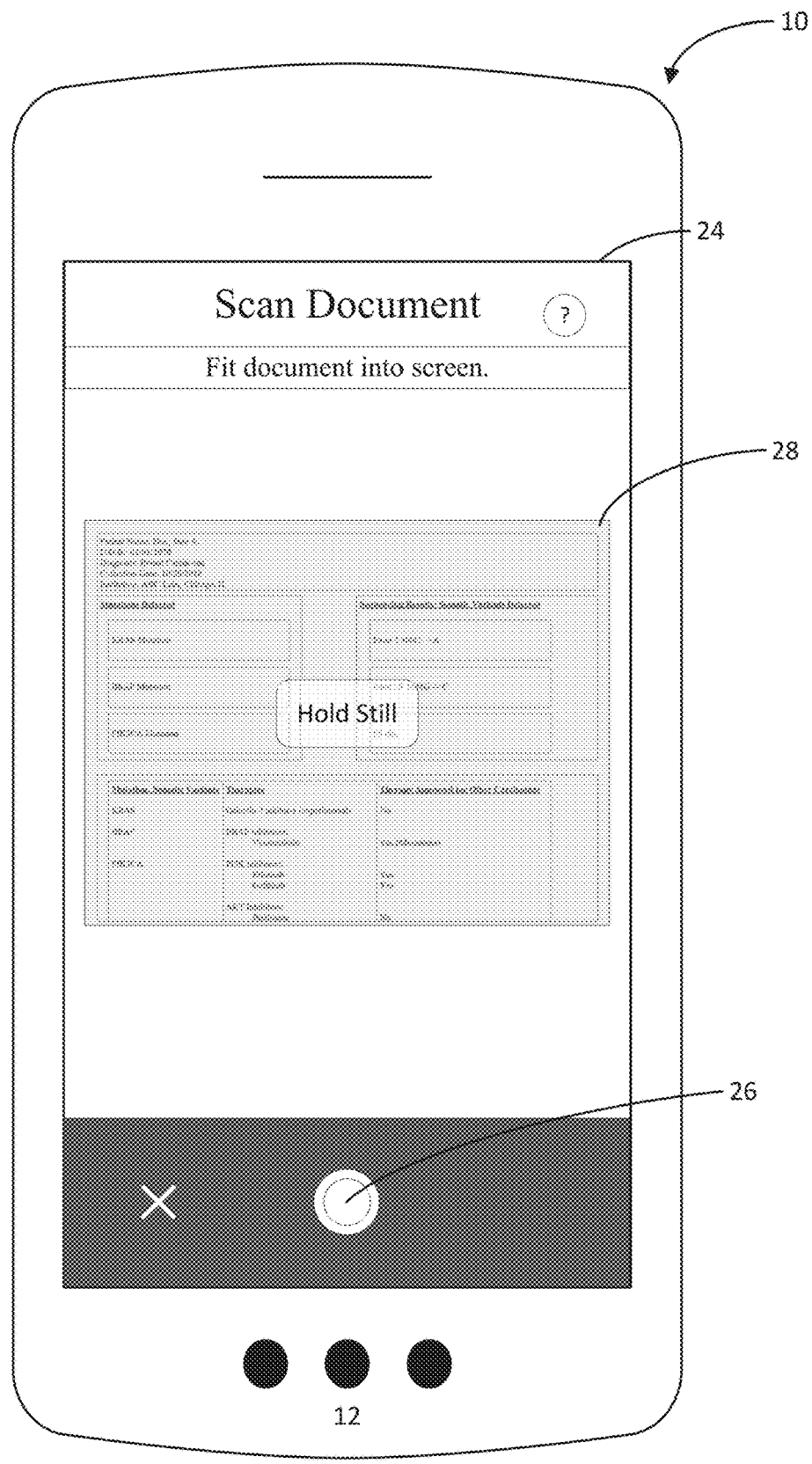
FIG. 2 is a depiction of a document capture screen of the application.

Turning to FIG. 2, once a user has selected a patient, completed adding a new patient, or is adding a new patient from a report, an electronic document capture screen 24 may appear. The system may be configured to capture images of documents that are saved in a plurality of different formats. Exemplary electronic document captures may include a structured data form (such as JSON, XML, HTML, etc.), an image (such as JPEG, PNG, etc.), a PDF of a document, report, or file, or a typeface or handwritten copy of a document, report, or file.

In order to electronically capture a physical copy of a document, the user may place the document on a surface, such as a surface that provides a contrasting color or texture to the document, and aim the mobile device's camera at the document so that an image of the document appears in the document capture screen 24. The user then may select a document capture icon 26 to begin a document capture process. In an alternative embodiment, an automatic capture may be generated once capture criteria are met. Exemplary capture criteria may include that the document bounds are identifiable and/or that the document is in focus.

During the capture process, or once the document capture icon 26 has been selected, the application 10 may launch a document sensing engine that applies an algorithm to scan incoming image data from the device's camera and overlays a document highlight, such as a border or shaded region 28 on top of the document to visually indicate to the user the bounds of the report currently being captured. The document sensing engine may request that the document be placed on a contrasting surface so that the edges of the document, such as the borders of an 8"×10" or 8.5"×11" sheet of paper, are detectable in the camera frame as well as on the electronic document capture screen 24. Upon detecting a document, the application also may request that the user hold the device 12 steady, or still, so a capture may be processed of the document. After the document is captured, the application may prompt the user to take one of a plurality of additional actions, including, for example, recapturing the image, capturing additional images from the document, or indicating that the user is done with the document capture.

In an alternative embodiment, the application may provide an icon on the capture screen or the home screen to upload an electronic data capture, image, or digitized file that is already present on the mobile device. A user may then navigate to the folder on the device containing the document and select it for upload. Part of the upload process may include converting the uploaded file into a preferred format for an electronic data capture.

In one embodiment, an electronic document capture may be generated in black and white, grayscale, or color. If necessary, the electronic document capture may be pre-processed to perform text cleaning and error detection, such as format conversion, resolution conversion, skew detection/correction, or batch sizing, resizing, or processing using document processing tools. Once pre-processed, the document may be submitted for optical character recognition (OCR) on the document to convert the text into a machine-readable format, such as text, html, JSON, or XML using other document processing tools. Once in a machine-readable format, error correction, such as spell checking, noise removal, or context based correlation may be performed on the now-machine-readable text using still other document processing tools. It should be appreciated that the document processing tools may be a single tool or may be a collection of tools from which the requisite tool for the processing task is selected in turn. When processing electronic document captures, many document formats may require format conversion from an unsupported format to a supported format. Exemplary conversions may take documents of a variety of formats, including, for example, XML, HTML, rich text, PDF, PNG, or JPG, and convert them to a format that a respective OCR service accepts, such as JPG or PNG. During format conversion, additional processing may be performed for parameter optimization for each respective document to achieve the best results from the OCR service selected, for example, by converting documents from a source resolution, or dots per inch (dpi), to a resolution best supported or by combining multiple requests into one to optimize batch processing. Furthermore, another advantage of batch processing is discussed below with respect to FIG. 3.

In another embodiment, additional pre-processing may be performed after submitting an image to OCR to determine whether the detected text is "reasonable" before outputting final results. In one example, the word "beast" may rarely occur in an a patient report, for example, as "patient was mauled by unknown beast;" however, "breast" may occur more frequently, for example, as "patient expresses concern re: lump in breast," "breast cancer," "stage iv breast cancer," or "patient's breast recovered from surgery," giving "breast" a much higher probability of occurrence weighting than "beast." As a result, a reasonability determination may replace "beast" with "breast," and indicate that the resulting OCR text is reasonable. While some OCR technologies may perform their own reasonability determination, it may be necessary to further improve upon the quality of the OCR output by performing a text cleaning algorithm on the OCR output.

In one embodiment, a document classifier may process the OCR output of the electronic document capture to recognize document identifiers which are linked to features of the document stored in a predefined model for each document. Predefined models may also be referred to as predetermined models. Document identifiers may include Form numbers (such as Form CA217b, Patient Report Rev. 17, AB12937, etc.) indicating a specific version of a document which provides key health information in each of the respective document's features. Features of a document may include headers, columns, tables, graphs, and other standard forms which appear in the document.

Exemplary predefined models may be a JSON file, HTML, XML, or other structured data. Predefined models may store a list of features that are derived from the document based on MLA processing. The processing may occur over a plurality of MLA processing steps and/or sub-steps, each of which may output certain features to the predefined model after each processing step as discussed in further detail below. Each of these features may additionally have a required or optional tag identifying whether the feature must be present or may be present. Furthermore, each feature may have a list of expected key health information types. For example, a header may expect a patient name, a patient date of birth, an institution name, a report date, a diagnosis, etc. The list of features and corresponding expected key health information may be encoded into the predefined model. Furthermore, a mask, natural language processing model, and other extraction guidelines may be stored in the predefined model. Extraction guidelines may include reliability checks to ensure that the information is correct. For example, a diagnosis date may not occur before birth, or a treatment date may not occur after death. Masks, natural language processing models, and other extraction guidelines are discussed in further detail below and, in addition, with respect to FIG. 3. Predefined models may be the result of a machine learning algorithm (MLA) or may be curated by hand for each report type. It should be appreciated that a predefined model may include or exclude additional criteria and/or differing levels of the above criteria, in addition to other unmentioned criteria based upon the report type, the curating method, or user preference.

In another embodiment, document identifiers may be generated from the MLA. A MLA may not generate easily human recognizable patterns, such as the form numbers above. Instead a MLA may identify a document by pixel arrangements, locations, colors, or other features. For example, a standard report may have a test provider's logo in the top left hand corner of the first page and a header encased in a solid black border after the logo. The MLA may identify distinguishing characteristics, pixels, or colors from the logo and the thickness of the border of the header a seemingly random placement as a unique document identifier which is consistent between reports. Furthermore, even if a document is identified as "Form CA217b", the MLA may not use the text for identification purposes but instead identify, for example, that the pixels of the "F" are in a slanted line.

As a result of the OCR output, the application also may identify medical data present in the document. Medical data, or key health information, may include numerous fields including, but not limited to, patient demographics (such as patient name, date of birth, gender, ethnicity, date of death, address, smoking status, diagnosis dates, personal medical history, or family medical history), clinical diagnoses (such as date of initial diagnosis, date of metastatic diagnosis, cancer staging, tumor characterization, or tissue of origin), treatments and outcomes (such as therapy groups, medications, surgeries, radiotherapy, imaging, adverse effects, associated outcomes, or corresponding dates), and genetic testing and laboratory information (such as genetic testing, performance scores, lab tests, pathology results, prognostic indicators, or corresponding dates).

Each of the fields, for example the address, cancer staging, medications, or genetic testing may also have a plurality of subfields. The address field may have subfields for type of use (personal or business), street, city, state, zip, country, and a start or end date (date that residency at the address begins or expires). Genetic testing may have subfields for the date of genetic testing, testing provider used, test method, such as genetic sequencing method or gene panel, gene results, such as included genes, variants, expression levels/statuses, tumor mutational burden, and microsatellite instability. One type of genetic testing may be next-generation sequencing (NGS). The above-provided examples, enumerations, and lists are not intended to limit the scope of the available fields and are intended to be representative of the nature and structure that fields may take.

In some instances, the application may direct a user to scan additional pages of the document based on the predefined model associated with the recognized document identifier. For example, if a 20-page report features key health information on pages 1-5 and 17, the application may determine the format of the report and request the user to process an electronic document capture on each of pages 1-5 and 17 before performing additional data extraction. In another example, if a report has a non-standard page layout, the application may request the user to skip background sections, waivers, privacy notices, or other pages which do not contain key health information when capturing pages of the document. Exemplary key health information may be found in features of the document such as headers and tables. An exemplary header may include a standardized format with key health information such as a patient's name, date of birth, age, gender, diagnosis, treating facility, and other medical data detailed above. An exemplary table may also include key health information in the form of report summary information such as mutations or genetic variants identified during sequencing of a patient's DNA or gene expression counts identified during sequencing of a patient's RNA. Extraction techniques are discussed in more detail below.

In another embodiment, the electronic document capture may reference the predefined model to identify the region of the electronic document capture containing key health information and extract the identified region for further processing. A region (such as a header, table, graphic, or chart) may be identified by utilizing a stored feature list for the document, or each page of the document, that identifies features present in the page along with their corresponding locations in the page. For example, the model may indicate that a page should expect to present a patient header, two tables, a chart, and a graph. A region mask may be applied to the capture to verify that any regions expected to be present are actually within the capture. A region to extract may be identified by the region mask and, upon verifying that the region is present, the region may be extracted. Text may be identified from the extracted region and provided to a natural language processing (NLP) algorithm to extract patient information, such as patient name, diagnosis, notable genetic mutations, or gene expression count information including count values representing the number of times the RNA sequence occurs in sequencing and/or deviation in gene expression counts compared to the gene expression counts of normal samples that may be labeled over or under expressed. More details for feature/region detection and extraction are discussed below with respect to tabular extraction.

Each field of the extracted region may have a plurality of enumerated values, or, if an enumerated list of values is unavailable may be limited to a certain type of value. For example, if the field relates to patient diagnosis, it may have a corresponding enumerated list of all diagnoses that may be provided in the report. If the field relates to a treatment, it may have all known treatments and further parse the field to identify and enumerate unknown treatments. Alternatively, if the field is a medication that the patient was prescribed, it may be limited to a type, so that data parsed will be checked against known medications and, if necessary, add the parsed text to a medications database as a new entry of type medications. The types of field, their enumerated values, or the classification associated with unknown values may be stored as part of the predefined model.

In an alternate embodiment, a tabular extraction method may be performed on the OCR output of the electronic document capture. Where the above method requires that each document type has a predefined model in-place to capture specific elements from the document, a tabular extraction approach may process a document type without a predefined model and generate a model as an output of an algorithm, described in more detail with respect to FIG. 3, below. For example, every report may include patient information or demographics such as the patient's name, date of birth, diagnosis, or institution which may be automatically parsed without particular knowledge of the specific report. In addition, specific reports may be discernible contextually, for example, a genetic sequencing report may include listing of genes, mutations, variants, and expressions which would indicate that the report may provide certain classifications of patient information that should be extracted. A gene field may be tagged as required, as any sequencing report may present this information and a mutation, variant, or expression field may be tagged as optional as different sequencing reports may present differing types of information (such as a DNA report may include mutations, but not expression).

Figure 3:
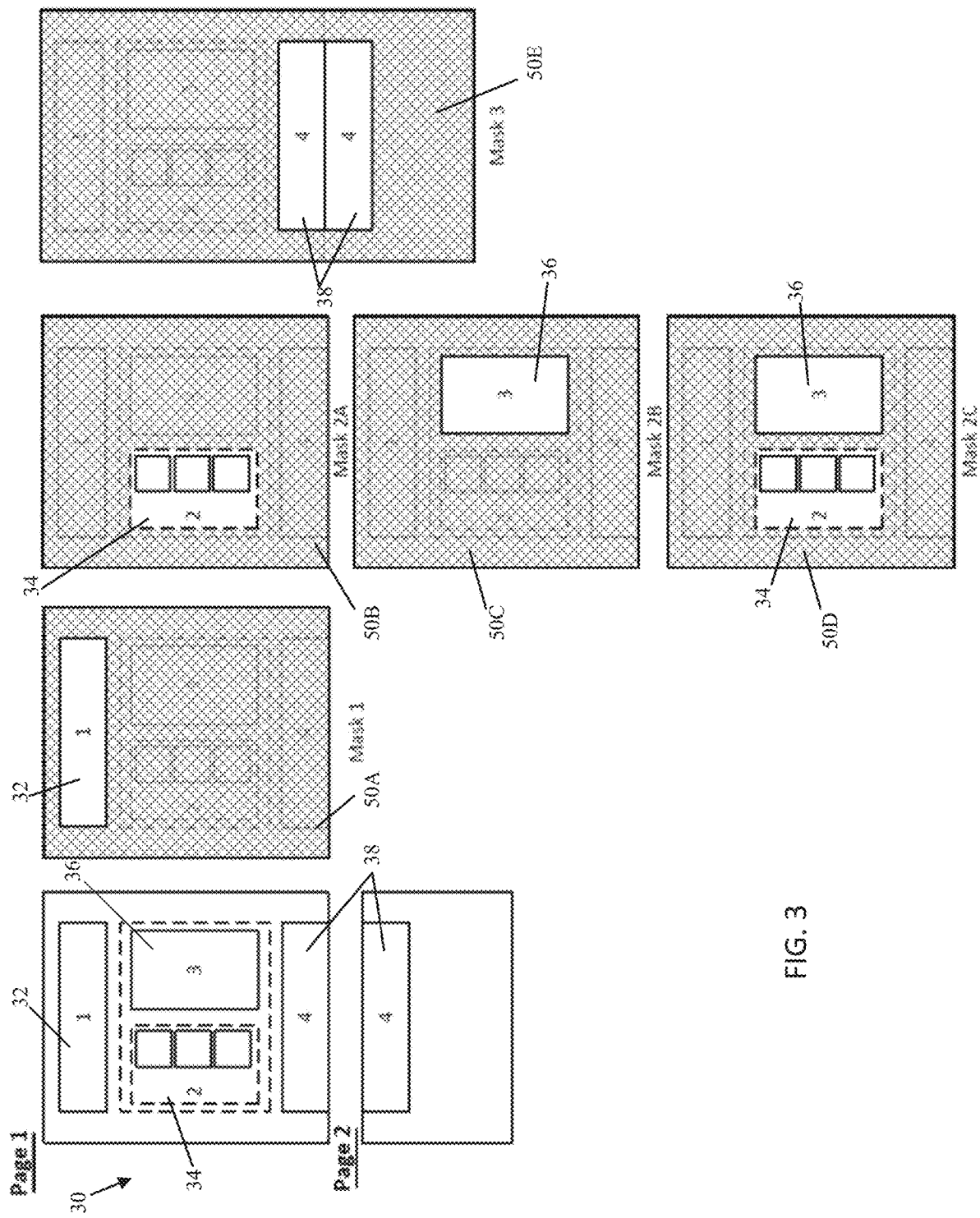
FIG. 3 depicts an exemplary tabular extraction approach involving a plurality of different masks.
Figure 4A:
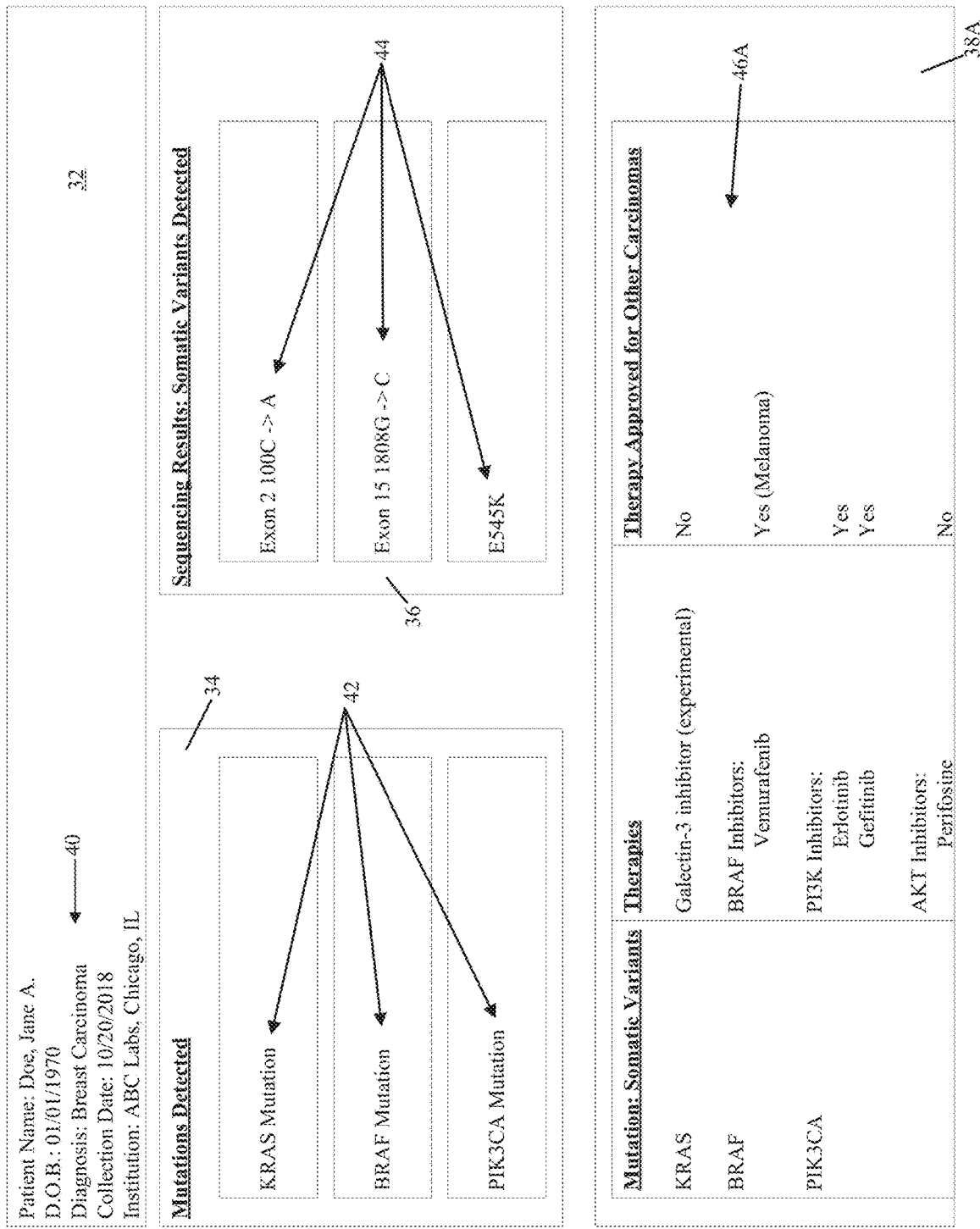
FIG. 4A is a depiction of a standard report to which the masks of FIG. 3 may be applied in order to extract and analyze the data contained therein.
Figure 4B:
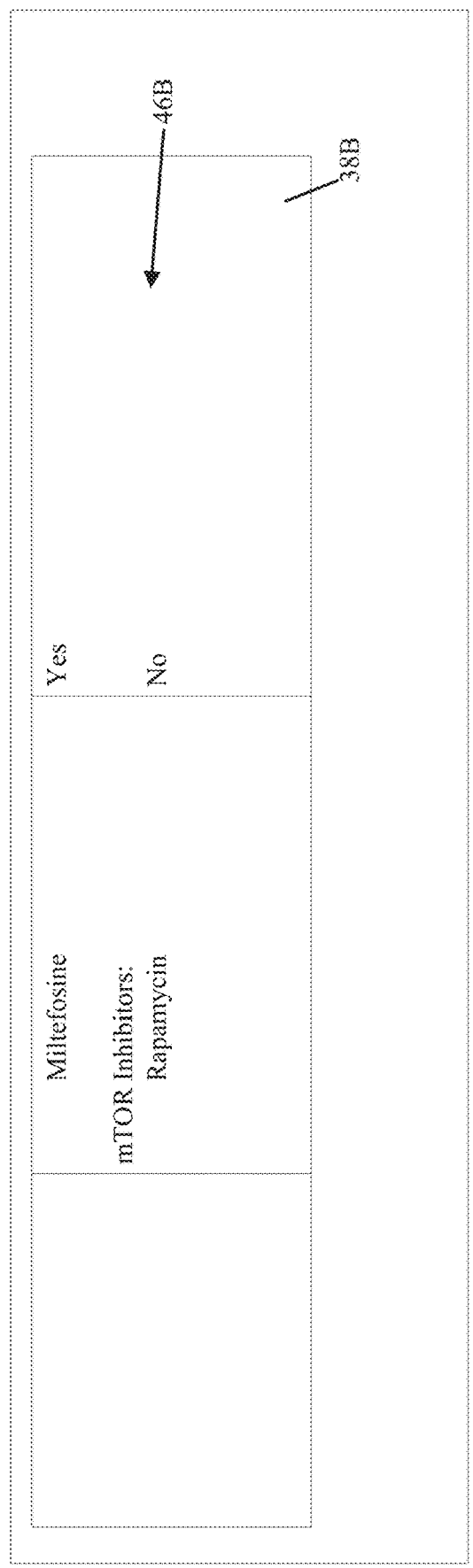
FIG. 4B is a continuation of the report of FIG. 4A.

FIG. 3 depicts an exemplary tabular extraction approach involving masks 1-3. In this example, the document 30 being extracted may be a standardized report, such as a report used by a physician or group of physicians, including patient onboarding forms, progress notes, pathology reports, and other standard documents. Standardization in this situation may indicate that the reports are presented in a general format with regularly occurring fields (permanent or optional) populated specific to a patient. For example, a patient onboarding form may have a header 32 (as shown in FIGS. 4A-B) which lists patient information such as name, address, symptoms, medications. A progress note may have a table that allows the physician to catalog treatment options recommended to the patient, treatment options which were pursued from a previous visit, and any updates to the status of the patient relating to the treatment options pursued. A pathology report may include a first section 34 listing a plurality of genetic variants that may be tested in a specific pathology assay and a second section 36, which may be distinct from the first section, providing sequencing results for each corresponding genetic variant of the first section at a spatially corresponding location to the first section. Furthermore, some reports may feature tables, charts, or other sections 38 that may expand or be split across multiple pages, similar to section 4 of Mask 3 (also shown in FIGS. 4A-B).

In this context, a MLA or a deep learning neural network (DLNN) may be utilized. The MLA may have been trained with a training dataset that comprises annotations for types of classification that may be performed. It should be understood that the terms MLA and DLNN are interchangeable throughout this disclosure. Thus, a mention of MLA may include a corresponding DLNN or a mention of DLNN may include a corresponding MLA. A resulting ruleset or neural network may identify or recognize a plurality of features across a standardized report or other template signifying that a classification may be extracted from a specific section of a particular report based at least in part on that extraction ruleset. Exemplary metrics and features that may be applied are discussed in more detail below.

As noted above, one type of document that the system may be configured to capture is a genetic testing report and, in a particular aspect, a next generation sequencing (NGS) report. For example, once the mobile device captures the NGS report about a sequenced patient (for example, by generating an electronic document capture), the system may extract some or all of the NGS medical information (such as patient information, genes, mutations, variants, or expression data) contained in the document. Using various OCR, MLA, and DLNN techniques, such as those described herein, that extracted information then may be stored in a database or other data repository, preferably in a structured format.

The system may be configured to recognize various types of NGS medical information from the captured report. For example, the system may be configured to extract and recognize NGS medical information relevant to one or more diseases, including: cancer, diabetes, depression, cardiovascular disease, neurological disorders, infectious diseases, lupus, or endocrinology-related diseases. The NGS medical information additionally may include one or more of: somatic variants, germline variants, tumor mutation burden (TMB) values, microsatellite instability (MSI) values, therapy resistance values, organoid response values, epigenetic values, RNA expression values, locus-based somatic variants, and/or gene-based somatic variants. Still further, the NGS medical information may focus on specific genetic mutations, such as a KRAS mutation, a BRCA mutation, an EGFR mutation, a CYP2C19 mutation or other mutations, such as any of the genes referenced below.

Once the system extracts the NGS medical information, the system then may classify or correlate that information to other medical data, based, e.g., at least in part on the feature(s) from which it is extracted. For example, the system may correlate the NGS medical information to prior treatment data, including medication and/or chemotherapy data. The system also may correlate the NGS medical information to prior outcomes data, including survival, remission, and/or tumor progression data. It will be appreciated that the prior treatment and/or prior outcomes data may be from the patient to whom the NGS medical information relates or from patients other than the sequenced patient.

Turning to FIGS. 4A-B, an exemplary NGS report featuring Sections 1-4 as described in FIG. 3 may be processed by an MLA or DLNN to identify Section 1 as a header 32 which lists a plurality of features 40, such as a patient's name, date of birth, and diagnosis; the institution's name and location; and the date of report, of data collection, etc. The MLA may also identify extraction techniques to apply, such as use sentence splitting algorithms to parse a plurality of sentences and then regular expressions to match "Patient Name:", "D.O.B.:", "Diagnosis:", "Collection Date:", and "Institution:" or alternatively splitting the sentences on the colon (":") character and applying the first results to a patient name field, second results to a date of birth field, third result to a diagnosis field, fourth result to a collection date field, and fifth result to institution name and location fields.

The MLA may identify Section 2 as a region 34 including a plurality of features 42, such as a listing of genetic mutations which are linked to Section 3. For example, within this other region 36, the MLA may enumerate additional features 44, including all possible genetic mutations or variants that may occur in Section 2. Additionally or alternatively, the MLA may be trained to identify the word "Mutation" and then determine that the text immediately preceding or following that word is a candidate for a possible mutation. In this regard, the system may utilize the nature of mutation descriptions, namely that many mutations are represented by unique alphanumeric phrases, such as "KRAS," "BRAF," and "PIK3CA" in FIG. 4A. Thus, when the MLA identifies these phrases, it may compare them against a database or dictionary or known mutations such that, when one or more matches are found, the MLA may be able to conclude with a high degree of confidence that the match corresponds to a possible mutation, in other words, a risk of a false positive is low. Still further, because the mutations of Section 2 are linked to the variants in Section 3, the MLA may perform a two-way cross-check against the dictionary or database in the event that the text extracted does not correspond to a known mutation or variant. A two-way cross-check may also be performed to another section within the report such as an appendix or glossary. For example, if the system read the mutation "KRAS" as "RRAS," it would not find the latter mutation in its database or dictionary. At that point, the system may check its corresponding variant—in this case, "Exon 2 100C→A," determine that there is a match in the database or dictionary for that variant, and determine that the mutation corresponding to that variant is "KRAS." At that point, the MLA may either accept the change automatically, or it may do a comparison between the extracted term, such as "RRAS," and this matching term, "KRAS." The MLA may rely on various comparators, such as the number of characters in each term, the number of matching characters in each term (such as the second character in each term is an "R," the third character in each term is an "A," and the fourth character in each term is an "S"), a comparability score between the non-identical characters (such as "K" and "R" may be given a higher comparability score than "K" and "Q," as the former set of characters more closely resemble one another than the latter), or other comparators, in order to determine a likelihood of match. If the match likelihood is above a certain threshold, the MLA then may conclude that the extracted term should be modified to the matching term and will replace the term accordingly.

Furthermore, the MLA may identify a number of fields that may be extracted in this section as a range of values. For example, if there is always at least 1 mutation listed but never more than 9, the MLA may identify a range from 1-9 for extraction, similarly, if there are no mutations listed, the MLA may "tag," or annotate, this field as optional and include a range of 0-9 mutations for extraction.

The MLA may identify each row in Section 3 as a corresponding sequencing result to the genetic mutation of Section 2 in the same row. For example, if there are three rows in Section 2 identifying KRAS, BRAF, and PIK3CA mutations, there should exist at least three rows in Section 3 which feature corresponding variants to the KRAS, BRAF, and PIK3CA mutations, respectively. The MLA may identify column and row numbers or just row numbers for the number of genetic mutations, variants, or expressions to extract based upon the detected structure during processing.

It is possible that there may be more than one variant detected for a given mutation. In that regard, different document types may report that information differently. For example, one type of document may provide the information in a 1:1 fashion, such that there may be two rows in Section 2 with the same mutation listed, each row corresponding to a unique variant in Section 3. Alternatively, a different document type may group all variants for a given mutation in the same box in Section 2, those different variants separated by some kind of indicator, such as a comma, semicolon, colon, slash, backslash, new line, etc.

Lastly, the MLA may identify Section 4 as a region 38A a multi-page table in which its features 46A include summaries of conclusions made from the sequencing results of Sections 2 and 3. In this example, Section 4 spans multiple pages, and the system may recognize that the portion 38B of Section 4 on the second page (FIG. 4B) is a continuation of the portion of Section 4 on the first page, with additional features 46B. For example, the MLA may recognize a width of the columns in both of the portions and determine that the widths of the respective portions of each column are the same, the first column in Section 4 in FIG. 4A is the same width as the first column in FIG. 4B. In another instance, the portion at the top of the second page may include one or more headers, which the MLA may recognize as the same header(s) as the portion of Section 4 at the bottom of the first page. In still another instance, the MLA may recognize other text (such as "Continued" or "Cont'd" or " . . . "), signaling that the portion at the top of the second page is a continuation of Section 4.

The MLA may identify a column and row structure where column 1, rows 1-N correspond to Rows 1-N of Section 2. The MLA may further indicate that OCR results of the previous Sections may be verified by comparing with the current section and vice versa. Furthermore, the MLA may identify that Column 2 of Rows 1-N correspond to therapies of genetic mutations detected in Section 2 and that Column 3 or Rows 1-N identify whether the therapies are approved for other cancer types. For example, if there are three rows, an exemplary model may identify that for N rows, column-row pair 1-1, 1-2, . . . 1-N, each identify a mutation; column-row pair 2-1, 2-2, . . . 2-N, each identify a therapy for that mutation; and column-row pair 3-1, 3-2, . . . 3-N, each identify if alternate carcinomas may be treated with the therapy. Just as there may exist N rows there may also exist some number, M, of columns such that column-row pairs M-1, M-2, . . . M-N exist and relationships between the columns and rows may be represented.

Alternatively, the discrete elements in one or more of the columns may span more than one row. For example, in FIGS. 4A-B, the therapies may be presented as a class of therapy on a first row, such as "PI3K Inhibitors;" followed by one or more specific therapies within that class, such as "Erlotinib" and "Gefitinib," on separate, successive rows. The MLA may be trained to recognize that an indentation from one row to the next may indicate such group/instance relationships, that successive lines with no indentation may signify a continuation of the text of the first line, and/or that a certain minimum amount of white space between lines may signify a break from one class of therapies to the next.

Each of the above identifications, validity checks, or other determinations made by the MLA may be encoded and stored in the predetermined model (or predefined model as discussed above) for reference during processing of a report sharing the same template. In this regard, the model may be considering an overarching rule set used to identify a report or other document. The model may be generated from the MLA, from a human curation, or a combination thereof (such as an MLA model supplemented with additional human curation). Templates for each document may be one component of the model, along with identifiers for each template, regions or masks, features or fields and tools or instructions for how to extract those features or fields and verify the accuracy of that extraction, associated sub-fields, and rules for normalization of those fields and sub-fields.

One exemplary technique to access the data within each of the identified sections may be to generate a mask which "outlines" the section, apply the mask to the document to extract each section in turn, and then provide the section to an OCR algorithm, such as an OCR post-processing optimized to extracting information from the respective section type.

As discussed above, exemplary masks for extracting each of the Sections 1-4 are disclosed in FIG. 3. Mask 1 may identify the bounds of Section 1, for example, by identifying a size (such as number of pixels, width, length, diameter, etc.), shape (such as square, rectangle, or other shape), and origin point (such as a pixel X,Y pair) for a mask 50A or by identifying a starting (such as the pixel location of the top, left side) and ending point (such as a pixel location of the bottom, right side) of a rectangular mask. Other field designations may be useful for other shapes, for example, a circle may have an origin and a diameter, or any enclosed shape (polygonal or combinations of shapes), such as an L shaped box may have multiple corner points outlining the exterior of the mask in a node/edge graph relationship establishing nodes, edges shared between nodes, and the location of each node. The mask may be a numerical 1 for the white region or 0 for the black region. Alternatively, the mask may be 1 for a pixel intensity value greater than/greater than or equal to a certain threshold and 0 for a pixel intensity less than or equal to/less than a certain threshold. The pixel values of the document then may be multiplied with the corresponding mask value to apply the mask or may be applied in a binary fashion such as a logical AND operation. For example, only the region of the image which is multiplied, or logical AND operation, with a 1 are kept for OCR; the region that is multiplied, or logical AND operation, with a 0 is lost. Once the mask is applied, an exemplary optimized OCR post-processing for that section may include a regular expression, such as a regular expression or matching a string "Name:" or "DOB:", and/or a column, row pair(s) which contains key health information, for example, a cell located at Column 2, Row 2 may provide a patient name, or a cell located at Column 2, Row 3 may provide a patient date of birth. In a similar fashion, Section 2 may be extracted next using a second mask 50B and Section 3 may be extracted using a third mask 50C. Sections 2 and 3 may then be supplied to OCR post-processing for linking the results of Section 3 to the enumerated content of Section 2. In an alternate embodiment, Sections 2 and 3 may be extracted at the same time using a combined mask 50D. Section 4 may similarly be extracted at the same time using a combined mask 50E by appending/concatenating the image of page 1 and page 2 together or may be masked individually for each page and the resulting masked sections may be appended/concatenated for post processing. In other alternative embodiments, masking may be performed by cropping the image, extracting only the image along a bounded box, or other image segmentation techniques.

As discussed above, the MLA may search for one or more keywords or phrases identifying the entity generating the document, such as the "Institution:" keyword in Section 1 may trigger the MLA to understand that the word or words following the ":" are an indicator of document source. The MLA then may use that information, alone or in combination with other extracted data such as the Collection Date value, a Version No., etc., to access a stored library of templates. For example, with regard to FIG. 4, the system may include one or more stored document templates for documents created by "ABC Labs," and the Oct. 20, 2018, collection date may inform the MLA as to which document to use when there are multiple documents.

The MLA or DLNN performing tabular extraction may be implemented as a single training set for all documents, or it may be segmented into one or more layers to improve processing speed of the each stage of the extraction process and to allow modular improvements to be incorporated without retraining the entire process at once. An exemplary multi-layer extraction may be performed through a template-based approach using a supervised or semi-supervised training set or may be performed through a fully tabular approach using an unsupervised or semi-supervised training set. In an exemplary template-based approach, an MLA may be provided with specific forms containing a standardized layout for each document type commonly found in electronic document captures. Additional information on how to identify the form may be provided (such as a location/bound to OCR and a text string to match a document name). In another embodiment, the MLA may train to discern how to identify the form and may train to recognize concept candidates in the specific form document provided. The template-based approach (as described above) may further incorporate the methods and processes of the instant tabular approach to operate consistent with the below description.

In an exemplary tabular approach, a first layer of a multi-layered MLA may process (in training) electronic medical record (EMR) and electronic health record (EHR) documents to identify documents of similar form, layout, or structure. For example, in an EMR of a 1000 documents, the first layer MLA may identify that 400 of the documents follow a first similar form (such as the document in FIG. 4 for the form in FIG. 3), 300 follow a second similar form different from the first, and the remaining documents do not follow a similar form. The MLA may identify one or more of a first subset of masks for the 400 documents of first similar form (such as Sections 1-4 of FIG. 3) and may identify one or more of a second subset of masks for the 300 documents of a second similar form. An output of the MLA from the first layer may be a series of masks for each of the identified similar forms. In another embodiment, the first layer may be broken up into a series of MLA; for example, the processing flow of the first layer may be arranged to divide the tasks of recognizing similar documents to identify a potential template and then process each template to generate masks for each of the identified templates as two or more operations. The results of each layer of the MLA processing may be encoded into the predefined model for retrieval during processing or may be encoded in the neural network of the DLNN.

A second layer of a multi-layered MLA then may utilize the resulting masks from the first layer to process the training data set by identifying regions of interest in a document, identifying a corresponding mask for each identified region of interest, and applying the mask to each document to extract and process the region of interest. An exemplary intermediary processing step of the second layer MLA may identify, for each region of interest, which type of feature the region of interest may contain (such as a table, header, graph, etc.). An output of the MLA from the second layer may be a series of masked images for each of the regions of interest and an indicator for the type of feature that exists in the region of interest.

In another embodiment, the second layer may be broken up (or consolidated) into a different series of MLA; for example, the processing flow of the second layer may be arranged to divide the tasks of applying each mask to each region of interest and identifying the features of the region of interest into a single operation or further subdivide the processing into further operations.

A third layer of a multi-layered MLA may utilize the resulting masked regions of interest and identified features for each region to select an optimized OCR post-processing to extract the text from the region of interest. An exemplary optimized OCR post-processing for that section may include a regular expression, such as a regular expression or matching a string "Name:" or "DOB:", and/or a column, row pair(s) which contains key health information, for example, a cell located at Column 2, Row 2 may provide a patient name, or a cell located at Column 2, Row 3 may provide a patient date of birth. Further post processing of the OCR text may identify that regions of interest are related to one another. For example, a first region of interest may provide a series of gene variants while a second region of interest may provide the expression level/status of those gene variants. In this example, there are a known number of genes, each having a plurality of possible variants, and a query to a molecular pathology service may be initiated to validate whether a recognized gene and variant combination is valid/known or if the combination is actually an unrecognized variant, an OCR introduced error, or if the unknown combination originated from the document. The MLA may detect that regions are related and assign a corresponding concept candidate using both of the regions of interest together. By utilizing relationships between regions of interest in the document, the MLA may provide a more robust classification and provide a more detailed error checking than an algorithm that analyzes portions of the document in isolation. Related regions may further be used to provide error correction or OCR validation. For example, certain reports may include a feature that includes genetic variations that have been overexpressed in an RNA report. A second feature nearby may represent the same overexpressed genetic variants but further provide therapies targeting these genetic variants, and potential clinical trials that may be relevant. The reuse of data in subsequent features provides an opportunity for validating correct OCR results by comparing the results from each of these respective features. In another example, an appendix may be included at the end of the report that provides all variants which may be included. If an OCR error of a variant has occurred, then that result may not match any entry in the appendix, and may be corrected.

An unrecognized variant is one that has not been identified, sufficiently classified, or expertly-curated by the scientific community. Generally, reports include only known variants and publish updated documentation for any newly supported variants for each test/report offered. An output of the MLA from the third layer may be a collection of concept candidates or classifications for the document/patient. In another embodiment, the third layer may be broken up (or consolidated) into different a series of MLAs; for example, the processing flow of the third layer may be arranged to divide the tasks of text extraction, classification, and identifying relationships between regions of interest into a single operation or further subdivide the processing into further operations.

While the instant embodiments are described as including three layers with respective intermediate processing steps, it should be understood that each layer and the included intermediate processing steps may be reordered, combined, or skipped based on the layout of the training documents and configuration of the MLA. Therefore embodiments having fewer or extra layers may be realized without departing from the spirit of the disclosure. Furthermore, the outputs of each layer of the MLA may be encoded as rules in the predefined model for retrieval during processing of a new document.

Identifying regions of interest, features within the region of interest, or relationships between regions may be performed from the OCR text itself or processed from the image itself prior to OCR. For example, identifying a region of interest may be performed by identifying a border (such as a black box) that encapsulates some segment of text. In some instances, a border may actually be identified using the negative space (such as the white space) around a text by observing that the white space is of at least a uniform distance all around a segment of text and creating a natural boundary. For example, white space that also borders an edge of a paper may be several times as thick as the white space above and below the segment of text, but there will be at least a uniform white space of the width above and below, that is also present in the larger section on the border. Other distinctions may be observed and utilized as well based on the MLA applied. For example, a table may be identified by observing two or more intersecting lines. Similarly, lines segmenting the columns and rows of a table may be solid, dashed, or even extrapolated from the negative space between the words. Additionally or alternatively, OCR post-processing may recognize text which is presented in columns to combine the text in the correct order. Certain features may be identified based on the image of the text prior to OCR. For example, text in all capital letters may be identified by having more straight lines than typical text, bold text may be identified by having thicker letters than typical text, or italicized text may be identified by have angled lines more frequently than typical text. These features of text may be applied in determining regions of interest, related regions, or concept candidates from each region of interest. Furthermore, features of text may be identified by both image details (such as pixel density, pixel chroma, etc.) and text (such as the OCRed words themselves are shared between documents). It is appreciated that MLA and DLNN may identify features, relationships, and masks using any number of techniques which may not be easily predicted or explained herein, the above examples are merely exemplary, and easily identified/understood to illustrate the types of features that may be important to the MLA and DLNN but are not a full accounting of the possibilities.

Figure 16:
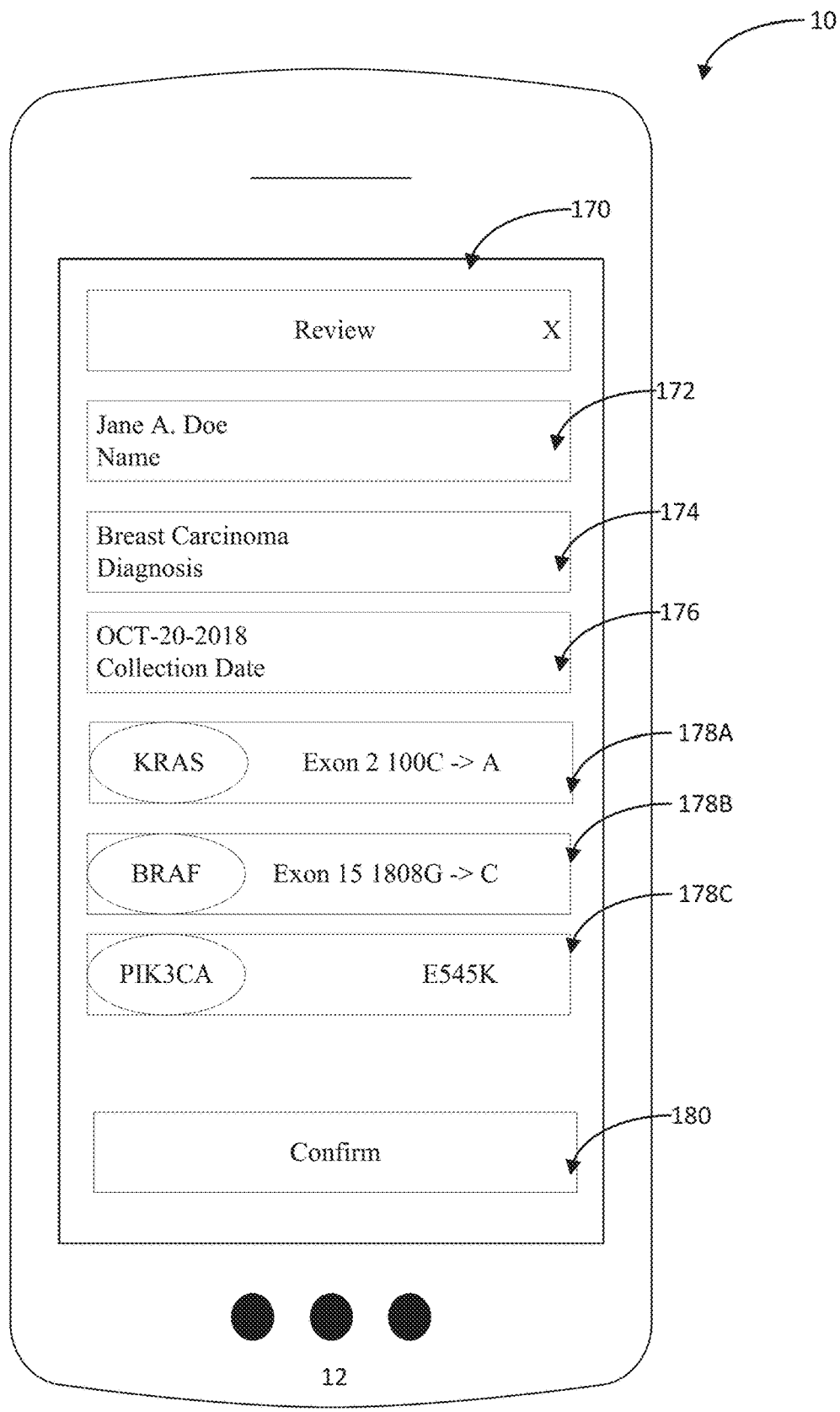
FIG. 16 is a depiction of a data verification screen of the application for verifying and/or editing data imported into the application and/or patient record as a result of data capture from one or more documents.

An exemplary natural language processing (NLP) algorithm may receive as an input, a region of the electronic document capture which has had optical character recognition (OCR) performed on the extracted region to identify if the text of the region corresponds to the value type expected in that extracted region where the mask was applied. For example, if the region was expected to provide treatment information, the NLP algorithm may attempt to classify the extracted text as treatment information based off of the NLP algorithm training data set. Furthermore, the patient information being extracted, such as patient name, diagnosis, treatment, or sequencing information, may be associated with a respective field in the application. Extracted patient information may then be populated into the mobile application for review by the user, as seen in FIG. 16 and as discussed in greater detail below. The user may correct any errors by selecting the data field in the application corresponding to the information. These errors may be stored and/or sent to a training engine to improve upon the extraction algorithms and techniques. The training engine may generate a new extraction algorithm to use in future extractions based from detected errors. More information is disclosed below with respect to FIGS. 8 and 11, below. For text based fields, a text editor/keyboard may be displayed for the user to provide text corrections. Additionally, suggested replacements may also appear in a dropdown list in addition to or in place of the text editor. For date based fields, a calendar may be displayed to select the correct date, or for diagnosis, a drop down featuring diagnoses supported by the document type, report type, or even the database may be enumerated for selection. The field types listed above are merely representative and are not intended to limit fields to the specific type of data associated in the above description, for example, date based fields may also be populated using text input. The predefined model that is associated with each of the templates may contain reference fields to identify each of the fields that may be extracted to generate the extracted patient information. For example, a feature corresponding to the informational header may have a corresponding field in the predefined model which lists a location the patient name is expected, a location the patient date of birth is expected, and a location of the diagnosis (such as cancer type) is expected as described above.

In an alternative embodiment, a MLA may receive as an input, a region of the electronic document capture which has had optical character recognition (OCR) performed on the extracted region to identify if the text of the region corresponds to the value type expected in that extracted region where the mask was applied. For example, if the region was expected to provide treatment information, the MLA may attempt to classify the extracted text as treatment information based off of the MLA training set. Furthermore, the patient information being extracted, such as a patient name, diagnosis, treatment, or sequencing information, may be associated with a respective field in the application. Extracted patient information may then be populated into the mobile user interface for review by the user. Other information that may be extracted may include: gene(s) (such as TP53, NF1, or PDL1); gene expression count information (such as over/under expressed or count values representing the number of times the expression occurs in sequencing); respective gene variants (such as Q192 or E496); gene variant calls (such as "4724+1G>A", "Q192*", or "c.380C>A"); depth of sequencing (such as occurrences of chromosome hits per number of DNA reads); scope of sequencing (such as panel type: whole genome or targeted panels); proteomics (such as protein based assertions: counts and shapes); epigenetics; RNA expressions (such as overexpression or under-expression); organoids (such as chemical/medical responses organoids experienced in a lab setting); germline (such as mutations present in healthy cell DNA); immunotherapies (such as engineered immune receptors such as CAR-T, cancer vaccines, checkpoint blockades, etc.); and tumor-normal (such as a comparison of RNA and/or DNA sequencing results of tumor tissue with RNA and/or DNA sequencing results of a non-tumor sample, such as non-tumor tissue, blood, or saliva). Features of the electronic data capture may also be directed to clinical trials, for example, by listing details associated with the name of the clinical trial, geographic location of the facilities administering the trial, treatments associated with the trial, inclusion/exclusion criteria for patients who may participate in the trial, and other relevant information.

Information that is extracted may be from various disease states and relate to various genes or locus/loci (a fixed position on a chromosome, such as the position of the gene or genetic marker). For instance, on a report providing genetic sequencing information that may help a clinician make a decision about which medication to prescribe for a patient's depression, the genes related to the information on the report may include one or more of CYP2C19, CYP2D6+DEL/DUP, CYP1A2, CYP2B6, CYP2C9, CYP3A4, HLA-A, HLA-B, HTR2A, SLC6A4, or UGT1A4. In other examples, the genes related to the information on the report may include one or more of 5HT2C, ABCB1 (MDR1), ABCG2, ACE, ADRA2A, ADRB1, ADRB2, AGT, ANKK1, ANK3, APOE, BDNF, CACNA1C, CES1, COMT, CYP3A5, CYP4F2, DPYD, DRD1, DRD2, DRD3, EDN1, ERCC1, FCGR2A, FCGR3A, F2, F5, G6PD, GNB3, GRIK1, GRIK4, GSTP1, HNF4A, HSD3B1, HTR2C, HTR1A, IFNL3, IL28B (IFNL4), KCNIP1, KCNJ11, KCNQ1, LDLR, LIPC, MC4R, MTHFR, MTRR, NEUROD1/BETA2, NQO1, NR1H3, NUDT15, OPRM1, PAX4, POLG, PPARA, PPARG2, PPARGC1A, PRKAA1, PRKAB2, PTPRD, RBP4, SLC6A2, SLC22A1 (OCT1), SLC22A2 (OCT2), SLC30A8, SLC49A4 (PMAT), SLC47A1 (MATE1), SLC47A2 (MATE2-K), SLCO1B1, SOD2, STK11, TCF7L2, TPMT, TYMS, UCP2, UGT1A1, UGT1A9, UMPS, or VKORC1.

In other examples, the genes related to the information on the report may include one or more of AATK, ABCA1, ABCB1, ABCB11, ABCB4, ABCC1, ABCC2, ABCG1, ABCG2, ABI1, ABL1, ABL2, ACE, ACSL6, ACTA2, ACTC1, ACVR1, ACVR1B, ACVR2A, ACVR2B, ADAM17, ADAMTS20, ADGRA2, ADGRB3, ADGRL2, ADGRL3, ADRB1, ADRB2, AFF1, AFF2, AFF3, AHR, AIP, AJUBA, AKAP9, AKT1, AKT2, AKT3, ALK, ALKBH6, ALOX12B, ALOX5, AMER1, APC, APEX1, APH1A, APOA1, APOB, AR, ARAF, AREG, ARFRP1, ARHGAP10, ARHGAP26, ARHGAP35, ARID1A, ARID1B, ARID2, ARID5B, ARNT, ARNT2, ARPC1A, ARPC1B, ARTN, ARX, ASCL1, ASCL2, ASCL3, ASCL4, ASCL5, ASH1L, ASH2L, ASPSCR1, ASXL1, ASXL2, ASXL3, ATAD2, ATAD2B, ATF1, ATM, ATR, ATRX, AURKA, AURKB, AURKC, AXIN1, AXIN2, AXL, B2M, BABAM1, BACH1, BACH2, BAG4, BAP1, BARD1, BAX, BAZ1A, BAZ1B, BAZ2A, BAZ2B, BBC3, BCAR3, BCL10, BCL11A, BCL11B, BCL2, BCL2A1, BCL2L1, BCL2L11, BCL2L2, BCL3, BCL6, BCL7A, BCL9, BCLAF1, BCOR, BCORL1, BCR, BDNF, BID, BIRC2, BIRC3, BIRC5, BIRC8, BLK, BLM, BLNK, BMI1, BMPR1A, BMPR1B, BMX, BPTF, BRAF, BRCA1, BRCA2, BRD1, BRD2, BRD3, BRD4, BRD7, BRD8, BRD9, BRDT, BRIP1, BRPF1, BRPF3, BRWD1, BRWD3, BTC, BTG1, BTG2, BTG3, BTK, BTRC, BUB1, BUB1B, BUB3, CACNA1C, CACNA1S, CACNB2, CADM2, CALR, CAMTA1, CAPRIN2, CARD10, CARD11, CARD6, CARD8, CARM1, CASC11, CASP8, CBFA2T2, CBFA2T3, CBFB, CBL, CBLB, CBLC, CBX1, CBX2, CBX3, CBX4, CBX5, CBX6, CBX7, CBX8, CCDC6, CCNB3, CCND1, CCND2, CCND3, CCNE1, CCNE2, CCNL1, CD1D, CD22, CD274, CD276, CD28, CD40, CD40LG, CD44, CD70, CD79A, CD79B, CD80, CD86, CDC14A, CDC20, CDC25A, CDC25B, CDC25C, CDC42, CDC6, CDC73, CDH1, CDH10, CDH11, CDH2, CDH20, CDH3, CDH5, CDH7, CDK1, CDK10, CDK11A, CDK11B, CDK12, CDK13, CDK14, CDK15, CDK16, CDK17, CDK18, CDK19, CDK2, CDK20, CDK3, CDK4, CDK5, CDK6, CDK7, CDK8, CDK9, CDKN1A, CDKN1B, CDKN1C, CDKN2A, CDKN2B, CDKN2C, CDKN3, CDX1, CDX2, CEBPA, CEBPB, CEBPD, CEBPE, CEBPG, CEBPZ, CECR2, CENPE, CES1, CES2, CHD1, CHD1L, CHD2, CHD3, CHD4, CHD5, CHD6, CHD7, CHD9, CHEK1, CHEK2, CHIC1, CHIC2, CHUK, CIC, CIITA, CKS1B, CKS2, CLIP1, CMPK1, CNKSR1, CNOT3, CNTFR, COL3A1, COMT, COPS3, CRBN, CREB1, CREB3L1, CREB3L2, CREB3L4, CREBBP, CREM, CRHR1, CRK, CRKL, CRLF2, CRTC1, CRTC2, CRTC3, CSF1, CSF1R, CSF2RA, CSF2RB, CSF3R, CSK, CSNK1D, CSNK1E, CTCF, CTCFL, CTLA4, CTNNA1, CTNNA2, CTNNA3, CTNNB1, CTNND1, CTSD, CTSL, CTSS, CUL3, CUL4A, CUL4B, CUX1, CPLD, CYP17A1, CYP1A2, CYP21A2, CYP2A6, CYP2B6, CYP2C19, CYP2C8, CYP2C9, CYP2D6, CYP2J2, CYP2R1, CYP3A4, CYP3A5, CYP4F2, DACH1, DACH2, DAXX, DBH, DCC, DCUN1D1, DCUN1D2, DDB2, DDIT3, DDR1, DDR2, DDX3X, DDX5, DDX6, DEK, DHFR, DHH, DIAPH1, DIAPH2, DIAPH3, DICER1, DIRAS3, DIS3, DKC1, DMXL1, DNM2, DNMT1, DNMT3A, DNMT3B, DNMT3L, DOCK2, DOT1L, DPYD, DRD1, DRD2, DSC2, DSG2, DSP, DUSP22, DVL1, DVL2, DVL3, DYRK2, E2F1, E2F3, E2F5, E2F6, E2F7, EBF1, ECT2L, EED, EGF, EGFR, EGR1, EGR2, EHF, EHMT1, EHMT2, EIF1AX, ELANE, ELF1, ELF2, ELF3, ELF4, ELF5, ELK1, ELK3, ELK4, ELP3, EML4, EMSY, EP300, EPCAM, EPGN, EPHA1, EPHA2, EPHA3, EPHA4, EPHA5, EPHA6, EPHA7, EPHA8, EPHB1, EPHB2, EPHB3, EPHB4, EPHB6, EPOR, ERBB2, ERBB3, ERBB4, ERCC1, ERCC2, ERCC3, ERCC4, ERCC5, EREG, ERF, ERG, ESCO1, ESCO2, ESPL1, ESR1, ESR2, ESRRA, ETS1, ETS2, ETV1, ETV2, ETV3, ETV3L, ETV4, ETV5, ETV6, ETV7, EWSR1, EXT1, EXT2, EXTL1, EZH1, EZH2, FADD, FAM175A, FAM46C, FANCA, FANCB, FANCC, FANCD2, FANCE, FANCF, FANCG, FANCI, FANCL, FANCM, FAS, FASLG, FAT1, FAT2, FAT3, FAT4, FBN1, FBXO11, FBXO8, FBXW11, FBXW7, FEN1, FER, FES, FEV, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, FGFR1, FGFR2, FGFR3, FGFR4, FGR, FH, FHIT, FIGF, FKBP10, FKBP5, FKBP9, FLCN, FLI1, FLT1, FLT3, FLT3LG, FLT4, FOLH1, FOS, FOSB, FOSL1, FOSL2, FOXA1, FOXA2, FOXA3, FOXG1, FOXL1, FOXL2, FOXM1, FOXN3, FOXO1, FOXO3, FOXO4, FOXP1, FOXP2, FOXP3, FOXP4, FOXQ1, FRK, FRS2, FRS3, FSHR, FUBP1, FUS, FYN, FZR1, G6PC3, G6PD, GAB1, GAB2, GABPA, GALNT12, GATA1, GATA2, GATA3, GATA5, GATA6, GDNF, GFI1, GFI1B, GFRA4, GGCX, GHR, GID4, GLA, GLCCI1, GLI1, GLI2, GLI3, GLIS1, GLIS2, GLIS3, GNA11, GNA13, GNAQ, GNAS, GNRHR, GOT1, GPC3, GPC5, GPS2, GRB10, GRB2, GRB7, GREM1, GRIN2A, GRK4, GRK5, GRM3, GRM8, GSK3A, GSK3B, GSTT1, GTPBP4, GUCY1A2, H3F3A, HAX1, HBEGF, HCK, HDAC1, HDAC10, HDAC11, HDAC2, HDAC3, HDAC4, HDAC5, HDAC6, HDAC7, HDAC8, HDAC9, HDGF, HELLS, HES1, HES2, HES4, HEY1, HEY2, HGF, HIF1A, HIF1AN, HIST1H1E, HIST1H3B, HIST1H4E, HLA-A, HLA-B, HLF, HLTF, HMGA1, HMGA2, HMGCR, HNF1A, HNF1B, HNRNPA3, HOXA10, HOXA11, HOXA13, HOXA3, HOXA9, HOXB13, HOXB3, HOXC10, HOXC11, HOXC13, HOXD10, HOXD11, HOXD13, HOXD3, HOXD4, HR, HRAS, HSD11B2, HSD3B1, HSP90AA1, HSP90AB1, HSPBAP1, HTR1A, HTR2A, ICK, ICOS, ICOSLG, ID1, ID2, ID3, ID4, IDH1, IDH2, IFNLR1, IGF1, IGF1R, IGF2, IGF2R, IHH, IKBIP, IKBKAP, IKBKB, IKBKE, IKZF1, IKZF2, IKZF3, IL10RA, IL10RB, IL11RA, IL12RB1, IL12RB2, IL13RA1, IL15RA, IL17RA, IL17RB, IL17RC, IL18R1, IL18RAP, IL1R1, IL1R2, IL1RAP, IL20RA, IL20RB, IL21R, IL22RA1, IL22RA2, IL23R, IL2RA, IL2RB, IL2RG, IL3, IL3RA, IL4R, IL5RA, IL6R, IL6ST, IL7R, IL9R, ING1, ING4, INHBA, INPP4B, INSR, INSRR, INTS12, IQGAP1, IQGAP2, IQGAP3, IRAK1, IRF4, IRF5, IRF6, IRS1, IRS2, IRS4, ITK, ITPKB, JADE1, JAK1, JAK2, JAK3, JARID2, JAZF1, JMJD1C, JMJD4, JMJD6, JMJD7, JMJD8, JUN, JUNB, JUND, JUP, KAT2A, KAT2B, KAT5, KAT6A, KAT6B, KAT7, KATE, KCNH2, KCNJ5, KCNQ1, KDM1A, KDM1B, KDM2A, KDM2B, KDM3A, KDM3B, KDM4A, KDM4B, KDM4C, KDM4D, KDM5A, KDM5B, KDM5C, KDM5D, KDM6A, KDM6B, KDM7A, KDM8, KDR, KDSR, KEAP1, KEL, KHSRP, KIF1B, KIT, KITLG, KLF12, KLF4, KLF5, KLF6, KLF8, KMT2A, KMT2B, KMT2C, KMT2D, KMT2E, KRAS, LATS1, LATS2, LCK, LDB1, LDLR, LEF1, LEPR, LGR4, LGR5, LGR6, LHCGR, LIFR, LMNA, LMO1, LMO2, LMO7, LMTK2, LMTK3, LPP, LRP1B, LRP5, LRP6, LRRK2, LSM1, LTK, LYL1, LYN, LZTR1, MAD1L1, MAD2L1, MAD2L2, MAF, MAFB, MAGED1, MAGI2, MAK, MALT1, MAML1, MAML2, MAML3, MAMLD1, MAOA, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K15, MAP3K19, MAP3K2, MAP3K3, MAP3K4, MAP3K5, MAP3K6, MAP3K7, MAP3K8, MAP3K9, MAP4, MAP4K1, MAP4K2, MAP4K3, MAP4K4, MAP4K5, MAPK1, MAPK10, MAPK11, MAPK12, MAPK13, MAPK14, MAPK15, MAPK3, MAPK4, MAPK6, MAPK7, MAPK8, MAPK9, MAST1, MAST2, MATK, MAU2, MAX, MBD1, MBD3, MC1R, MCL1, MCPH1, MDM2, MDM4, MDS2, MECOM, MED12, MED12L, MED29, MEF2B, MEN1, MERTK, MET, MGA, MGMT, MID1, MINK1, MIPOL1, MITF, MKL1, MKL2, MLF1, MLH1, MLH3, MLLT1, MLLT10, MLLT11, MLLT3, MLLT6, MLST8, MN1, MNX1, MOB1A, MOB1B, MOS, MPG, MPL, MRE11A, MSH2, MSH3, MSH4, MSH6, MSI2, MST1, MST1R, MTAP, MTCP1, MTDH, MTOR, MUSK, MUTYH, MXD1, MYB, MYBL1, MYBL2, MYBPC3, MYC, MYCL, MYCN, MYD88, MYH11, MYH7, MYL2, MYL3, MYLK, MYOD1, NA, NAB1, NAB2, NAT2, NBN, NCK1, NCK2, NCOA1, NCOA2, NCOA3, NCOA4, NCOR1, NCOR2, NCSTN, NDRG1, NEK1, NEK10, NEK11, NEK2, NEK3, NEK4, NEK5, NEK6, NEK7, NEK8, NEK9, NF1, NF2, NFATC1, NFATC2, NFATC3, NFATC4, NFE2L2, NFIA, NFIB, NFIC, NFIX, NFKB1, NFKB2, NFKBIA, NFKBIB, NFKBID, NFKBIE, NFKBIZ, NGF, NHP2, NIPBL, NKX2-1, NKX2-2, NKX2-3, NKX2-4, NKX2-5, NKX2-6, NKX2-8, NKX3-1, NKX3-2, NLRP1, NOD2, NONO, NOP10, NOTCH1, NOTCH2, NOTCH2NL, NOTCH3, NOTCH4, NPM1, NPPB, NPR1, NQO1, NR0B1, NR3C1, NR3C2, NR4A1, NR4A2, NR4A3, NRAS, NRG1, NRG2, NRG3, NRG4, NRIP1, NRTN, NSD1, NT5C2, NTF3, NTF4, NTRK1, NTRK2, NTRK3, NUMB, NUMBL, NUP214, NUP93, NUP98, NUTM1, NUTM2A, NUTM2B, NUTM2F, NUTM2G, ODC1, OLIG2, OSMR, PAK1, PAK2, PAK3, PAK4, PAK6, PAK7, PALB2, PALLD, PARK2, PARP1, PARP2, PARP4, PATZ1, PAX1, PAX2, PAX3, PAX4, PAX5, PAX6, PAX7, PAX8, PAX9, PAXIP1, PBRM1, PBX1, PBX2, PBX3, PBX4, PCBP1, PCSK9, PDCD1, PDCD1LG2, PDGFA, PDGFB, PDGFC, PDGFD, PDGFRA, PDGFRB, PDK1, PDPK1, PDS5A, PDS5B, PEAR1, PEG3, PERP, PGF, PGR, PHB, PHF1, PHF2, PHF6, PHF8, PHIP, PHLPP1, PHLPP2, PHOX2A, PHOX2B, PICALM, PIK3C2A, PIK3C2B, PIK3C2G, PIK3C3, PIK3CA, PIK3CB, PIK3CD, PIK3CG, PIK3R1, PIK3R2, PIK3R3, PIK3R4, PIM1, PIM2, PIM3, PKHD1, PKP2, PLA2G2A, PLAG1, PLAGL1, PLAGL2, PLCG1, PLCG2, PLK1, PLK2, PLK3, PLK4, PMAIP1, PML, PMS1, PMS2, PNRC1, POLD1, POLE, POR, POT1, POU2AF1, POU2F2, POU5F1, POU5F1B, POU5F2, POU6F1, POU6F2, PPARA, PPARD, PPARG, PPFIA1, PPM1D, PPP1R1C, PPP2R1A, PPP2R1B, PPP2R2B, PPP6C, PRCC, PRDM1, PRDM10, PRDM11, PRDM12, PRDM13, PRDM14, PRDM15, PRDM16, PRDM2, PRDM4, PRDM5, PRDM6, PRDM7, PRDM8, PRDM9, PREX2, PRF1, PRKACA, PRKACB, PRKAG2, PRKAR1A, PRKAR1B, PRKCI, PRKD1, PRKDC, PRLR, PRMT1, PRMT2, PRMT3, PRMT5, PRMT6, PRMT7, PRMT8, PRPF40B, PRPF6, PRRX1, PRRX2, PRSS1, PRSS3, PRSS8, PSEN1, PSEN2, PSENEN, PSIP1, PSPN, PTCH1, PTCH2, PTEN, PTGIS, PTGS1, PTGS2, PTK2, PTK2B, PTK6, PTK7, PTPN11, PTPN2, PTPN21, PTPN6, PTPRB, PTPRC, PTPRD, PTPRF, PTPRG, PTPRJ, PTPRK, PTPRM, PTPRQ, PTPRR, PTPRT, PTTG1, PVT1, RAB23, RAB25, RABEP1, RAC1, RAC2, RAD21, RAD50, RAD51, RAD51AP1, RAD51B, RAD51C, RAD51D, RAD52, RAD54B, RAD54L, RAF1, RAP1GDS1, RARA, RARB, RARG, RASA1, RB1, RBM10, RBM14, RBM15, RBMX, RBMXL1, RBMXL2, RBPJ, REC8, RECQL4, REL, RELA, RELB, RET, RHEB, RHOA, RHOB, RHOH, RHOT1, RICTOR, RIPK1, RIPK2, RIPK3, RIPK4, RIT1, RNF213, RNF40, RNF43, ROBO2, ROCK1, ROCK2, ROR1, ROR2, ROS1, RPA1, RPL5, RPN1, RPS6KB1, RPS6KB2, RPTOR, RRM1, RSPO2, RSPO3, RUNX1, RUNX1T1, RUNX2, RUNX3, RUVBL1, RXRA, RYK, RYR1, RYR2, SAMD9, SAV1, SBDS, SCN5A, SDHA, SDHAF2, SDHB, SDHC, SDHD, SET, SETBP1, SETD1A, SETD1B, SETD2, SETD3, SETD4, SETD5, SETD6, SETD7, SETD8, SETD9, SETDB1, SETDB2, SETMAR, SF1, SF3A1, SF3B1, SFPQ, SFRP1, SGK1, SGOL1, SGOL2, SH2B3, SH2D1A, SH3GL1, SHB, SHC1, SHC2, SHC3, SHC4, SHFM1, SHH, SHOC2, SKI, SKIL, SKOR1, SKP2, SLC15A2, SLC19A1, SLC22A1, SLC22A2, SLC22A3, SLC22A6, SLC26A3, SLC47A1, SLC47A2, SLC6A3, SLC6A4, SLCO1A2, SLCO1B1, SLCO1B3, SLCO2B1, SLIT2, SLX4, SMAD1, SMAD2, SMAD3, SMAD4, SMAD5, SMAD6, SMAD7, SMAD9, SMARCA1, SMARCA2, SMARCA4, SMARCA5, SMARCB1, SMARCC1, SMARCD1, SMARCD2, SMARCD3, SMARCE1, SMC1A, SMC1B, SMC2, SMC3, SMC4, SMC5, SMC6, SMCHD1, SMO, SMURF1, SMURF2, SMYD1, SMYD2, SMYD3, SMYD4, SMYD5, SOCS1, SOS1, SOS2, SOX1, SOX10, SOX17, SOX2, SOX21, SOX3, SOX8, SOX9, SP100, SP110, SP140, SP140L, SP3, SPDEF, SPEN, SPI1, SPIB, SPIC, SPOP, SPOPL, SPRED1, SPRED2, SPRED3, SPRY2, SPRY3, SRC, SRGAP3, SRMS, SRSF2, SS18, SS18L1, SSTR1, SSTR2, SSTR3, SSTR4, SSTR5, SSX1, SSX2, SSX3, SSX4, STAG1, STAG2, STARD3, STAT1, STAT2, STAT3, STAT4, STAT5A, STAT5B, STATE, STK11, STK19, STK3, STK36, STK4, STYK1, SUFU, SULT1A1, SUV39H1, SUV39H2, SUV420H1, SUV420H2, SUZ12, SYK, SYNE1, TAF1, TAF15, TAF1L, TAL1, TAL2, TAOK1, TAOK2, TAOK3, TBC1D12, TBL1X, TBL1XR1, TBP, TBX18, TBX2, TBX22, TBX3, TBXAS1, TCEB1, TCF12, TCF3, TCF4, TCF7, TCF7L1, TCF7L2, TCL1A, TCL1B, TEAD1, TEAD2, TEAD3, TEAD4, TEC, TEF, TEK, TENM2, TERC, TERF1, TERT, TET1, TET2, TET3, TFE3, TFEB, TFEC, TFG, TGFA, TGFB1, TGFB2, TGFBR1, TGFBR2, THPO, TIE1, TINF2, TLK1, TLK2, TLR1, TLR10, TLR2, TLR4, TLR5, TLR6, TLR7, TLR8, TLR9, TLX1, TLX2, TLX3, TMC6, TMC8, TMEM127, TMEM43, TMPRSS2, TNFAIP3, TNFRSF14, TNFRSF17, TNK1, TNK2, TNKS, TNKS2, TNNI3, TNNT2, TOP1, TOP2A, TOP2B, TP53, TP53BP1, TP63, TPM1, TPMT, TPTE, TPTE2, TRAF1, TRAF2, TRAF3, TRAF3IP1, TRAF3IP2, TRAF3IP3, TRAF6, TRAF7, TRIB1, TRIB2, TRIB3, TRIM24, TRIM28, TRIM33, TRIM66, TRIO, TRRAP, TSC1, TSC2, TSHR, TSHZ3, TWIST1, TWIST2, TXK, TYK2, TYRO3, U2AF1, U2AF2, UBE2D1, UBE2D2, UBE2D3, UBE2D4, UBE4A, UBR5, UGT1A1, UGT1A4, UHRF1, UHRF2, USB1, USP9X, USP9Y, UTY, VAV1, VAV2, VAV3, VDR, VEGFA, VEGFB, VEGFC, VGLL1, VGLL2, VGLL3, VGLL4, VHL, VHLL, VKORC1, VTCN1, WAPL, WAS, WASL, WHSC1, WHSC1L1, WIF1, WISP1, WNK1, WNK2, WNK3, WNK4, WNT1, WNT10A, WNT10B, WNT11, WNT16, WNT2, WNT2B, WNT3, WNT3A, WNT4, WNT5A, WNT5B, WNT6, WNT7A, WNT7B, WNT8A, WNT8B, WNT9A, WNT9B, WRN, WT1, WWTR1, XBP1, XIAP, XIRP2, XPA, XPC, XPO1, XRCC2, YAP1, YEATS4, YES1, YWHAB, YWHAE, YWHAH, YWHAQ, YWHAZ, YY1, ZAP70, ZBTB16, ZBTB20, ZBTB33, ZBTB5, ZBTB7B, ZC3H12A, ZC3H12D, ZC3H7B, ZCCHC7, ZEB2, ZFHX3, ZMYM3, ZMYND11, ZMYND8, ZNF217, ZNF384, ZNF423, ZNF444, ZNF471, ZNF521, ZNF607, ZNF639, ZNF668, ZNF703, ZNF704, ZNF750, ZNRF3, or ZRSR2. In other examples, the genes related to the information on the report may include one or more of genes sequenced in a whole exome panel, which is a panel that sequences the whole exome. In other examples, the genes related to the information on the report may include one or more of the genes sequenced in a whole genome panel, which is a panel that sequences the whole genome.

For each feature, the list of fields may be retrieved from the predefined model and candidate extraction may be performed according to the expected field. Each candidate that is extracted using the methods detailed above may have a confidence value identifying an estimated accuracy of the result. In some circumstances, a high level of confidence may not be available. When a level of certainty lies below a threshold value (such as less than 90%), the MLA may output the highest entry with the highest level of certainty calculated identifying, for example, a 60% confidence male and 40% confidence female. In another embodiment, no prediction may be generated when the confidence value is below the threshold and the user may be required to manually populate the associated field in the application.

Extracted candidate concepts may be processed to identify any links between the concepts and known entities, for example, the enumerated list of medical drugs discussed above. Entity linking is the task of determining whether a candidate concept (phrase) is a relevant clinical concept. Relevancy may be determined by the presence of the candidate concept in a medical dictionary. Fuzzy matching may be implemented by an approximate string matching algorithm. For example, in conventional string matching, a string must exactly match, character for character, with a reference string in order to yield a positive match result. In fuzzy string matching a string is still matched character by character; however, for each mismatch in character, operations may be performed to elicit a match. For example, a mismatching character may be deleted, and the next character considered for a hit, which would account for having an extraneous character in a word, a character may be inserted at the mismatching character to provide a match to allow a match to occur even if a character was omitted, a character may be substituted at the mismatching character to allow a match even if the wrong character was inserted, or a character may be transposed at the mismatching character. For each mismatch operation that is performed, a counter may increment to track the number of errors allowed. In an embodiment, the number of errors may be capped to restrict the flexibility of the fuzzy searching algorithm, for example, only three mismatch corrections may be allowed before no match may be identified during processing. Other embodiments may adjust the threshold based upon the length of the word to allow longer words more mismatches than shorter words. For example, if a three letter word is allowed three mismatch operations, then a fuzzy string matching algorithm may generate matches for thousands of concepts from 1-6 characters.

Fuzzy matching is structured around the text concepts included in the medical dictionary and may be applied on a word-by-word basis rather than a letter-by-letter basis. For example, a concept candidate may include the phrase "needle biopsy." An entity matching search may identify entities linked to, for example an exact match "needle biopsy", a reordered match "biopsy needle", or phrase matches of "needle aspiration biopsy of lung" or "breast needle biopsy." Such entity matches may be derived using the same fuzzy matching operations above (deletion, insertion, transcription, etc.), but on the whole word rather than each individual character. Furthermore, in still another embodiment, both fuzzy matching on a character by character basis and word by word basis may be applied concurrently to generate entity matches.

Certain features, such as the TNM Classification of Malignant Tumors (TNM) or genetic variant/mutation results, may be preempted from fuzzy matching because the sequence of the characters are important and any rearrangement or replacement (fuzzy matching) to generate a match may cause the incorrect concept to be matched.

Matched concepts may be normalized to ensure that the concepts that are matched are consistent with the concepts archived in the database (described below in more detail). For example, in a cancer type normalization, there may be numerous candidate matches which reference breast cancer in one form or another that match. A post-processing step to the normalization may be applied which identifies, for example, when a cancer site is designated as breast, and adjusts the final result such that all entries with a breast cancer site share the same cancer site code and same spelling "breast". Other normalized results may include each main cancer site, such as brain, lung, liver, ovary, or bone marrow, a predetermined catch-all for unknown sites, or known codes which are irrelevant and may be filtered.

With regard to both the post-processing of scanned documents discussed above, as well as the analysis and structuring of other aspects of patient EHRs or EMRs, such as next-generation sequencing reports, a system that identifies and processes information in clinical documents or other records is disclosed herein. The system may use a combination of text extraction techniques, text cleaning techniques, natural language processing techniques, machine learning algorithms, and medical concept (Entity) identification, normalization, and structuring techniques. The system also maintains and utilizes a continuous collection of training data across clinical use cases (such as diagnoses, therapies, outcomes, genetic markers, etc.) that help to increase both accuracy and reliability of predictions specific to a patient record. The system accelerates a structuring of clinical data in a patient's record. The system may execute subroutines that highlight, suggest, and pre-populate an electronic medical record ("EHR" or "EMR"). The system may provide other formats of structured clinical data, with relevant medical concepts extracted from the text and documents of record.

The system may include a persistent, stateless service that receives a plurality of queued messages from one or more peripheral services (such as a file conversion service or an optical character recognition service) which may also perform natural language processing (NLP) operations on outputs of those peripheral services. Those NLP operations include machine learning features, as described herein, in order to increase the speed, efficiency, and accuracy of the processing. A persistent, stateless system is a system operating in an asynchronous manner in comparison to a conventional point to point pipeline. For example, the system may be structured in a "pipeline" fashion, but each modular component of the system may retrieve and store exemplary input/output datasets as they become available, without relying on the modular component before or after in the pipeline to initiate or acknowledge availability for a transfer. Such statelessness allows for more advanced parallelization because it reduces inefficiencies at each bottleneck of the pipeline (handshaking to pass data). More detail on the persistent, stateless service is discussed with reference to FIG. 5 below.

The system may include a training service designed to promote user interaction to improve machine learning capabilities. In one aspect, the training service may use a production repository as its input data. In another aspect, the training service may use a data repository separate from the production repository. Additionally, the system may operate in a plurality of manners. In a first manner, the system may be triggered in response to specific queries requesting processing on specific EHR or EMR files. In a second manner, the system may include a backend service that reviews and processes EHR or EMR files continuously (without a need for specific user queries). The backend service may operate asynchronously from user input, such as queries or commands. In such a manner, the system may detect when a patient record has been received, either partially or in full, and begin processing the patient record in aggregate or as a whole to determine relevant medical concepts for entry into the EMR.

In the field of clinical abstraction from EHR and EMR documents, machine learning or deep learning may be combined with NLP techniques to abstract relevant medical concepts. While the detailed implementations of these are disclosed in more detail below, an exemplary abstraction performed on a simple text is now provided to give a general understanding of one aspect of the disclosure. For instance, the simple text "The patient was given Tylenol 50 mg at 10:35 am." may be analyzed using a machine learning algorithm (MLA) trained on EHR and EMR documents relating to thousands of patients to recognize medications that the patient was prescribed in order to generate the table 52 of FIG. 6, where the MLA may be the same or a different MLA from the one discussed above.

Generating a training set from which to train the MLA involves both enumerating known drugs (which may include thousands or even tens of thousands of drugs) and also maintaining the flexibility to recognize drugs which are not included in the sources of the known drugs. The process of enumerating the known drugs into a list may include identifying clinical drugs prescribed by healthcare providers, pharmaceutical companies, and research institutions. Such providers, companies, and institutions may provide reference lists of their drugs. For example, the US National Library of Medicine (NLM) publishes a Unified Medical Language System (UMLS) including a Metathesaurus having drug vocabularies including CPT®, ICD-10-CM, LOINC®, MeSH®, RxNorm, and SNOMED CT®. Each of these drug vocabularies highlights and enumerates specific collections of relevant drugs. Other institutions such as insurance companies may also publish clinical drug lists providing all drugs covered by their insurance plans. By aggregating the drug listings from each of these providers, companies, and institutions, an enumerated list of clinical drugs that is universal in nature may be generated.

A combination of NLP and supervised, semi-supervised, or unsupervised MLA techniques may be used to generate an intelligent training set of data to recognize entries from the enumerated list of clinical drugs, in order to identify patterns within the text of abstracted documents which typically surround drug entries. The identified patterns may then be applied to unknown drugs to generate new entries which are added to the clinical drug list. An exemplary pattern may be a sentence structure containing "patient was given _____" or "patient was prescribed _____." In these examples, the known drugs are the supervised portion of the semi-supervised algorithm while the new entries determined are the unsupervised portion of the semi-supervised algorithm. In this manner, a non-exhaustive listing of drugs may be leveraged to train a MLA to detect drugs based on sentence structure, associated key terms, or other patterns in the text. Once trained, the unsupervised portion of the semi-supervised algorithm will apply the training to detect unclassified words for addition to the classification list. In this manner, a semi-supervised MLA can apply features of NLP to detect and classify unknown and known drug entries in medical texts. While described herein with respect to the medical concept of a drug, this approach may be applied to all medical concept classifications using the techniques described herein. Specific details of the NLP and MLA techniques are discussed in more detail with respect to FIGS. 3 and 7-10, below. Specific details of supervised, semi-supervised, or unsupervised MLA techniques are discussed in more detail below.

As discussed above, medical data may include numerous fields including, but not limited to, patient demographics, clinical diagnoses, treatments and outcomes, and genetic testing and laboratory information, and each of the fields may also have a plurality of subfields. The above provided examples, enumerations, and lists are not intended to limit the scope of the available fields and are intended to convey only the nature and structure that fields within medical data may be represented within a universal EMR. These fields of medical data may also identify concept candidates, discussed in more detail below with respect to FIGS. 3 and 7-10. For example, Tylenol may be a concept candidate relating to medication in treatment and outcomes.

Returning to FIG. 6, the sentence "The patient was given Tylenol 50 mg at 10:35 am." in a document dated Jan. 1, 2001, may be encoded field-by-field into the table 52 by identifying and populating one or more fields of:

Text: The entirety of the text ("The patient was given Tylenol 50 mg at 10:35 am.").

Medication: Identifying any medication mentioned in the text (Tylenol). Medications may be brand name or generic name. This field does not include information about the dosage or method of administration.

Active Ingredient: Identifying the active ingredients (acetaminophen) of the medication mentioned using a list such as a search table linking drug names to their active ingredients.

Dosage & Dosage Units: The dosage (50 mg) associated with the medication mentioned. In the above example, identifying that the dosage as 50 mg is fairly straightforward by reading the sentence, but clinical data is often printed in tables with a variety of structures that are not easy to infer. As such, normalizing the dosage and dosage units by separating value 50 into the dosage field and string "mg" or by selecting a known value entry for the milligram units within a list may be preferable.

Document & Page: The document and page where the text is found (Progress Note 01_01_01.pdf and page 3).

UMLS_CUI: The Concept Unique Identifier (CUI) field (C1234567) of the UMLS entry corresponding to the medication. The UMLS is a list of medical concepts (described in more detail with respect to FIG. 3, below) and the UMLS_CUI refers to the CUI field, which is UMLS' universal identifier. UMLS is comprised of a number of independently maintained clinical dictionaries and ontologies (such as those for cancer diagnosis & treatment, dentistry, veterinarian medicine, etc.). That is, the CUIs are universal to UMLS, such as there is only one CUI for Tylenol across all of its constituent dictionaries that enables UMLS to unite all of these disparate sources.

UMLS_AUI: The Atom Unique Identifier (AUI) field (RXNORM #12345) is the dictionary-specific identifying code of the UMLS. Where the CUI is universal, and has the same entry across all included sources, the AUI for Tylenol will have different AUIs for each dictionary that it has an entry in.

In one instance, the above fields, both the plurality of features 54 and their respective feature classifications 56 may be populated by a data analyst with sufficient medical knowledge and access to the requisite databases. Such an analyst may apply their education and experiences in the field of medicine to identify any medications administered despite confounding factors present in the text (such as shorthand, typos, obscure references), their dosage, and understand the integration of the two in the provided text. However, analysts are constrained by their human limits. Actions such as locating the data, opening it up in either a physical or digital format, reading through documents of 100s or 1000s of pages, etc., all require considerable time. Furthermore, the companies and institutions which hire analysts must invest in considerable financial expenses to hire, train, and maintain teams of analysts. Incorporating a combination of machine learning algorithms (MLA) and natural language processing (NLP) algorithms into this process may substantially improve the efficiency of the analysts or replace them altogether. The MLA and NLP algorithms will be discussed in more details with respect to FIGS. 3 and 6-10, below. Before text may pass through the multiple layers of MLA and NLP algorithms, it must be extracted from the documents using optical character recognition (OCR) and cleaned up through a variety of pre-processing steps.

Returning now to FIG. 5, a high level overview of an exemplary processing pipeline 60 is provided. An exemplary Intake Pipeline 62 may be configured to perform the following processing steps: 1. OCR, 2. Pre-processing, 3. Sentence Splitting, 4. Candidate Extraction, 5. Entity Linking, 6. Entity Normalization, and 7. Entity Structuring. Specifically, and with reference to FIG. 5, pipeline stage 64 for pre-processing may include OCR and text cleaning, stage 66 for parsing may include NLP algorithms for sentence splitting and candidate extraction, stage 68 for dictionary lookups may include entity linking, stage 70 for normalization may include entity normalization, stage 72 for structuring may include entity structuring, and stage 74 for post-processing may include structuring the data and formatting it into a universal EMR or institution based EMR format. Due to the asynchronous and modular nature of the pipeline stages, each stage may pass data directly to the next stage based on processing availability or may store data in a corresponding portion of a storage component or database. In an exemplary embodiment, a sentence splitting algorithm may be stored in a cloud based server or on a local/remote server 76 and may be incorporated into the parser at stage 66, a fuzzy matching algorithm 78 may be incorporated into the dictionary lookup at stage 68 and an Ontological graphing algorithm 80 may be incorporated into the normalization at stage 70.

For example, upon receiving a record update or a request in the form of a clinical document, a database of multiple documents, or another form of patient record, the request may pass through a pre-processing subroutine 82, a parsing subroutine 84, a dictionary lookup subroutine 86, a normalization subroutine 88, a structuring subroutine 90 for filtering and/or ranking, and a post-processing subroutine 92 in order to generate and serve a response to a remainder of the system. The first four of these subroutines may encompass a first layer, in which the system identifies and structures clinical concepts with corresponding metadata (clinical or medical concepts) extracted from clinical documents.

The intake pipeline 62 receives a clinical document that may include machine readable text or that may be received as an image file. If necessary, the document may be submitted to a pre-processor stage 64 that performs text cleaning and error detection (format conversion, resolution conversion, batch sizing, text cleaning, etc.). Once pre-processed, the document may be submitted for OCR on the document to convert the text into a machine-readable format (text document, html, etc.). Once in a machine-readable format, the error correction (such as spell checking, noise removal, context based correlation, etc.) may be performed on the now-machine-readable text. The intake pipeline stages 64-70 are modular components, which allows for real-time selection of the best processing tools and software depending on the type of document and document content being processed, enabling the processing pipeline to replace/compare algorithms used as necessary. Two examples of OCR software that may be used include Tesseract and Google Cloud Vision API. Tesseract provides high-speed OCR for documents which do not have any artifacting/noise (documents that have been printed to PDF or that had very little noise generated during the scanning process). Google Cloud Vision API, conversely, may be used for documents which have too much noise, as it is well-suited to process old documents or images of documents that have been scanned/faxed many times, introducing extensive artifacting and noise into the image. As a result, Cloud Vision may provide detailed information about the position of paragraphs, words, and documents within the documents processed. Other OCR systems may also be utilized in lieu of or in combination with the two described above.

The modularity of each processing stage requires different pre-processing mechanisms for each OCR service/software implemented. For example, different OCR services support some image formats and resolutions for OCR but may not support others. When processing patient records, many document formats included within the record are unsupported, and may require format conversion from the unsupported format to a supported format, as well as additional processing for parameter optimization for each respective document to achieve the best results from the OCR service selected, as discussed above. For example, when utilizing Google Cloud Vision, images may need to be format-converted to 300 dpi JPG files. Furthermore, Google Cloud Vision API charges for OCR on a per-request basis, but supports requests of up to 4 MB and supports batch requests (as many images as can be fit into one 4 MB request) for no extra cost. Additional processing may be performed to include additional document images into a request to place each request at the maximum file size and use batch processing to decrease costs.

Documents received at the pre-preprocessing stage may be in various text formats (such as DOC, DOCX, RTF, or as values in a spreadsheet/database). For simple documents, pre-processing may be performed by simply extracting any text directly (such as TXT, RTF, etc.), but some require advanced software to parse the file formats (such as DOCX, PDF, ACCDB). Exemplary software for parsing more complex file formats include pandoc and PDFBox.

As with the OCR steps discussed above, in another embodiment, additional pre-processing may be performed after submitting an image to OCR to determine whether the detected text is "reasonable" before outputting final results. While some OCR technologies may perform their own reasonability determination, it may be necessary to further improve upon the quality of the OCR output by performing a text cleaning algorithm on the OCR output. Text cleaning may be implemented by a category of NLP models designed for Language Modeling. Additionally, machine learning algorithms and deep learning algorithms may be utilized to further improve upon the OCR results. Exemplary categories of language models may include: statistical (n-gram), graphical (CRF/HMM), and neural (RNN, LSTM, skip-gram, BOW, etc.). While each category of language model may process datasets of particular structure and content differently, the modular nature of the processing pipeline allows the most appropriate language model to be selected based upon the document being processed. For instance, a first language model may be selected if the document is a progress note while a second language model may be selected if the document is a lab result. As another example, a first language model may be selected if the document is from a first institution and a second language model may be selected if the document is from a second institution. As another example, a first language model may be selected if the document is from a first clinician and a second language model may be selected if the document is from a second clinician.

In one aspect, due to the frequency of tables, charts, structured headers, and other features in medical documents, neural language models may be preferred. Neural networks for language modeling may be trained over millions of sentences and perform best when trained over text from the same domain as they will encounter in a production system. For example, language models trained over medical/clinical text will perform better in medical-based OCR text cleaning tasks than language models trained over online reviews, news articles, or other generic and freely-available sources. Similarly, language models trained over clinical documents that are specific to a particular disease state, such as cancer, may perform better in medical-based OCR text cleaning tasks upon disease state-related clinical documents than language models trained over clinical documents that are not specific to a particular disease state. By providing a training set having millions of clinical documents that are similar to the documents submitted for OCR, an exemplary language model may be trained over in-domain text that many traditional NLP sources do not have access to, resulting in a more robust language model.

Language models may estimate the probability of a given sequence of words or characters (letters, numbers, punctuation, etc.) occurring in a current document based on the frequency of the given sequence of words or characters as they appeared in the original training documents. Language models may identify regions of OCR output that are uncommon in the training text (such as "stage iv beast cancer" is an unlikely sequence of words in medical documents). Language models may also identify which words/characters were most likely to have occurred in each position in text, for example, "stage iv _____ cancer" may have a high probability for "lung" and "breast" filling the blank. By combining a probability distribution over words most likely to fill the blank (such as in this example cancer sites, but may be medications, dates, diagnosis, treatment results, etc.) and words most likely to be OCR as "beast," the system may determine that "beast" was most likely "breast" without having to look at the image itself and only relying on linguistic patterns.

A probability distribution may be generated by applying a neural network for Named Entity Recognition (NER). For example, individual words may be provided a weighting factor for probability of occurrence across a massive training set. Statistical information may be stored that indicate likely phrases, based off a starting word, and any following words of a phrase. Each word, in turn, may be applied a weight about whether it is a starting word or a following word and the likelihood that the word is part of a phrase or standing alone in the text.

In one example, the phrase "stage iv _____ cancer" may be processed. "Stage" may be provided a starting word score of 0.6, a following word score of 0.3, and a standalone score of 0.1 which would account for the entirety of the potential distribution of the word's appearance in the training text. The word "iv" may be provided a starting word score of 0.05, a following score of 0.55, and a standalone score of 0.4. The word "cancer" may be given a starting score of 0.1, a following score of 0.7, and a standalone score of 0.2. A sentence analysis for the exemplary NER may find that because "stage" has a high probability for being a starting word and "iv" has a high probability for being a following word, that "_____" may have a higher probability for being a following word that matches "stage iv _____" or "stage iv _____ cancer" in a phrase.

Additionally, because "cancer" similarly has a high probability for being a following word, NER may predict that the "_____" is either a following word that continues the word beginning at "stage" or may be a beginning word that begins before "cancer". Because the word "beast" has a beginning word score of 0.1, a following score of 0.2 and a standalone score of 0.7, the model may flag that "beast" does not fit within the expected sequence of words. By comparing similar words, (such as breast, feast, rest, roast, wrest, etc.) the NER model may identify that breast has a beginning score of 0.5, a following score of 0.3, and a standalone score of 0.2, making breast fit within two models of the predicted phrases and selecting "breast" to replace "beast" based on the predicted phases alone. The modified phrase then may be further tested, or tested alone using a more generalized probability distribution. For example, the training date may weight the occurrence of words in medical texts. As discussed above, while the word "beast" may rarely occur in a patient report, (such as patient was mauled by unknown beast), "breast" may occur more frequently (such as patient expresses concern re: lump in breast, breast cancer, stage iv breast cancer, patient's breast recovered from surgery, etc.), giving "breast" a much higher probability of occurrence weighting than "beast," such similarity analysis likewise can apply to an EMR/EHR. As a result, the preprocessing stage 64 may replace "beast" with "breast," terminate pre-processing, and indicate that the resulting text is reasonable.

In an alternate embodiment, a tabular extraction method may be performed across EMR and EHR documents, similar to the tabular extraction method discussed above with regard to the output of the electronic document capture, such as incorporating the exemplary tabular extraction approach involving masks 1-3 of FIG. 4. Tabular extraction involves applying MLA and deep learning algorithms to optimize the OCR process for reports which may have a standardized format.

Returning to FIG. 5, once the pre-processing stage 64 has completed, the generated OCR output may be stored for later retrieval by the parser stage 66 of the intake pipeline 62. In an alternative embodiment, the preprocessing stage may check in with parser 66 to confirm availability and pass the OCR output to the parser stage directly. Due to the modular nature of the intake pipeline 62, each processing stage may process their respective data without regard for the specific OCR or pre-processing methods. A modular pipeline approach allows the pipeline to swap in and out the most appropriate OCR and pre-processing technologies to improve the results of the overall processing.

Sentence splitting is a function of NLP that may be incorporated to parse sentences into meaningful structures. Documents may arrive in either plaintext format (containing all text from the document) or in a structured OCR format (including the text as well as bounding boxes for every character, word, and sometimes paragraph if the model is capable of identifying paragraph regions). Conventional sentence splitting may be implemented by many readily available NLP applications, including, such as any of CoreNLP, Spacy, AllenNLP, or NLTK. The system may implement a plurality of NLP applications, and identifying a most appropriate tool for sentence splitting may be depend on the nature of the clinical documents at hand, since clinical documents have a large variety in document layouts and content. Each tool for sentence splitting has advantages for particular types of documents, expected sentence structures, etc. In particular, documents often have headers and footers with useful structured text data, but headers/footers may not be presented in a standard sentence format (such as document citation or quote) and may confound certain sentence splitters. Similarly, doctors may use clinical shorthand which conventional NLP tools are not trained to parse; for example, a doctor may write "pt dx luad 2017" to mean "the patient was diagnosed with lung adenocarcinoma in 2017."

These deficiencies in sentence splitting may be overcome by adding models before this stage to identify whether text is semi-structured data, well-formed text, clinical shorthand, uninformative headers/footers, etc. By creating methods for distinguishing between these types of text, the intake pipeline may use specific models to extract information from each type. For example, complex sentences may be broken down into simple sentences by looking for coordination constructs, adjectival clauses, evaluating parataxis, prepositional phrases, etc., by applying phrase-based or syntax-based machine translation approaches. For sentences which are well-structured (such as following traditional grammar and prose), parse trees or deep semantic representations may be utilized. For sentences which are noisy (such as structured, but with unclear boundaries), a maximum entropy approach may be utilized. In texts which are very specialized in nature (such as medical texts, legal texts, etc.), a tokenization and document segmentation algorithm may be applied. By implementing sentence splitting, the processing pipeline may split the document into sentences for individual parsing.

Candidate extraction may be performed using one of above-referenced approaches. For example, one approach may include a symbolic approach that relies on the structure of the sentence. Relying on the structure means that the sentence may be passed into a dependency parser or constituency parser.

Constituency-based parse tree text analysis systems may incorporate a list of phrase types that are likely to occur in sentences containing medical concepts. A subset of phrase types from the improved list of concepts may include:

CC—Coordinating conjunction, (such as and, but);
CD—Cardinal number, (such as one, two, 1, 2);
DT—Determiner, (such as a, the);
EX—Existential clause, (such as there);
*FW—Foreign word, (such as absentia, nauseam, habeas);
IN—Preposition or subordinating conjunction, (such as although, because);
*JJ—Adjective, (such as wet, fast);
*JJR—Adjective, comparative, (such as -er);
*JJS—Adjective, superlative, (such as -est);
LS—List item marker, (such as numbering, bullets);
MD—Modal, (such as shall, will, might);
*NN—Noun, singular or mass, (such as cell, cancer);
*NNS—Noun, plural, (such as cells, fingers);
*NNP—Proper noun, singular, (such as California, London);
*NNPS—Proper noun, plural, (such as the Joneses, the Bushes);
PDT—Predeterminer, (such as both, a lot);
POS—Possessive ending, (such as 's);
PRP—Personal pronoun, (such as we, she);
PRP$—Possessive pronoun, (such as his, hers);
*RB—Adverb, (such as quite, then);
*RP—Particle, (such as not, to);
*SYM—Symbol, (such as @, &);
*UH—Interjection, (such as ah, oh);
*VB—Verb, base form, (such as run, inject);
*VBD—Verb, past tense, (such as ran, injected);
*VBZ—Verb, 3rd person singular present, (such as runs, injects);
WDT—Interrogative determiner, (such as what, which);
WP—Interrogative pronoun, (such as who, whom);
WP$—Possessive interrogative pronoun, (such as whose);
WRB—Interrogative adverb, (such as where, how); and
.—Period character.

While conventional implementations are not optimized for technical texts (medical texts), the conventional list of phrase types may be augmented to include additional phrase types to optimize sentence splitting for medical-based texts. Such additions have been indicated with an asterisk (*). Conventional implementations that involve constituency-based parse trees include Apache cTAKES™, Stanford Parser, TensorFlow, and Charniak-Johnson.

Figure 7:
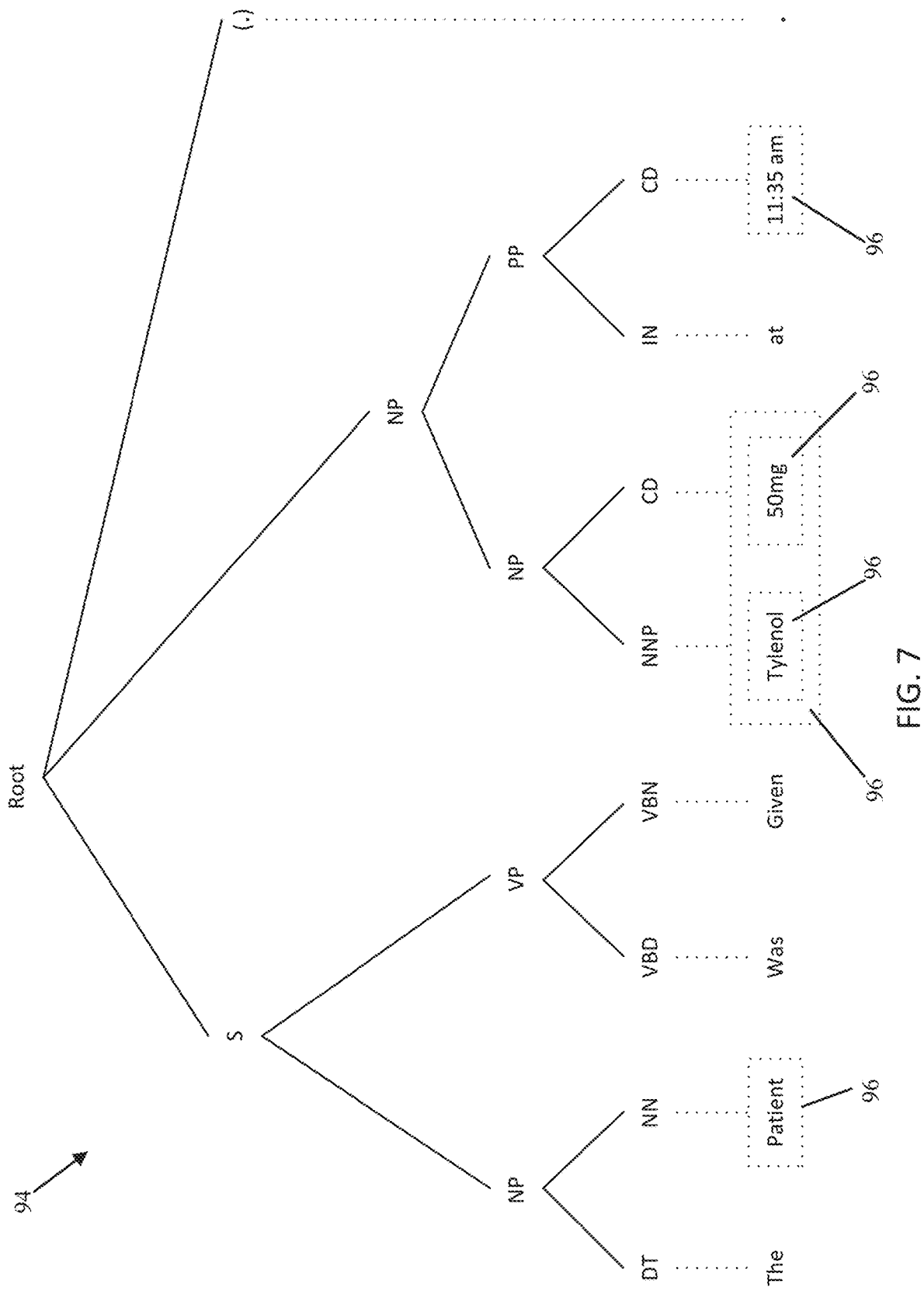
FIG. 7 is an exemplary constituency-based parse tree representation according to an embodiment.

Turning to FIG. 7, one example of a constituency-based parse tree is depicted. In that example, a constituency-based parse tree may receive a sentence "the patient was given tylenol 50 mg at 11:35 am." from which a parse tree may be generated. As depicted in the tree of FIG. 7, concepts may be identified (such as medical concepts) using different linguistic phrases and parts of speech. An example constituency parser then may generate: (ROOT (S (NP (DT The) (NN patient)) (VP (VBD was) (VP (VBN given) (NP (NP (NNP Tylenol) (CD 50 mg)) (PP (IN at) (NP (CD 11:35 am)))))) ( . . . ))).

In this example, phrase types: S, VP, NP, and PP markers are not in the above list. They represent the top-level sentence, verb phrase, noun phrase, and prepositional phrase, respectively. Furthermore, "patient", "Tylenol", "Tylenol 50 mg", "50 mg", and "11:35 am" may be included in a list of concept candidates 96 (graphically represented as dotted lines around the words in the parse tree). Concept candidates may be determined by noting important phrase types (such as NP, CD, etc.) and may be further refined by comparing any associated text against a list of weighted words, whereby words which are weighted above a threshold weight may be presented as concept candidates. For example, the word "patient" may be flagged as a concept candidate, but due to its low weighting factor, may be removed from the candidate list.

In another embodiment, an MLA may be utilized to identify concept candidates. An exemplary MLA for identifying concept candidates includes a name entity recognition (NER) model. NERs may be implemented using conditional random fields, convolutional neural networks, attention based neural networks, long short term memory networks, or other neural models.

Language models may vary based upon the type of document being processed, (such as pathology reports, progress notes, and other EHR and EMR documents, etc.), to optimize the type of information which may be extracted from the documents. For example, a whole document classifier may be applied to a progress note (physician generated report of patient status on each checkup), pathology report, or other EHR/EMR documents to identify a patient's gender, cancer types, or other information that may require verification over one or more documents to provide reliable predictions. For a whole document classification, the text of the entire document may be evaluated before the document as a whole is classified (such as male/female, lung/breast cancer, date of birth, etc.). For other types of information, a sequence labeling classifier may be applied to a progress note, pathology report, or EMR/EHR documents to identify, for example, medications taken by a patient, therapies a patient may be undergoing, or other information which may be difficult to extract due to the extensive number of varying entries for each type of class. For a sequence labeling classification, each sentence, or combination of sentences in the document may be evaluated before the document is assigned another classification for identifying a class entry (such as a medication or therapy of the patient). The implementation details of an exemplary whole document classifier and sequence labeling classifier are discussed below.

In one aspect, a whole document classifier may rely on a training model that has been trained on thousands of medical documents found in EMRs and EHRs of patients. The training data may be provisioned with the parts of speech assigned to words and the true classification for each patient (such as male/female, age, ethnicity, etc.). A machine learning algorithm or a neural network may process the training data to generate a rule set or a trained neural network, respectively. In an exemplary rule set, a list of words with corresponding weights may be generated based upon the frequency they appear in text with proper classification vs text without the proper classification. For example, a rule set for determining if a document for a patient is to be classified according to gender may have a list of words including "male", "man", "he", "his", "testicular", "prostate", etc., which are weighted heavily towards identifying gender as male and a list of words including "female", "woman", "her", "she", "breast", "ovaries", "ovulation", "menstrual", etc., which are weighted heavily towards identifying gender as female.

The rule sets may include a vector of, for example, three hundred words and their respective weights, and each rule set may be applied over all words in a sentence to generate weights for every sentence. For example, a sentence "The patient was given prostate exam after he complained about having difficulty urinating in the mornings" may be given a high weight for gender as male because of words "prostate exam" and "he". After each word of each sentence is processed, each respective sentence may be assigned a sentence vector (such as 10% female, 90% male), then each sentence in a document may be processed to assign a document vector, and finally, each document in a patient's EMR or EHR may be processed to assign a patient vector.

At each level of granularity, the whole document classifier may be interrupted, for example, if a sufficient level of certainty has been reached or processing was intended to terminate at that level. For example, if a document has been determined to have a high incidence of accuracy because a table on page 3 of a document may always return the correct gender for the patient, then the algorithm may identify that high accuracy has been provided for the document based on the one sentence of that document and stop processing a gender classification at the sentence level vector for that patient. Furthermore, a patient level vector may not be generated if a document level vector has reached a certain threshold of certainty (such as 95%), or if, for example, only one document is being processed.

Figure 8:
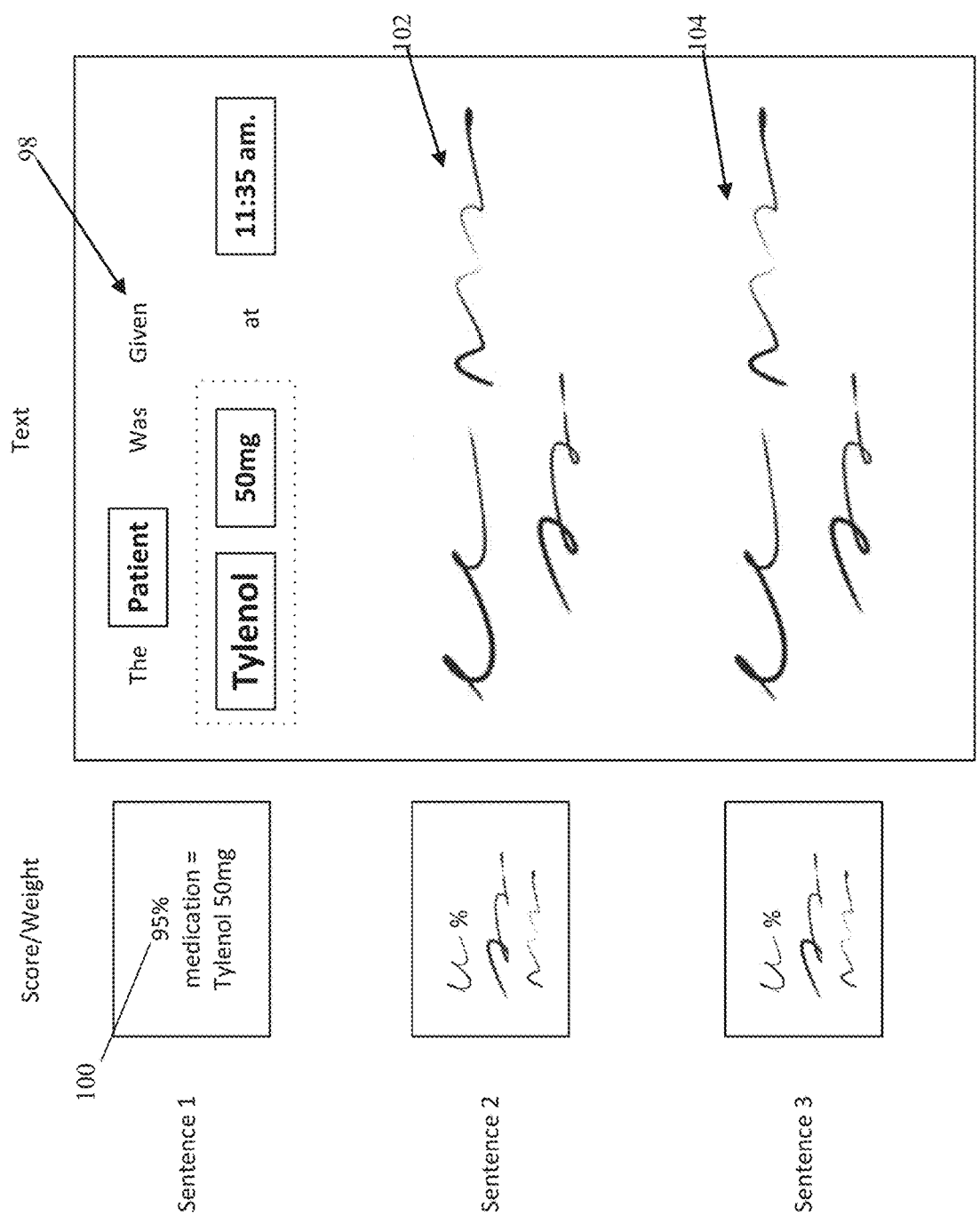
FIG. 8 is an exemplary word weighing representation according to an embodiment.

FIG. 8 provides a visual representation of word weightings for a sentence 98 containing "The patient was given Tylenol 50 mg at 11:35 am." At the word level, "the", "was", "given", and "at", may be given low weights, "patient" and "11:35 am" may be given medium weights, and "Tylenol" and "50 mg" may be given high weights. As a result, the overall sentence may be classified with a high weight 100 (such as 95%) that medication the patient has taken includes Tylenol 50 mg. For this example, because such a high confidence value is determined, the processing may not need to continue to evaluate other sentences in the document to determine that the patient did indeed take Tylenol 50 mg, but each sentence 102, 104 will be processed to determine if other concepts are identified (such as to identify gender, other medications, other treatments, or demographic information). In this example, even though only the medication concept is given a high weight, each of the identified concept candidates may be retained for the next stage of the intake pipeline for further processing; alternatively, those identified concept candidates may be dropped from the candidate list.

In some circumstances, a high level of confidence may not be available. For example, a patient who has undergone a gender reassignment surgery may have documents with a high level of confidence for one gender before surgery and a high confidence for another gender after surgery, or a document for a patient of a different gender may have been misfiled in the current patient's file. When a level of certainty lies below a threshold value (such as 90%), the whole document classifier may output the highest level vector calculated identifying, for example, a 60% confidence male and 40% confidence female. The output may also include one or more identifiers for which document, which section of which document, which sentence, or even which word from which the confidence values were calculated. In another embodiment, no prediction may be generated when the confidence value is below the threshold. In still other embodiments, documents which have contention in a prediction may be flagged, a true determination of classification may be obtained, and the documents and the true classification may be provided to a training engine which may retrain the rule set or neural network to further improve accuracy.

As discussed above, in another aspect, a sequence labeling classifier may be implemented. An MLA or neural network may be trained to generate a rule set identifying words and word sequences which are likely to identify concept candidates. Such concept candidates may include stand-alone words such as "patient," "age," or "gender," with a high stand-alone rating. It should be noted that these words may not be commonly coupled with other words in medical text but may still have some word couplings (such as under age). Other concept candidates may include words which are commonly linked to other words in a medical text. Words which commonly begin a multi-word concept include "breast" (such as breast cancer, breast reduction, breast augmentation, breast surgery) and "stage" (such as stage I cancer, stage II cancer, etc.). Other such words may include "high" (such as high blood pressure), "low" (such as low cholesterol), or "heart" (such as heart attack, heart failure). Words which commonly begin a multi-word phrase may feature a high beginning score and a medium stand-alone score. Intermediary words in a multi-word phrase (such as _____ cancer, _____ cell, _____ failure) are words which may have a high intermediary score and a medium stand-alone score). For example, each word in a sentence may be assigned a value for the likelihood that the word is a beginning of a multi-word phrase (such as a "B" value), an intermediary of a multi-word phrase (such as an "I" value), and a standalone word (such as an "O" value), and then each word or collection of words may be evaluated to identify clinical concepts.

Figure 9:
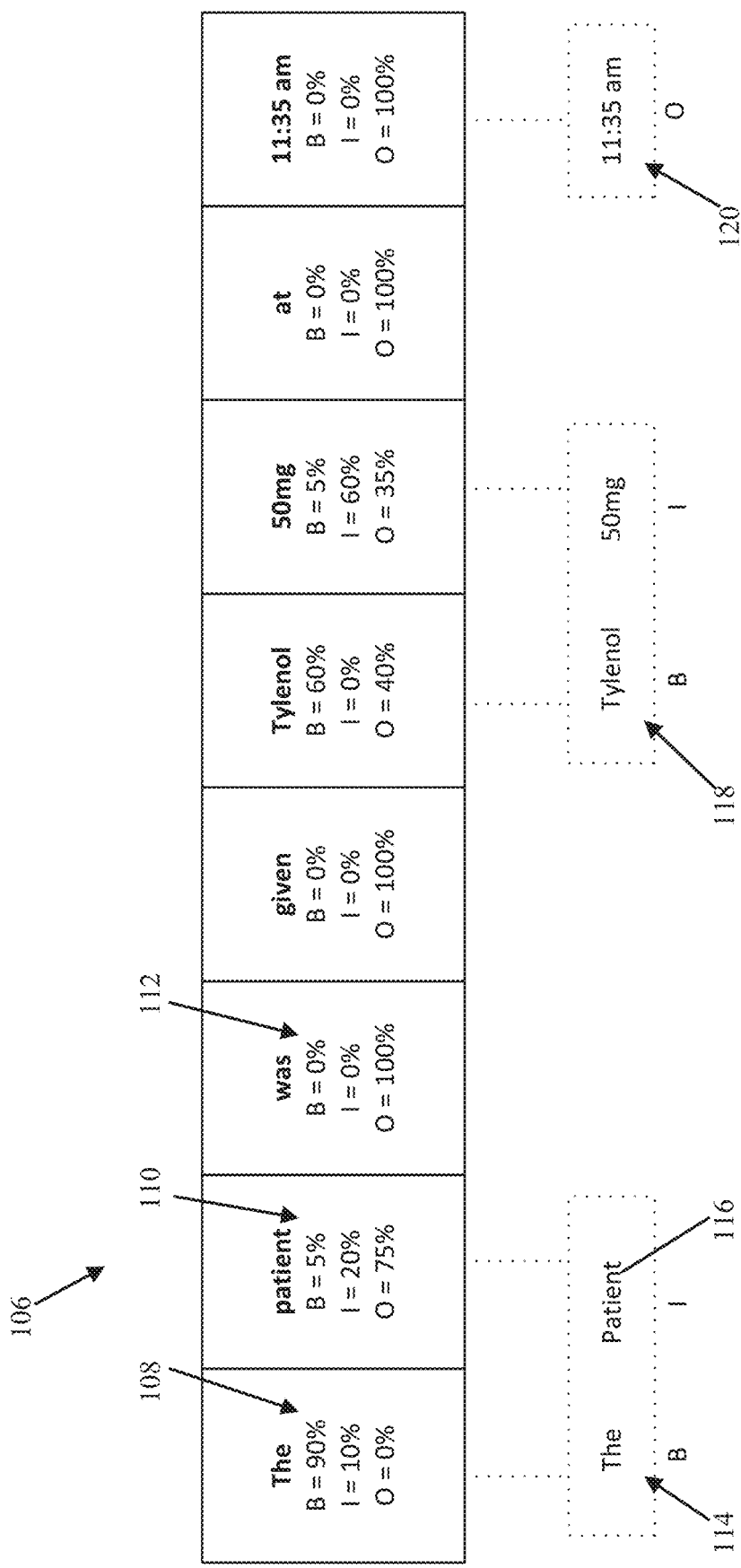
FIG. 9 is an exemplary sequence labeling classification representation according to an embodiment.

Turning to FIG. 9, a sequence labeling classifier 106 may provide a "BIO" score for each word, where a BIO score (10, 30, 60) would mean that the associated word is the first word in a multi-word phrase in about 10% of its occurrences in the training set, an intermediary word in a multi-word phrase in about 30% of its occurrences in the training set, and a stand-alone word in about 60% of its occurrences in the training set. For example, the word "the" almost always precedes another word and occasionally is an intermediary word of a multi-word phrase, so may be provided a BIO score 108 of (90, 10, 0). "The" may also be considered an extraneous word, despite almost always preceding other words of importance, so it may be provided a BIO score of (0, 10, 90) to prevent processing, "patient" may be provided a BIO score 110 of (5, 20, 75), and "was" may be provided a BIO score 112 of (0, 0, 100). The sequence labeling model may begin processing the sentence at the first word, "the," and then note a high incidence of that word being the beginning value of a multi-word phrase (in the first incidence where BIO score is (90, 10, 0)), process the second word "patient" to note a high incidence of being an intermediary or stand-alone word, and process the third word "was" to note a high incidence of being a stand-alone word. By recognizing a potential beginning of a multi-word concept, a potential intermediary of a multi-word concept, and a distinct non-multi-word entry, the sequence labeling model may identify a first multi-word concept. Therefore the sequence labeling model may indicate "the patient" 114 as a likely candidate concept for the multi-word label and "patient" 116 as a likely candidate concept for the stand-alone word label.

Processing may continue word-by-word until another stand-alone word (B, I, or O labels) or multi-word (BIII . . . labels) are detected. In the example of FIG. 9, another multi-word phrase 118 may be detected at "Tylenol 50 mg," and concepts "Tylenol" and "Tylenol 50 mg" may be generated. A final concept 120 may be generated at "11:35 am."

A sequence labeling classifier may be able to identify labels with a higher accuracy than a parse tree by linking words together through their labels (such as BI, BII, BIII, etc.) to identify multi-word concepts (such as heart attack, stage IV cancer, medial tibial stress syndrome, etc.) as the totality of their concept rather than each of the words in multi-word concept.

The number of candidate concepts which may be extracted may be needlessly large. For example, in patient file with thousands of documents, a concept candidate for breast cancer may occur hundreds of times, a concept for lung cancer may occur tens of times, and a concept for liver cancer may only occur once. It may be useful to filter/rank the mentions of each concept candidate to reduce repetition in the following stages in the pipeline. For concept candidates which may be consolidated (such as mentions of breast cancer for diagnosis) the concept candidate may be reduced to a single concept with a count field in the hundreds. Furthermore, if concept candidates are competing for the same field, the concept candidate may be coupled with a reliability index based upon the frequency of the concept candidate occurring in relationship to the others (such as 200 mentions of breast cancer, 13 mentions of lung cancer, and 1 mention of liver cancer may be processed to a 200/214 reliability index that the patient has breast cancer). The highest ranked competing concept candidate may be preserved along with a reliability index, or a consolidated report of the most frequent competing concept candidates may be preserved along with their count values and/or reliability index.

Using any of the above methods, candidate extraction generates a plurality of candidate concepts which may be evaluated in the following stage for entity linking.

Returning to FIG. 5, the entity linking pipeline stage 68 receives/retrieves the candidate phrases as a list and may process each candidate to identify any links between the phrases and known entities (such as the enumerated list of medical drugs discussed above). Entity linking is the task of determining whether a candidate concept (phrase) is a relevant clinical concept. Relevancy may be determined by the presence of the candidate concept in any medical dictionary or the universal dictionary described above. Relevancy may also be determined based on proximity to a concept candidate hit. For example, a time "11:35 am" may not result in a hit in any dictionary as a medical concept. However, certain medical concepts, such as medications, may fall within an abstraction category such as treatment. A treatment may have fields such as treatment type (the medicine) and date and time of treatment (11:35 am). By considering proximity to other concept candidates, key information may be retained even if the concept may not exist in the database. The retained candidate concept may not be classified as a linked entity, but may be associated with the linked entity for abstraction purposes.

Within the entity linking pipeline stage 68, the list of concept candidates generated in the previous pipeline stage may be provided to a dictionary lookup for matches. Conventional dictionary lookup tools may include Elasticsearch, Solr, Algolia, or Sphinx. In one aspect, a direct dictionary lookup may not always result in a database hit (the candidate is in the database) because of typographical errors, OCR errors, shorthand, or other confounding factors. In those situations, candidates which are not an exact match may still be found in the database by applying fuzzy matching logic. For example, the entity linking pipeline stage 68 may expect to find matches for "Tylnol" and "Tylnol 50 mg" because exemplary queries allow for "fuzzy matching," which will correct potential typographical errors or OCR errors that occur in "Tylenol."

Fuzzy matching may be implemented by an approximate string matching algorithm, such as the exemplary fuzzy matching algorithm discussed above.

Fuzzy matching is structured around the text concepts included in the above enumerated list or the UMLS, including metadata fields CUI (the UMLS unique ID) and AUI (dictionary-specific unique ID), so that an exhaustive search may be performed for all medical concepts. The dictionary search engine may also return metadata about the specific entry detected (such as universal ID assigned in the above enumerated list or the UMLS), which is useful for understanding Tylenol as a medical concept and not just the correct spelling of a drug. At the end of text normalization, some of the extracted candidates may have zero matches but others may have many matches. For example, there are many versions of Tylenol throughout the UMLS database because of the number of dictionaries represented therein. Fortunately, the CUI (the UMLS uuid) provides a generalization to join similar concepts, which reduces the number of matches from one for each potential database to the number of unique CUIs represented. Not all concepts can be simplified so succinctly, though. For example, "Tylenol" is a different concept than "Tylenol 50 mg", which is a dosage-specific version of "Tylenol". Any ambiguation from "Tylenol 50 mg" to "Tylenol" would effectively constitute a loss of information.

As discussed above, fuzzy matching may also apply on a word-by-word basis rather than a letter-by-letter basis. Furthermore, in still another embodiment, both fuzzy matching on a character by character basis and word by word basis may be applied concurrently to generate entity matches.

Certain features, such as the TNM Classification of Malignant Tumors (TNM) is a globally recognized standard for classifying the extent of spread of cancer, must be preempted from fuzzy matching. TNM is a notation system that describes the stage of a cancer, which originates from a solid tumor, using alphanumeric codes: T describes the size of the original (primary) tumor and whether it has invaded nearby tissue; N describes nearby (regional) lymph nodes that are involved; and M describes distant metastasis (spread of cancer from one part of the body to another). For example, T may be designated a value to estimate size or direct extent of the primary tumor (Tx: tumor cannot be assessed, Tis: carcinoma in situ, T0: no evidence of tumor, T1, T2, T3, T4: size and/or extension of the primary tumor), N may be designated based upon the degree of spread to regional lymph nodes (Nx: lymph nodes cannot be assessed, N0: no regional lymph nodes metastasis, N1: regional lymph node metastasis present; at some sites, tumor spread to closest or small number of regional lymph nodes, N2: tumor spread to an extent between N1 and N3 (N2 is not used at all sites), N3: tumor spread to more distant or numerous regional lymph nodes (N3 is not used at all sites), and M may be designated based upon the presence of distant metastasis (M0: no distant metastasis, M1: metastasis to distant organs (beyond regional lymph nodes)). Exemplary TNM codes may be "pT1 pN0 M0" or "pT4 pN2 M1". Due to the importance of the TNM codes being parsed precisely as they appear to maintain the TNM values, fuzzy matching may be disabled for stop words relating to TNM values, for example, "t0", "T1a", "t3", so that fuzzy matching does not change a "t1" into a "t2" to match a database Entity. NLP may be combined with restricted fuzzy matching in certain embodiments to correct OCR errors related to TNM codes. For example, a NLP model may detect that TNM is being referenced by detecting the presence of a T, N, and M code; however, classification may fail due to an OCR of "pT0" with "pTo", by allowing a restricted fuzzy matching of only similar characters (such as an "o" for an "0"), TNM codes may be maintained while still correcting for errors.

Due to the large volume of concept candidates that may exist from the previous pipeline stage, merely searching for a match and terminating the search upon finding a single match may provide a substantial benefit in reducing the processing time spent crawling the relevant databases/dictionaries. However, the best matches may not be the first matches, and if there are multiple matches within a group (such as synonyms which are off by a single word to the concept candidate), it may be necessary to pick the match which has the lowest fuzzy "score" (the value that counts the number of errors corrected to generate the fuzzy match). If there are still ties (such as there are two matches of equal fuzzy "score"), then the tied matches may be sorted based on length of characters or length of words (such as shorter matches with less words/characters score higher than longer matches with more words/characters). Any unresolved matches may then be selected randomly or according to a first-in, first-out FIFO queue of matches, such that the first match is selected.

Templates, Fuzzy Text Matching & Regular Expressions:

Many reports within EMRs and EHR are provided in consistent formatting across institutions for periods of time (such as patient intakes may share the same form for a period of time until the next revision). Relying on this consistency, the system may consider a case where a hospital system prints its pathology reports using the same template and had a different template for any documents that were created before Jan. 1, 2001. If Pathology Reports from this hospital system are identified as frequent documents received in EMR and EHR, optimizations may be applied to processing to create methods for extracting information from known locations within the shared templates of each respective form. An exemplary method (such as the method described above) may also include multiple parts, as follows:

Document classification: The system may generate an image or text classification model to: determine whether a given document belongs to one of the templates that may be extracted from, assign the document an identifier for linking the document to the template, use the identifier to look up the classification model optimized for the document, and classify the document. Exemplary template-based approaches and tabular approaches are discussed above.

Regular Expressions: The system may identify anchor strings regularly occurring in text that identify where key health information may reside. For example, the system may recognize that "DOB" is a string to search for dates of birth and "Pathological Diagnosis" may be a header to a section that provides concepts for linking to a pathological diagnosis.

Fuzzy Text Matching: As discussed above, the system may apply a fuzzy search algorithm to a regular expression in order to allow the application of regular expressions to words which have OCR errors, typographical errors, or are otherwise confounded.

Templates: Once a document has been classified, and regions of text may be determined in advance, an image classification model may leverage the predetermined region locations to identify those same regions within a document image to extract key health information (clinical concepts). For example, document headers may often be visually structured for presenting information to the reader, and that known visual structuring may contain useful demographic information. By identifying a document header, processing may include rotating/skewing the image to line up the template, removing image irregularities, OCR of the text, and applying regular expressions to extract any information from the standardized format. Any concepts extracted from the template may be provided to the entity linking pipeline 140 and may be processed to identify any respective matching concepts for linking.

Returning to FIG. 5, in another embodiment, entity normalization (such as at step 70) may be applied to determine which of the entity linked concepts of the previous stage are relevant to abstraction and, if they are relevant, which encoding schema may be applied to encapsulate the abstraction completely. For example, "Tylenol" and "Tylenol 50 mg" may match in the dictionary from UMLS with a concept for "acetaminophen". It may be necessary to explore the relationships between the identified concept from the UMLS dictionary and any other concepts of related dictionaries or the above universal dictionary. Though visualization is not required, these relationships may be visualized through a graph-based logic for following links between concepts that each specific integrated dictionary may provide.

Figure 5:
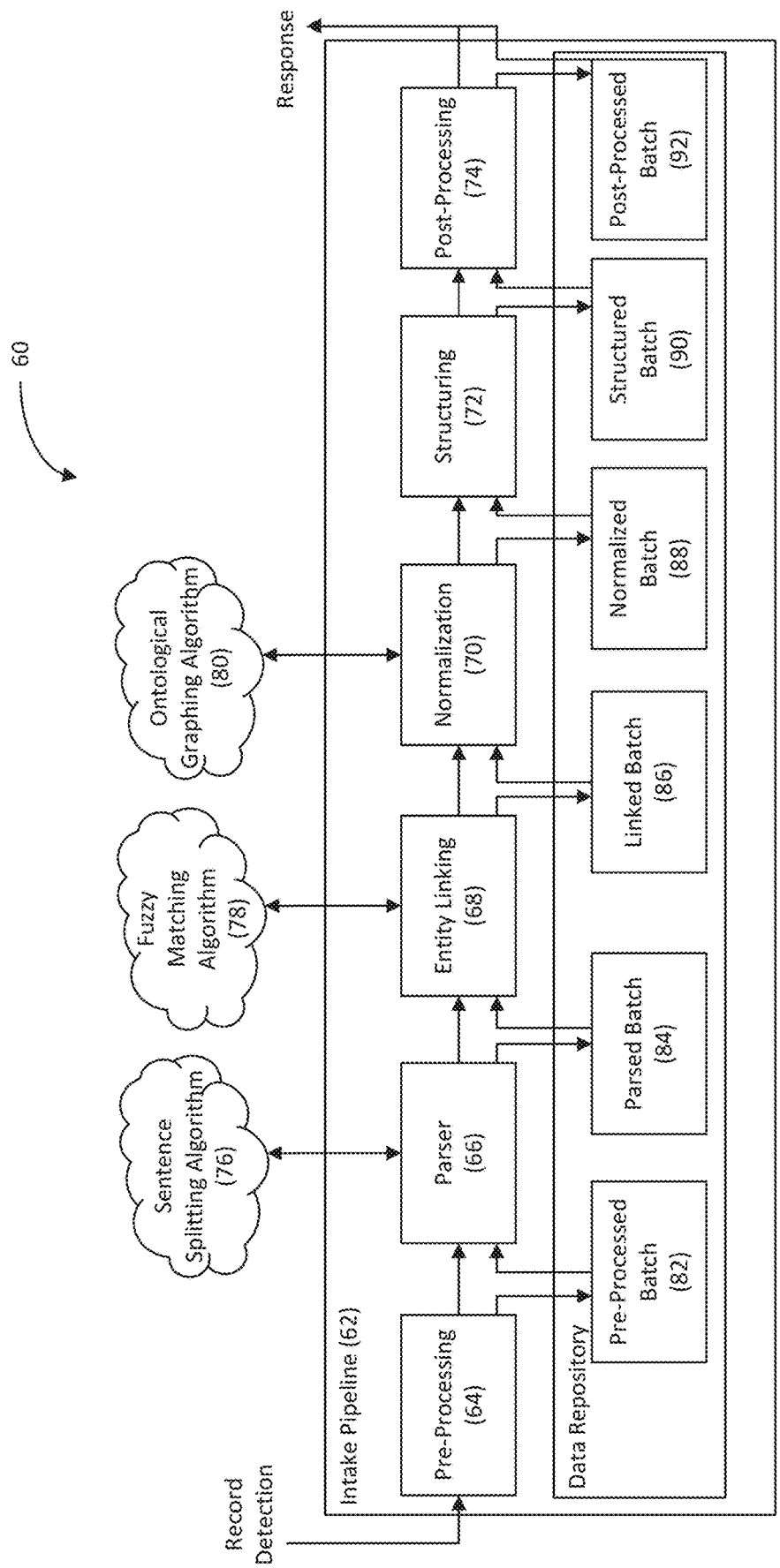
FIG. 5 is an exemplary pipeline for processing electronic records into structured results.
Figure 10:
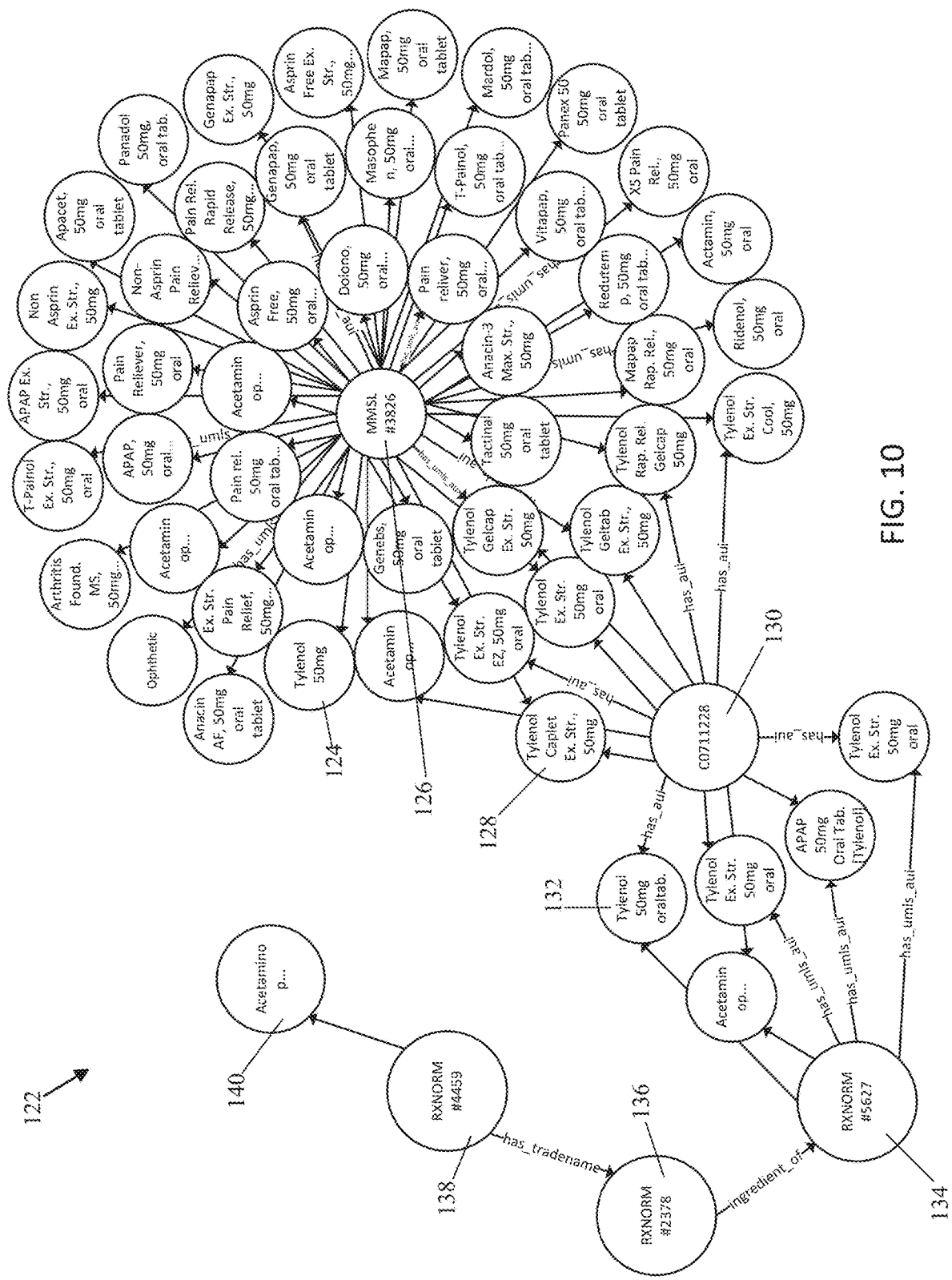
FIG. 10 is an exemplary ontological graph database for viewing links between different dictionaries.

FIG. 10 is an exemplary ontological graph database 122 for viewing links between different dictionaries (databases of concepts) that may be interlinked through a universal dictionary lookup in order to carry out the normalizing stage 70 in FIG. 5. Conventional ontological graph databases may include GraphT, Neo4j, ArangoDB, Orient, Titan, or Flockdb. The following references to dictionaries and databases are for illustrative purposes only and may not reflect accurately the concepts/synonyms, entities, or links represented therein. Links between two concepts may represent specific known relationships between those two concepts. For example, "Tylenol" may be linked to "acetaminophen" by a "trade name" marker, and may be linked to "Tylenol 50 mg" by a "dosage of" marker. There may also be markers to identify taxonomic "is a" relationships between concepts. "Is a" markers provide relationships between over some clinical dictionaries (such as SNOMEDCT_US, Campbell W S, Pederson J, etc.) to establish relationships between each database with the others. For example, we can follow "is a" relationships from "Tylenol", "Tylenol 50 mg", or "acetaminophen" to the concept for a generic drug. Such a relationship may not be available for another concept, for example, a match to the dictionary for UMLS to "the patient" or "patient" may not have a relationship to a medication dictionary due to the conceptually distinct natures of each entity. Relationships may be found between drugs that have the same ingredients or are used to treat the same illnesses.

Other relationships between concepts may also be represented. For example, treatments in a treatment dictionary may be related to other treatments of a separate treatment database through relationships describing the drugs administered or the illness treated. Entities (such as MMSL #3826, C0711228, RXNORM # . . . , etc.) are each linked to their respective synonyms, (such as Tylenol 50 mg, Acetaminophen, Mapap, Ofirmev, etc.). Links between concepts (synonyms), may be explored to effectively normalize any matched candidate concept to an RXNORM entity.

Returning to FIG. 10, the concept candidate "Tylenol 50 mg" 124 may have a hit in the National Library of Medicine Database MMSL. In the preceding stage of the pipeline, "Tylenol 50 mg" may have been linked to the Entity MMSL #3826 126 as an identifier for the "Tylenol 50 mg" concept in MMSL. The linked Entity, MMSL #3826, may reside in a database which is not a defined database of authority, or, for document classification purposes, MMSL #3826 may not provide a requisite degree of certainty or provide a substantial reference point needed for document/patient classification. Through entity normalization, it may be necessary to explore links to MMSL #3826 until a reference entity of sufficient quality is identified. For example, the RXNORM database may be the preferred authority for identifying a prescription when classifying prescriptions a patient has taken because it provides the most specific references to drugs which are approved by the U.S. Food and Drug Administration (FDA).

Other authorities may be selected as the normalization authority based upon any number of criteria. The exact string/phrase "Tylenol 50 mg" may not have a concept/entity match to the RXNORM database and the applied fuzzy matching may not generate a match with a high degree of certainty. By exploring the links from MMSL #3826, it may be that concept "Tylenol Caplet Extra Strength, 50 mg" 128 is a synonym to "Tylenol 50 mg" in the MMSL database. Furthermore, concept "Tylenol Caplet Extra Strength, 50 mg" may also be linked to Entity C0711228 130 of the UMLS database. By exploring the synonyms to "Tylenol 50 mg" 124 through Entity MMSL #3826 126, the concept candidate may be linked to the UMLS Entity C0711228 130. However, the UMLS Entity C0711228 130 is not the preferred authority for linking prescriptions, so further normalization steps may be taken to link to the RXNORM database. Entity C0711228 130 may have synonym "Tylenol 50 MG Oral Tablet" 132 which is also linked to RXNORM #5627 134. RXNORM #5627 134 may be a normalization endpoint (once RXNORM #5627 has been identified, normalization may conclude); however, RXNORM #5627 134 may also represent the Tylenol specific brand name rather than the generic drug name. A degree of specificity may be placed for each source of authority (normalization authority) identifying criteria which may been desired for any normalized entity. For example, a medication may need to provide both a brand drug name and a generic drug name. Links in the RXNORM database may be explored to identify the Entity for the generic drug version of Tylenol. For example, RXNORM #5627 134 may have an "ingredient of" link to RXNORM #2378 136 which has a "has tradename" link to RXNORM #4459 138 with concept acetaminophen. RXNORM #4459 138 is the Entity within the RXNORM database which represents the generic drug 140 for Tylenol 50 mg and is selected as the normalized Entity for identifying a prescription in the classification of prescriptions a patient has taken. In this aspect, normalization may first identify an Entity in the dictionary of authority (as defined above) and may further normalize within the dictionary of authority to a degree of specificity before concluding normalization.

For each field of medical data that is abstracted in the intake pipeline, reasonable reference points for normalization may be identified (such as RXNORM for medications, SnoMed for cancers) and which types of relational links may be traversed from matched concepts in the fields of medical data. As described above, medical data may include fields of patient demographics (such as patient name, date of birth, gender, ethnicity, date of death, address, smoking status, diagnosis dates, personal medical history, family medical history, etc.), clinical diagnoses (such as date of initial diagnosis, date of metastatic diagnosis, cancer staging, tumor characterization, tissue of origin, etc.), treatments and outcomes (such as therapy groups, medications, surgeries, radiotherapy, imaging, adverse effects, associated outcomes, and corresponding dates, etc.), and Genetic Testing and Labs (such as genetic testing, performance scores, lab tests, pathology results, prognostic indicators, and corresponding dates, etc.). Each of the fields (such as address, cancer staging, medications, genetic testing, etc.) may also have a plurality of subfields. For example, address may have subfields for type of use (such as personal, business), street, city, state, zip, country, and a start or end date (date that residency at the address begins or expires). Genetic testing may have subfields for the date of genetic testing, testing provider used, test method (such as genetic sequencing method, gene panel), gene results (such as included genes, variants, expressions, etc.), tumor mutational burden, and microsatellite instability. For medications, links as described above, including "has tradename" and "dosage of" relationships from any entity links may be traversed determine if there is a relevant drug related to the candidate concept.

In another embodiment, a linked Entity may be received from the entity linking stage of the intake pipeline. A query may be generated to search over an ontological graph database having relationships including meta-synonymous links, synonymous relationships between links, and other relationships. For example, a linked entity may resolve to Ductal Carcinoma In Situ (DCIS) in the SnoMed dictionary. SnoMed may be the preferred authority for cancers due to degree of comprehension and detailed concepts included in the dictionary, expert opinion identifies SnoMed as the best dictionary, or because SnoMed has the most comprehensive relationships between other dictionaries, is well established, and meets requirements set forth by the institutions managing the EMR/WHR. A desired degree of specificity may have selection criteria for normalized endpoints. For example, the selection criteria of a cancer type may include an Entity which identifies 1) the cancer site (where the cancer is located in the patient) and 2) the cancer type. An entity identifying DCIS may be limited to identifying the cancer type, but may not satisfy the cancer site selection criteria and SnoMed may be searched to identify a normalized Entity which satisfies both criteria.

Normalizing DCIS may include navigating "is a" relationship links within the SnoMed database until an Entity is reached which identifies the cancer site as breast. For example, DCIS may be a tier three entity which "is a" specific type of cancer under "breast cancer." Breast cancer may be a tier two entity which "is a" specific type of cancer under the root "cancer." Breast cancer may have a "has finding site" relationship to breast, which satisfies the selection criteria for identifying the cancer site (breast) and the cancer type (breast cancer). However, to prevent loss of information, both the DCIS Entity and Breast Cancer Entity may be retained for the normalized Entity to aide in Entity Structuring described below. In SnoMed, relationships between cancers are structured such that there is a finite number of jumps that "is a" links may traverse. Upon each traversal, an "is a" link may either result in a leaf node (traversed down), a terminal node (cancer with no further classification), or to the root (cancer). Traversal may stop at the first "is a" link which is encoded as a terminal node (such as based on the tier as described above, based off a relationship that exists in the node as described above, or that is predetermined as a terminal node). Other relationships which may identify terminal nodes include, for example, in a medicine dictionary, Term Types "Ingredient" or "Preferred term" (such as TTY: GN for Generic Drug Name and TY:BD/BN/FBN for Branded Drug/Name or Foreign Brand Name, etc.), or the degree of specificity may be based off of relationships (such as "is a generic", "is a brand name").

Normalization queries are constructed to prevent out of bound searches, spurious results, and infinite searches. A representative normalization query of a medication may include:

MATCH p=(start:DICT {code:"DICT#AUI"})-[has_tradename|tradename_of*0 . . . 3]-(end:DICT)-[:has_umls_aui]→(aui2)←[:has_aui]-(descendant_cui)

RETURN DISTINCT descendant_cui.cui AS match_cui, length(p) AS graph_distance

This query may return GUI's related to concepts which are linked to ingredients identified in the medications terminal node list by up to 3 trade names or generic names. In one aspect, a limit on the number of links which may be traversed and included in the query results may be included to reduce computational constraints (such as processor and memory reservations). Queries may be optimized to provide both generic and trade name normalization endpoints, for example, by not specifying or restricting the directionality of the [:has_tradename|tradename_of] portion of the query. Alternatively, queries may be directionally limited to only traverse [:has_tradename|tradename_of] in a specified direction to limit the results which are generated as desired. A terminal node entry for an ingredient to be encoded to in the medications valueset and may be encoded by including each respective code's dictionary (DICT above) and AUI into the query so that when a new entity is traversed, the AUI may be referenced with the list of terminal nodes.

A representative normalization query for a cancer type may include:

MATCH p=(cui:umls_cui)-[:has_aui]→(aui:umls_aui)←[:has_umls_aui]-(descendant:DICT)-[:isa*0 . . . ]→(:DICT {{code:"DICT#AUI"}})

RETURN DISTINCT cui.cui AS match_cui, length(p)-2 AS graph_distance

This query may return CUI's related to concepts which are lined as "is a" descendants of a given code (node). A terminal node entry for a cancer type may be encoded in the cancer valueset and may be encoded as a primary diagnosis by including each representative code's dictionary (DICT above) and AUI into the query so that when a new entity is traversed, the AUI may be referenced with the list of terminal nodes. For cancer type queries, a return value may include the graph_distance of the path, which provides a qualifier for how many "is a" nodes are in the path between the descendant and the queried code. After processing queries for each node in the primary diagnosis valueset, there may exist many descendants that point to multiple parents. The resulting query response of potential matches may be further curated according to the following logic:

If a descendant D is generated by two ancestors A and B, but A and B are not descendants of each other, then keep the mapping of D to both A and B; OR If a descendant D is generated by two ancestors A and B, but A is also a descendant of B, then discard the mapping of D to B (because A is a nearer ancestor).

In another embodiment, a concept candidate may be explored by more than one query relating to the concept. For example, a concept candidate may be explored/followed until a concept with a related structure (as described in FIG. 6) is linked/normalized, then each of the associated fields are queried in turn (Entity structuring is disclosed in more detail, below).

An aspect of query generation may include tailoring queries to avoid spurious searches. For example, by recognizing directional relationships which preserve the integrity of the source node, queries which prevent erroneous destination nodes from being reached are preferred. For example, normalizing the Brand Name Entity for Tylenol may include traversing the "ingredient of" relationship that Tylenol has. In one direction, drugs for which Tylenol is considered an ingredient of may be safely explored. However, in the other direction, the ingredients of Tylenol may be explored. An ingredient which is shared between Tylenol and another drug may be linked by, for example, magnesium stearate which is shared between Tylenol and Advil. A generic drug ibuprofen may then result from an unbounded query which does not restrict the traversal of "ingredient of" fields to prevent spurious drug hopping.

It may be advantageous to precalculate the results from frequent query searches and cache the query results for speed. Caching precomputed queries represent a tradeoff for the flexibility of results with the speed at which they may be generated. Caches may include a node hop count value that is used to resolve ties for least number of hops. Caching may be performed at the Entity Link stage and the Entity Normalization Stage. In a simplified representation, an Entity Linking Cache may include fields such as: Name of Concept Candidate, Dictionary Candidate Located In, and CUID. It may further be advantageous to identify a structure category and corresponding fields based from the identified CUID. Normalization may be directed to generate results which relate to the fields of the structure category identified. In another simplified representation, an Entity Normalization Cache may include fields such as: CUID, Medical Concept Structure, and normalized response for concept (Normalized CUID). Additional fields for either table may include: graph distance (number of hops), preferred dictionary CUID, predefined entries (such as names, regions, categories), inferred structure entries (such as diagnosis site, generic drug name), language of text, match type (such as exact, exact but letter case mismatch, fuzzy matched, etc.), text type (TTY, described above), or other fields.

Normalized Entities may be further normalized to reduce known variance in results. For example, in a cancer type normalization, there may be numerous normalization endpoints which reference breast cancer in one form or another that match the selection criteria of the normalization algorithm. A post-processing step to the normalization may be applied which identifies, for example, when a cancer site is designated as breast, and adjusts the final result such that all entries with a breast cancer site share the same cancer site code and same spelling "breast". Other normalized results may include each main cancer site (brain, lung, liver, ovary, bone marrow, etc.), a predetermined catch-all for unknown sites, or known codes which are irrelevant to the normalization results and may be filtered.

Returning to FIG. 5, the Entity structuring pipeline 72 compiles each of the normalized concepts identified in the previous stage. However, given thousands of pages of documentation within an EMR/EHR for a patient, the number of normalized entities that may be identified and resolved during processing may number in the hundreds of thousands. The abstraction process as described above with reference to FIG. 5, may display information about a normalized concept by providing various identified and populated fields. For example, with reference to the sentence "The patient was given Tylenol 50 mg at 10:35 am.," the entity structuring pipeline 72 may encode the following fields:

Text: The entirety of the text ("The patient was given Tylenol 50 mg at 10:35 am.").

Medication: Identifying any medication mentioned in the text (Tylenol). Medications may be brand name or generic name. This field does not include information about the dosage or method of administration.

Active Ingredient: Identifying the active ingredients (acetaminophen) of the medication mentioned using a list such as a search table linking drug names to their active ingredients.

Dosage & Dosage Units: The dosage (50 mg) associated with the medication mentioned. In the above example, identifying that the dosage as 50 mg is fairly straightforward by reading the sentence, but clinical data is often printed in tables with a variety of structures that are not easy to infer. As such, normalizing the dosage and dosage units by separating value 50 into the dosage field and string "mg" or by selecting a known value entry for the milligram units within a list may be preferable.

Document & Page: The document and page where the text is found (Progress Note 01_01_01.pdf and page 3).

UMLS_CUI: The CUI field (C0711228) of the UMLS entry corresponding to the medication. The UMLS is a list of medical concepts and the UMLS_CUI refers to the CUI field, which is UMLS' universal identifier. UMLS is comprised of a number of independently maintained clinical dictionaries and ontologies (such as those for cancer diagnosis & treatment, dentistry, veterinarian medicine, etc.). That is, the CUIs are universal to UMLS, and there is only one CUI for Tylenol across all of its constituent dictionaries that enables UMLS to unite all of these disparate sources.

UMLS_AUI: The AUI field (RXNORM #4459) is the dictionary-specific identifying code of the UMLS. Where the CUI is universal, and has the same entry across all included sources, the AUI for Tylenol will have different AUIs for each dictionary that it has an entry in.

Various fields, such as UMLS_CUI, UMLS_AUI, Medication, and Active Ingredient may each be determined through the entity normalization process by exploring the links to each of the Entities. The other fields, such as dosage, dosage units, date/time administered, document, and page may not be determined through the normalization process. Instead, these other fields are provided to a Relational Extraction MLA for extracting this information from the surrounding context or document information (such as name, number of pages, etc.). For example, a document named Progress Note 01_01_01 may be presumed to have a date of Jan. 1, 2001. Other concept candidates from the document may be referenced to validate the date/time or select the date absent any other validating/corroborating information. For example, the time 11:35 am may have been provided as a concept candidate spatially near the "Tylenol 50 mg" concept candidate. The Relational Extraction MLA may then identify 11:35 am as the time the medication was administered based on the concept candidate time being the next concept candidate in the list, a spatial proximity of the concept candidate, a new application of NLP to the OCRed text string, or any combination thereof. Additionally, a page number may be identified, for example, in a document that has 5 pages by referencing the page number by performing an OCR of text at the bottom of the page or may be extrapolated by counting the number of pages before the page the concept candidate was extracted from. Once each field of the medical data is identified through either the normalization process or the structuring process and the relational extraction MLA, the patient/document may be ready to be classified according to each normalized and structured entity.

Returning to FIG. 5, the post-processing pipeline stage 74 may receive a listing of all the structured entities and generate a response/report. For example, a response may be a formatted into an output divided into several sections, each section relating to, for example, the fields of Diagnosis, Procedures, Radiology, etc., as discussed above. Under a Diagnosis header/identifier, structured entities relating to diagnosis may be summarized with the final normalized entity, information from the entity structuring, and any confidence values generated during the classification and/or ranking/filtering. The response may include all of the sections with corresponding structured entities. The response may be generated and output, such as as a word document, a spreadsheet, or a JavaScript Object Notation (JSON) file with each of the relevant sections and structured entities encoded therein.

The MLA and DLNN algorithms described herein may be implemented using supervised, unsupervised, and/or semi-supervised approaches. Patient/document classification based off of text classification is the general task of processing text and identifying whether it belongs to one of many pre-defined groups (such as the above-referenced medical fields). For example, supervised machine learning methods may be used to classify patients as Male or Female, because many clinical documents exist for patients whose genders are known. Exemplary non-machine learning ways of determining a gender would be to apply a regular expression for "Gender:" in text or "pt is a ##yo X". It would be an exhausting endeavor to create a regular expression for every potential combination of words or characters that gender may be mentioned in text in order to be able to extract it using simple text matching. Instead, a simple heuristic component for classifying a gender may be to determine the ratio of male vs female pronouns in text, under the assumption that references in medical text are almost entirely describing the patient (as opposed to their family members or medical staff, who are occasionally mentioned as well).

Similarly, a supervised machine learning method may require that the gender is known or provided for some batch of patients. The machine learning method may then extract signals or features from the text that are indicative of the gender. At that point, a Naive Bayes MLA may be utilized to, for example, identify the ratio of male vs female pronouns. The Naive Bayes MLA may determine the frequency of every word that occurs in any clinical document occurs in the male documents vs how often the same words occur in the female documents in terms of probability (such as 'he' is 2% of words in male documents and 0.1% of female documents). Once trained, for each new document to be classified, the Naive Bayes may use the generated probabilities/statistics to determine the likelihood that a document falls within the male linguistic probability distribution or the female distribution. A general threshold value or comparison may be applied to determine whichever probability is higher.

While supervised methods are useful when the training dataset has many known values or annotations, the nature of EMIR/EHR documents is that there may not be many annotations provided. When exploring large amounts of unlabeled data, unsupervised methods are useful for binning/bucketing instances in the data set. Returning to the example regarding gender, an unsupervised approach may attempt to identify a natural divide of documents into two groups without explicitly taking gender into account. On the other hand, a drawback to a purely unsupervised approach is that there's no guarantee that the division identified is related to gender. For example, the division may be a between patients who went to Hospital System A and those who did not.

As a result, semi-supervised methods may be the most optimal approach whenever there are a large number of unlabeled or unannotated documents as well as labeled documents in the training set. EMRs/EHRs may be particularly well-suited to this approach, because hospitals take care to note key health information for each patient. For example, considering a practical approach to applying a semi-supervised MLA, presume that an exemplary dataset generates a probability distribution such that "he" accounts for 2% of the words in male patients' documents and 0.75% of female patients' documents. If these estimates were taken over a small number of patients (such as 100 pages of text total), but 80 of these pages are from female patients, the probability distribution may be quite susceptible to noise (erroneous weighing) and may generate wrong or undesirable results.

The unsupervised approach solves this by providing a number of documents from patients whose genders unknown, effectively allowing the MLA to learn something about language in general. Specifically, the MLA determines how frequent "he" may be presented in clinical text in general. If the semi-supervised MLA identifies that "he" only occurs 0.5% of the time, "he" may be occurring unusually frequently in the labeled documents (such as at 2% and 0.75% probability distribution). For example, no ratio of male-to-female patients could balance out to 0.5% given an initial probabilities of 0.75% and 2%. Instead, the MLA corrects for the noise in the data set by applying the information that there were more female patients than male patients and accordingly adjust the probabilities more strongly for the male probability distributions than the female. A scaled probability distribution may indicate that "he" occurs at 0.9% frequency in male patient files and 0.1% in female patient files, so that the average distribution of "he" is 0.5%. The semi-supervised MLA may then accurately apply the heuristic technique as a portion of the classification determination.

Machine learning algorithms and deep learning neural networks tend to provide approximate solutions to any complex problem without a clear set of rules to constrain the problem through. MLA and DLNN are most useful for problems which are too difficult to constrain accurately to a few simple rules/constraints and excel at finding unique solutions to these complex problems. These unique solutions may also include equally unique bugs for edge cases of the unique solution, which may require fine tuning to improve the performance of the MLA by adding better/more accurate/more representative training data, by tuning hyperparameters, or by improving or replacing the MLAs themselves.

In an exemplary model, as described below with reference to FIG. 11, a training feedback loop 142 operates to improve the training data set by improving the annotations of the edge cases and using the improved training data to refine the MLA model itself. For example, an initial MLA trained on an initial data set may be only 75% accurate at its given task. By directly utilizing the MLA in a platform where humans are entering data based on clinical documents for patients, edge cases (erroneous output) may be identified, the annotations surrounding the documents/patients of the edge case may be improved, and the improvements submitted back into the MLA to further train the model to improve accuracy. Regardless of whether the human agrees or disagrees with the machine learning model's prediction/classification, the human takes into account the prediction as well as other information in the clinical documents before making their final annotation. This final annotation is utilized as the "gold standard" by which the MLA should operate and can immediately add the labeled documents and the corresponding annotation to the training data set to improve the results when the MLA is trained in the future. Each edge case that is corrected by a human, even each additional question that a human answers above and beyond the erroneous outputs may directly help the machine learning model answer the corresponding question correctly in the future.

The feedback process may be improved by adding the ability to collect direct feedback from an annotator. For example, if the annotator agrees with the machine learning model's prediction, then it may be presumed that the prediction was correct. Conversely, if the annotator disagrees with the prediction, it may not be clear why the MLA prediction was wrong. For example, the MLA may make an erroneous prediction if the documents were for the wrong person, if OCR errors exist which confounded the prediction, or if the model simply was not sufficiently trained to make a correct prediction from the data in that instance.

Figure 11:
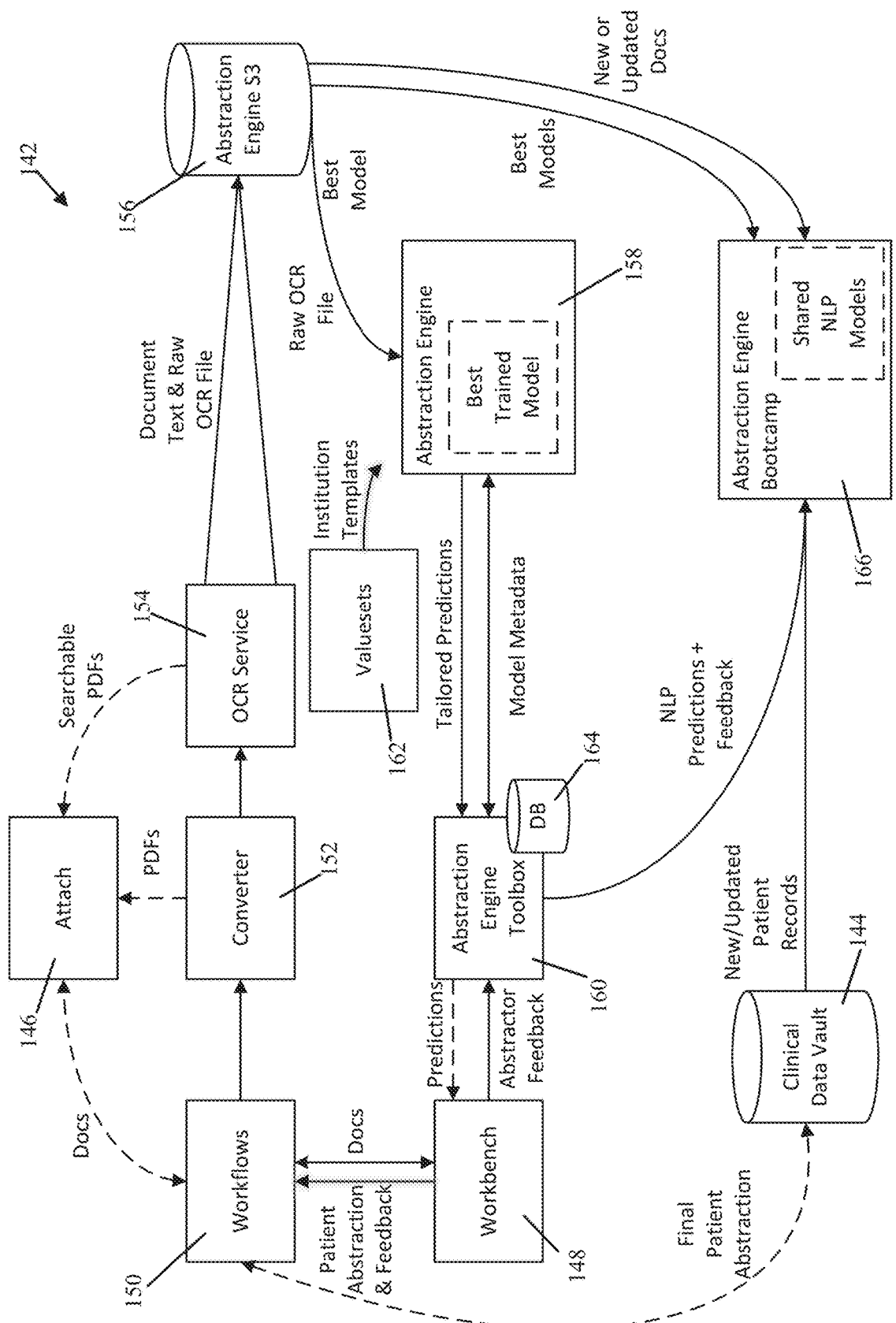
FIG. 11 is an exemplary architecture for implementing an embodiment of the pipeline of FIG. 5.

Staying with FIG. 11, an exemplary system architecture is depicted. In particular, FIG. 11 depicts a scenario in which the system receives documents, for example, from a clinical data vault 144, new documents from an Attach system 146, or corrected documents via the Workbench 148 (introduced below), uploads documents, and posts them to a Workflow 150. Workflow 150 may be a server that coordinates a number of tasks and manages the intake of documents for the intake pipeline described in FIG. 5.

From there, the documents are posted to Attachments 146, for example, another server that stores sensitive files and authenticates all access to those files. Concurrently, a copy of each of the documents is sent to a Converter 152, which patches each document with a viewable image, such as a PDF, of the document. The system calls an OCR service 154, such as Google Cloud Vision or Tesseract, which runs optical character recognition on the documents. Alternatively, if the system determines that the document was already OCRed, a cached copy of the OCR document is retrieved from a database (S3) 156. The viewable image file then is transmitted to the Attachments component 146, which links the original file with the image file. Similarly, a copy of a searchable text version of the document is provided from the OCR service 154 to the Attachments component 146 to combine with the original document and the viewable image from the Converter 152 and, if not previously OCRed, a second copy of the searchable text version is transmitted to the database 144 where it is cached. The Abstraction Engine 158 and Abstraction Engine toolbox 160 components utilize MLA and NLP to generate predictions.

Once the patient documents are processed in Workflow 150, Workbench 148, and then processed through OCR 154, raw OCR information may be pulled from the database. The processing intake pipeline stage for pre-processing and OCR occurs in these servers/processes. The system also may check the database to determine whether improved NLP models have been provided and retrieve any new or updated models. The system then applies the most current NLP algorithms and models to the raw OCR files. In this regard, patient data may be encoded differently depending on the project for which it is being used, so the system may communicate with a service (such as Valuesets 162 in FIG. 11) that includes one or more templates to set forth how the OCR'd data should be abstracted and which values within that data are displayed for each field. Tabular and template extraction may also be contained within the Valuesets database 162.

The predictive data is then tailored for the given project from the tabular extraction applied, and those predictions then are posted to a second database (such as the Abstraction Engine toolbox 164) for use by one or more additional applications. The Valuesets service 162 may specify a global encoding list for all of the concepts related to each of the dictionaries/databases and the internal universal dictionary (such as medical concepts and fields described above). Using medications as an example, Valuesets 162 specifies all of the medication ingredients that may be beneficial for analysis.

By narrowing the search to a targeted list of concepts that are important to identify, overall processing speed of the architecture may be improved. For example, UMLS metadata may be applied to determine that "Tylenol" is a brand name drug, "acetaminophen" is a generic ingredient as described above. When "Tylenol" is recognized as a medication, medication-specific queries may be processed to identify normalization candidates, for example, in the Abstraction Engine toolbox 160. If a query returns that "acetaminophen" is in Valuesets 162 but "eucalyptus leaves" is not, any medication determined to be eucalyptus-based may be ignored by the system.

Workbench 148 may represent a server for maintaining a user interface (UI) to implement a patient record analysis system responsible for managing the flow of information between systems of the instant architecture and/or stage of the processing pipeline. An exemplary high-level description of the UI may include three windows/panes, such as a center pane that allows an abstractor to view patient documents for which the other two panes may display information relating to. A left pane may be configured for entering the abstracted information, including fields (drop-down lists that are populated by Valuesets 162), dates can be entered and subjected to rules for validation (such as DOB must be before date of death), singular fields (such as patient's gender or primary cancer diagnosis), repeatable fields (such as drugs the patient took, surgeries, etc.), fields with subfields (such as medication structured data, cancer diagnoses, etc. as disclosed above with reference to FIG. 6). A right pane may be configured for displaying Abstraction Engine 158 results. The way these are structured is determined by the Abstraction Engine 158 configuration. Category groups fields at a high level and specifies, for example, four of them currently: Demographics, diagnosis, treatments, outcomes. Categories have many fields, which are what the abstractors are trying to enter values for. These fields may also be expanded and collapsed. When expanded, a list of values that the Abstraction Engine 158 predicted for that field (and optionally, a confidence score specified for that value) may be shown. Fields can also have justifications tied to them, which are text snippets that the Abstraction Engine 158 determines best shows why the given value is correct for the given field. Given that many of the predictions are tied to the intake pipeline stages, the text surrounding the identified concept candidate may be provided as the justification.

Workbench 148, the patient record analysis system, may access and/or retrieve patient data from a patient record located in the Workflows component 150, requested from the clinical data vault from the Workflows component 150, or from the patient record including the documents that were stored in the Attachments storage 146. For each document, Workbench 148 may also retrieve the corresponding NLP predictions from Abstraction Engine toolbox 160. Once abstracted, the final abstraction report and data may be transmitted, via Workflows 150, to a clinical data vault. For example, the MLAs may have already provided classifications/predictions for the patient that is being abstracted. The Abstraction Engine server 158 may have already processed all of the documents for the given patient, generated its predictions, and uploaded them to Abstraction Engine Toolbox 160. The Workbench server 148 may then retrieve the patient documents as well as Abstraction Engine 158 predictions for each patient. An abstractor may use an interface of Workbench 148 for manual abstraction. The Abstraction Engine 158 pipeline may be further optimized such that the Workbench interface 148 also includes machine learning predictions for each template's fields and presents them to the abstractors (such as the fields of FIG. 6). Once identifications of relevant metadata for clinical concepts are found in text, Abstraction Engine Toolbox 160 may generate predictions. Once entity normalization have been completed, a report may be generated and provided to Workflows 150 for storing in the clinical data vault, for example, in a text file or a JSON format. This information may be populated for every medication that is identified in the patient's clinical documents and may also be provided to the Abstraction Engine Toolbox Service 160 for storing this information in a protected database. Other services can then query Abstraction Engine Toolbox 160 by Patient or by Document and determine which clinical predictions Abstraction Engine 158 has made. Abstraction Engine S3 156, Abstraction Engine 158, Abstraction Engine Toolbox 160, and Valuesets 162 together implement the parser, entity linking, and entity normalization intake pipelines stages.

As mentioned above, the system periodically checks to make sure that the NLP/MLA models being used are most up-to-date (such as elements 76, 78, and 80 from FIG. 5). The system may include a Bootcamp subroutine 166 for evaluating and updating the NLP and MLA models. In this subroutine 166, the system retrieves clinical record documents from the clinical data vault 144, such as based on one or more unique user id's, on clinical features common to one or more patients, or any other criteria. The subroutine also may communicate with the Abstraction Engine S3 database 156 to retrieve the raw OCR files corresponding to each of those documents, as well as the current NLP model. The system further may retrieve abstractor feedback (such as the feedback loop's erroneous result corrections/annotations) from the toolbox 160. Each of these inputs may be used to execute a training script to verify or update the NLP model. At that point, metadata relating to the updated model may be communicated to the Abstraction Engine toolbox database 164 (such as for later human inspection, model or data provenance, and/or long-term metrics). Workbench 148 supports the ability for abstractors to tag Abstraction Engine's 158 incorrect predictions with a predetermined set of issues (such as documents are from wrong patient, OCR errors, wrong entity linked, correct concept candidate, wrong entity linked, correct concept candidate but hypothetical reference in document cannot be construed as haven taken place, etc.). For example, in the case of patients whose predictions are incorrect because 'Documents are for wrong patient', the Abstraction Engine Bootcamp 166 may ignore these patients when training future MLAs to understand gender or may instantiate a specific training phase to train the current MLAs to predict which patients have documents from multiple patients and exclude from training and/or flag all patients which have documents from wrong patient for independent abstraction.

Similarly, other tags such as 'Bad prediction due to OCR error' may be applied as feedback on a given OCR software/service, which means the system can implement various OCR services and use abstractor feedback to determine the highest quality OCR service 154 from various competitors. Abstraction Engine toolbox 160, Workbench 148, and Workflows 150 together implement the Entity structuring and post processing intake pipeline stages.

Workbench 148 facilitates and incorporates human abstraction by providing prediction justifications and confidence metrics alongside the predictions. A number of issues arise when providing an abstractor with only a single list of possible answers and corresponding confidence values. For example, an abstractor may not be provided with any reasoning about how the predictions or confidence values are calculated, or it may not be clear when an abstractor should trust the NLP models and when they should take a deeper look into the patient record because it is difficult to know what confidence level is needed before an output needs to be verified for accuracy. Instead of making this decision the sole responsibility of the abstractor, Abstraction Engine 158 is designed to provide justifications for its predictions in the form of textual contexts that are determined to indicate that a prediction is correct.

Following the example of structuring a full medication entry that included a Text Context field (FIG. 6), additional processing may determine whether the fully structured concept is a positive mention (such as it is not related to a family member's previous illness or treatments, it is not a hypothetical treatment proposed by a doctor, it is not a diagnosis unrelated to the patient that happens to be mentioned in supplemental literature, etc.) and maintaining links to text context may be a useful justification to the positive mention. This determination may be processed through other text classification algorithms that use the contextual information to identify whether the concept mention is positive or negative. For example, the simplest implementation may include a pattern-based system configured to ignore diagnoses in contexts such as "{mother/father/sister/etc.} has a history of {disease}." While these phrases may be considered in the NLP algorithm itself, error checking may involve repeating the process in low confidence predictions, or providing additional algorithms with text classifiers that utilize the additional textual context. Another embodiment may involve aggregating all of the mentions of a primary cancer site which may also include all or some of the textual contexts for those mentions, which can provide the abstractor with confidence that the prediction was correct without manual intervention.

Figure 12:
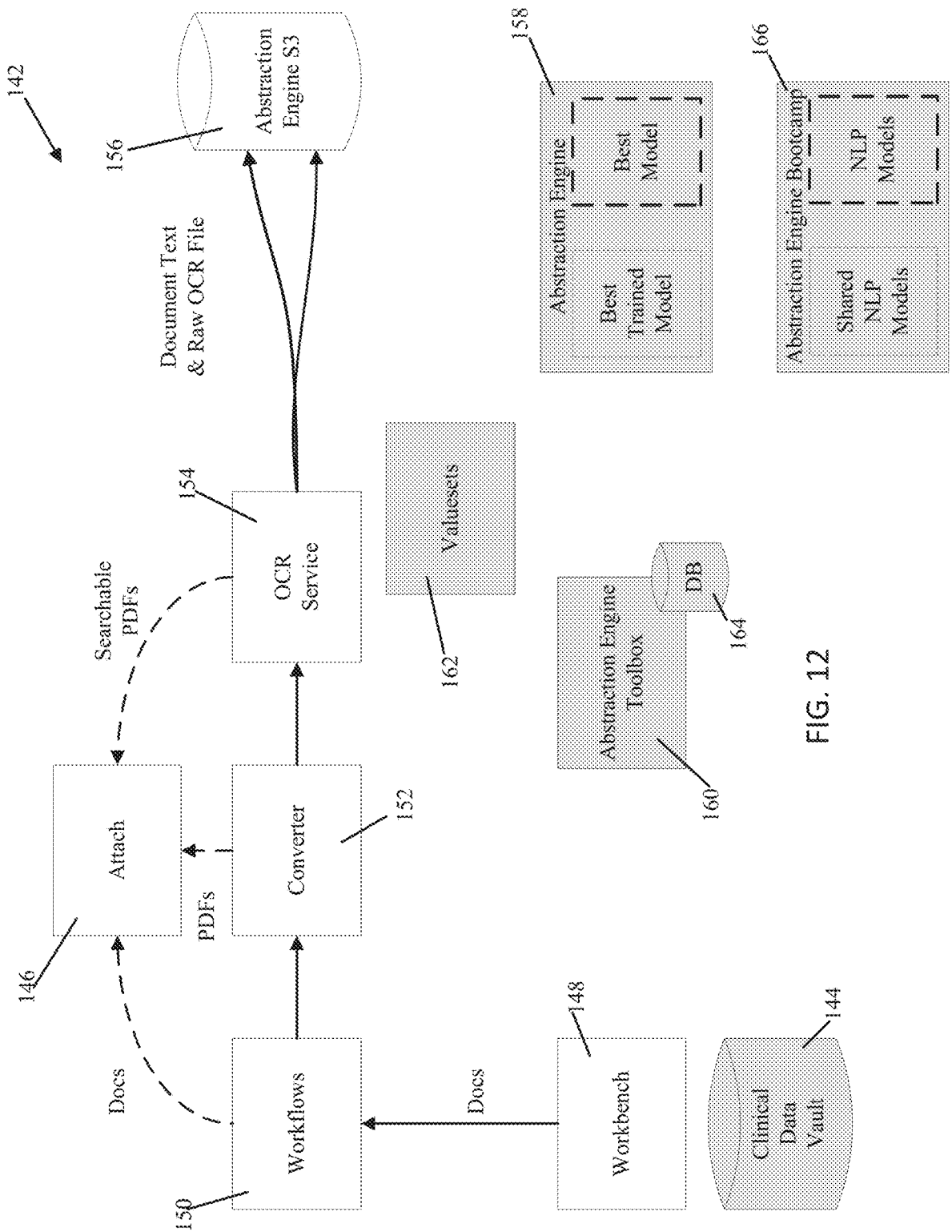
FIG. 12 is an exemplary representation of the patient upload portion of the architecture.

Turning now to FIG. 12, a patient upload process of the instant architecture is disclosed. In particular, this figure illustrates a process in which Patient documents may be uploaded by Extract, Transform, Load (ETL) Tool or a Q-Manager. Q-Workflows 150 may post the documents to Attachments 146. A Converter 152 may patch the documents with viewable PDFs. OCR 154 may run either an OCR service such as Google Cloud Vision or Tesseract to OCR documents or, if the document was previously OCRed, it may retrieve a cached copy of the OCR. The system then may receive a response from S3 156 instead of OCRing it again. OCR 154 may patch the documents with a searchable text version of the PDFs, and OCR 154 may cache the raw OCR files to the Abstraction Engine S3 bucket 156.

Figure 13:
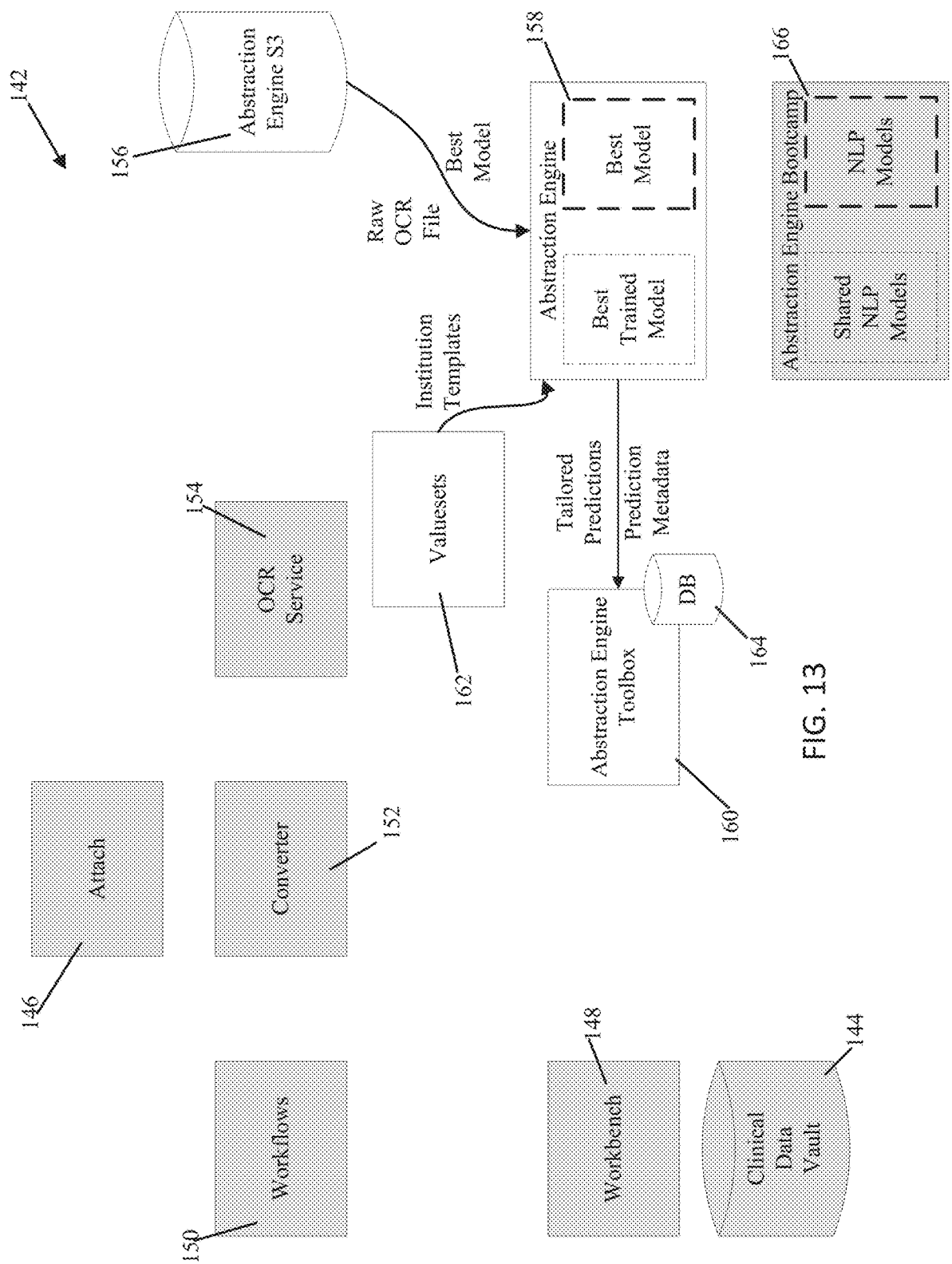
FIG. 13 is an exemplary representation of the prediction generation portion of the architecture.

Turning now to FIG. 13, a prediction generation process of the instant architecture is disclosed. In this aspect, once the patient documents are processed, the Abstraction Engine 158 may pull raw OCR files from its S3 bucket 156, check S3 156 for improved NLP models and pulls them if necessary, run the documents through its current NLP pipeline and models, pull project-specific templates from Valuesets 162, tailor its final predictions for the given project, and post those predictions and related metadata to the Abstraction Engine Toolbox 160. In this regard, patients may be encoded differently in each project, so Valuesets 162 may be a service that coordinates project encodings (such as which fields are abstracted, which values are displayed for each field).

Figure 14:
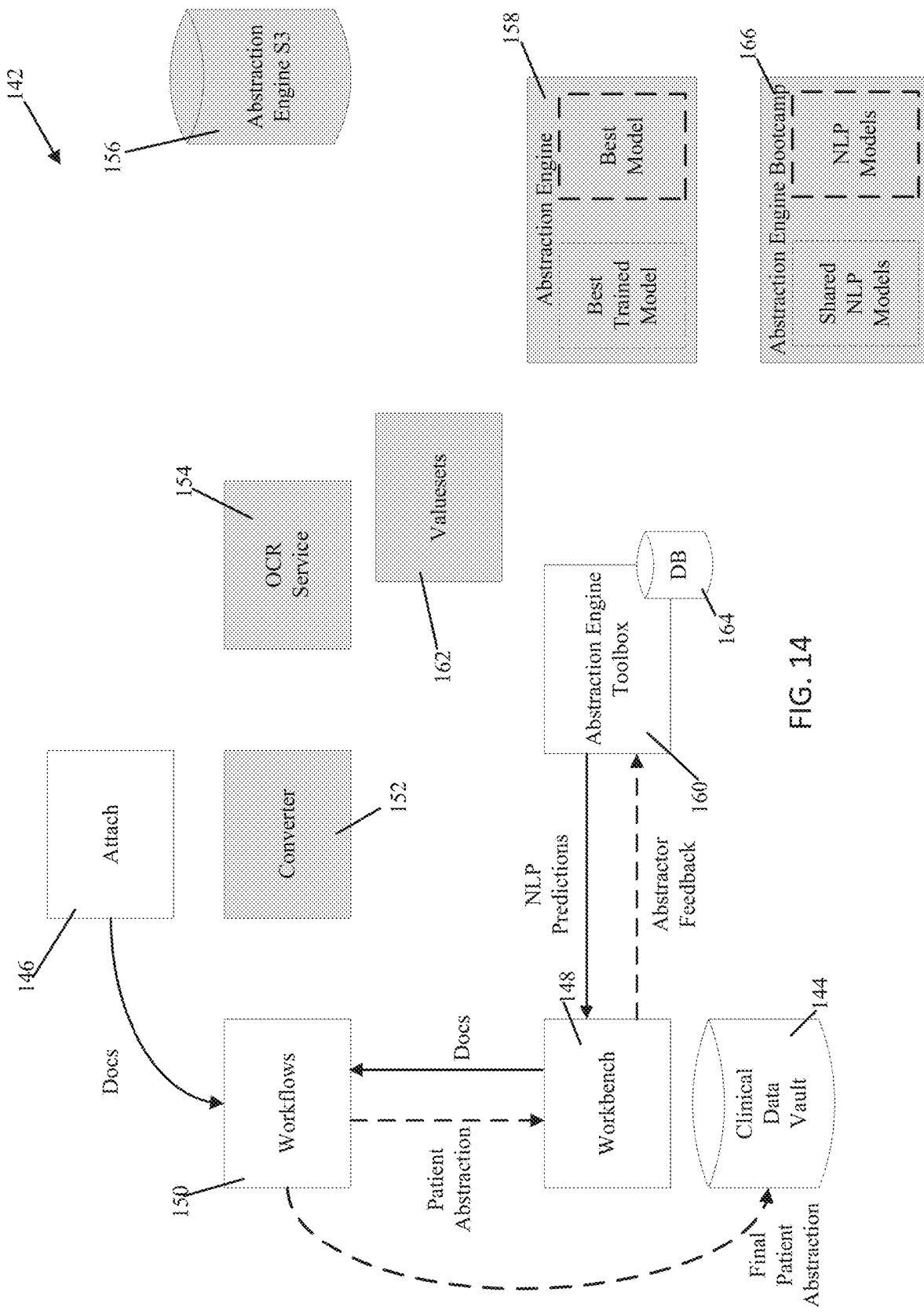
FIG. 14 is an exemplary representation of the abstraction portion of the architecture.

Turning now to FIG. 14, an abstraction process of the instant architecture is disclosed. In this aspect, when a Q-Workbench user loads a patient, Q-Workbench 148 may pull the patient record from Q-Workflows 150 (Q-WF), including patient documents which are passed from Attachments 146 through Q-WF 150. Q-Workbench 148 also may pull the corresponding Abstraction Engine predictions from Abstraction Engine Toolbox 160 (if the predictions are available). The abstractor may abstract data field by field and pass patient data to Q-WF 150. Patients may provide direct feedback about specific NLP predictions, which will be passed directly to Abstraction Engine Toolbox 160. And the abstractor may submit the final abstraction report and data makes its way through Q-WF 150 to the Clinical Data Vault 144.

Figure 15:
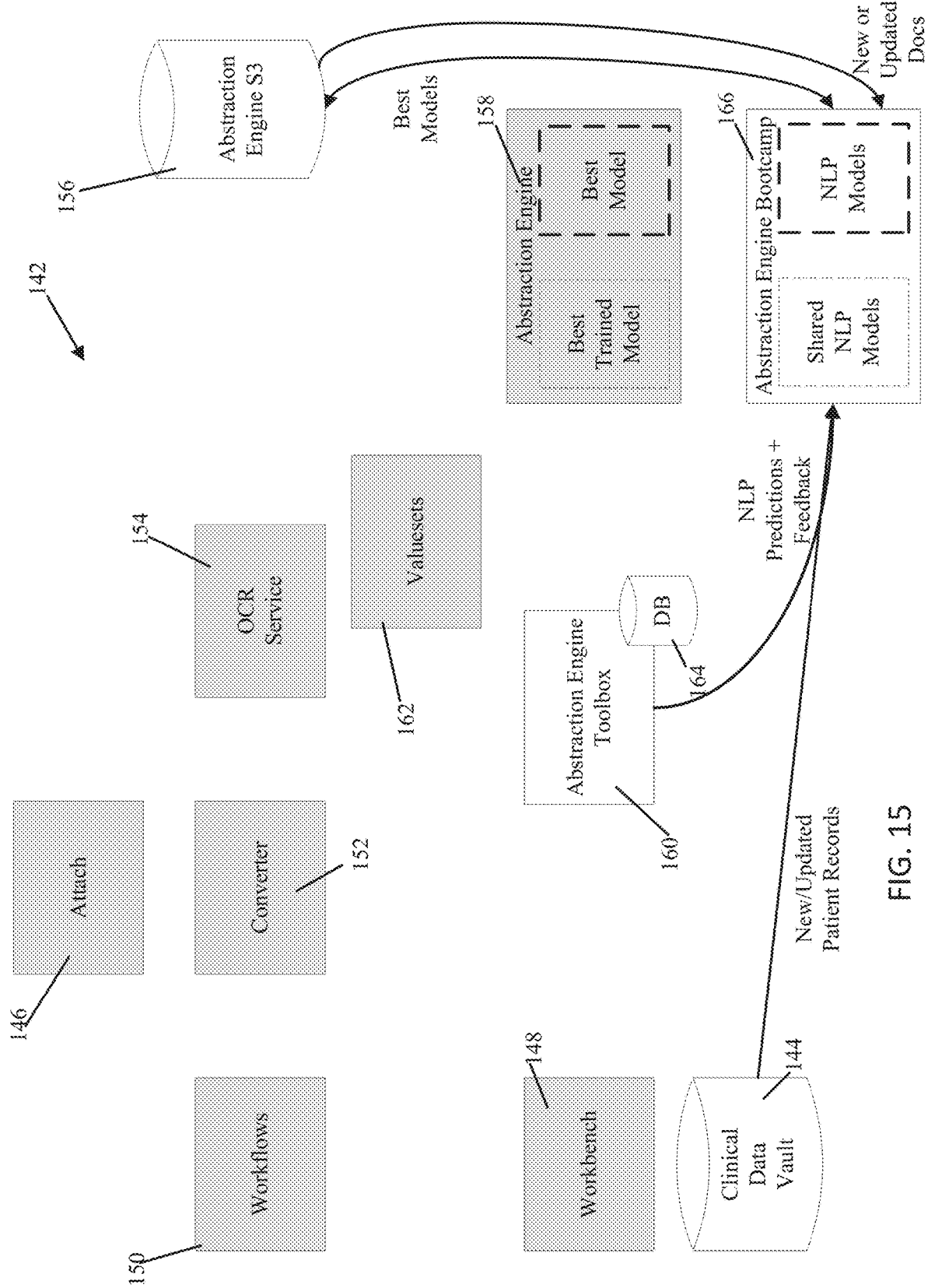
FIG. 15 is an exemplary representation of the feedback and training portion of the architecture.

Turning then to FIG. 15, a feedback loop and training process of the instant architecture is disclosed. In this aspect, the Abstraction Engine Bootcamp 166 may periodically update Abstraction Engine NLP models. Specifically, the Abstraction Engine Bootcamp 166 may be initialized by a script or a periodic update protocol. The Abstraction Engine Bootcamp 166 also may pull: clinical records from the Clinical Data Vault 144 for a list of patient UUIDs specified by script/protocol, the raw OCR files that correspond to each of these patients' documents from the Abstraction Engine S3 bucket 156, and existing NLP models from S3 156 (some models can be trained multiple times and improve over many iterations of new data). Abstractor feedback may be pulled from Abstraction Engine Toolbox 160 into Abstraction Engine Bootcamp 166 for additional training info. The Abstraction Engine Bootcamp 166 may execute its training script and post NLP models to S3 and also post model metadata to Abstraction Engine Toolbox 160 for human inspection, model/data provenance, and long-term metrics.

The systems described above may have multiple uses that are beneficial to clinicians and researchers involved in the treatment of diseases, research into diseases, and data analysis involving disease. One example is in the field of clinical trials. A clinical trial is a research study to determine the safety and efficacy of a drug, device, biologic, or other potential treatment. Clinical trials often have inclusion and exclusion criteria, whereby a patient must meet all of the inclusion criteria and not have any of the exclusion criteria in order to enroll in the study. Many clinical trials have specific criteria that can be determined only after close examination of the medical record. For instance, an example of inclusion criteria for a study of chemotherapy of breast cancer subjects might be postmenopausal women between the ages of 45 and 75 who have been diagnosed with Stage II breast cancer. An exclusion criterion for this study may include a positive identification for abnormal renal function, if, for example, one or more of the drugs used as treatment in the study are nephrotoxic. A medical institution, such as a hospital, may have many patients who are eligible for the study, but require the system described above in order to parse their EHR in order to prepare a list of patients who are eligible to participate in the study.

Another example relates to the development of synthetic control arms for clinical trials. In a clinical trial, a group of patients (called the "control group") receives standard of care treatment while a second group (the "experimental group") receives an experimental treatment (such as a study drug). Often, a study is "blinded" meaning the patients who enroll in the study do not know if they are part of the control group or the experimental group. It can be difficult to recruit patients to clinical trials because many patients wish to ensure they are part of the experimental group. An institution may utilize the systems and methods described herein in order to create a list of structured data from each patient in the EHR who meets the inclusion/exclusion criteria. By leveraging the existing data of patients who do not qualify for the clinical trials, a propensity based model may supplement the clinical trial data as the control arm of the study. These patients may be considered the control group, and their health data as captured in structured format may be utilized as the control arm of the study. In this way, a separate enrolled control group is not needed for the study, and the patients who enroll may all be made part of the experimental group.

Another example relates to data analysis of an institution's EHR. Many institutions, such as hospitals, retain patient health information in free text that is not easily searchable for patterns in treatment or outcomes. Using the systems above, institutions may be able to create structured data sets with data elements that permit the institution to conduct sophisticated data analysis to look for data trends. Such trends may indicate best practices in particular departments, or may indicate areas of concern that require the institution to conduct further investigation. For example, the institution may utilize the systems and methods described above in order to determine which patients are being prescribed which medications at which dosages. The systems and methods may be used periodically (for instance, on a quarterly basis), to analyze utilization rates. As another example, the institution may utilize the systems and methods described above in order to characterize the outcomes of patients with respect to treatments which they have been prescribed and undertook while under the care of the institution. The analysis may be conducted in a way that the structured data generated by the systems and methods described above omits certain data elements in order to ensure that the structured data is de-identified or that protected health information is securely maintained, encoded, or removed. For instance, name, address (all geographic subdivisions smaller than state, including street address, city county, and zip code), elements (except years) of dates related to an individual (including birthdate, admission date, discharge date, date of death, and exact age if over 89), telephone numbers, fax number, email address, Social Security Number, medical record number, health plan beneficiary number, account number, certificate or license number, any vehicle or other device serial number, web URL, Internet Protocol (IP) address, finger or voice print, or photographic image of the patient, may all be omitted from structured data fields. Alternatively, or in addition, the resulting data may be run through a statistical system to ensure there is a very low chance it contains identifiable health information.

In another example, an institution may utilize the systems and methods described above to conduct automatic quality checks on the information contained in its medical record. For instance, the institution may use the systems and methods to compare information in one section of the medical record with information in another section of the medical record to ensure consistency between the records in each section. As an example, imaging reports on cancer tumors can contain radiology information about the tumor (such as its size), while a radiology report prepared by a physician may also contain similar information. The systems and methods described herein may be used to ensure that the imaging report (for instance, the tumor diameter is 2 cm) is consistent with the information as the radiology report (for instance, the tumor diameter is 2 cm). If the information is different, an alert may be triggered to have a clinician review the record further.

In another example, other types of records could be used instead of patient records to create a structured set of data from unstructured information. One type of record that could be analyzed using the systems and methods described above is a scientific journal publication. Many publications disclose information about new and potentially promising treatments in cancer and other diseases. Other publications disclose information about existing treatments that may be useful for newly indicated diseases. The systems and methods described herein may be used to automatically generate a list of structured data from a scientific publication (for instance, it may generate a list of structured data indicating that a certain drug is effective at a certain dosage for a certain class of patients). The list of structured data may be combined in a knowledge database comprising other similar lists of data.

In another example, the systems and methods described herein may produce structured data that can be aggregated, and the results of the aggregation may be analyzed for comparative purposes. One exemplary use is for population health purposes. For instance, the systems and methods described herein may be used to compare aggregated structured data from one institution with aggregated structured data from another institution or another group of institutions. Such comparison may be useful when determining medication utilization rates; duration of inpatient stays; rates of readmission; types and frequencies of diseases, such as cancers; or other indicators. As another example, the systems and methods described herein may be used to compare aggregated structured data from one geographic area with aggregated structured data from another geographic area. Structured data from an institution or a geographic area may be aggregated using methods known in the art.

In exemplary embodiments, processing of the electronic document capture may be performed on the mobile device 10 or may be sent to a cloud server to reduce the demand on the mobile device's battery and processing resources. For example, the mobile device may obtain an electronic data capture and provide an image of the capture to the cloud server for processing according to the steps disclosed herein. Alternatively, the mobile device may obtain an electronic data capture, perform region capture, and perform OCR on the capture to extract text from the captured region. The mobile application may then provide only the extracted text as well as text identifiers to the cloud server for processing. Exemplary text identifiers may include the Form identifier or document identifiers discussed above as well as a region identifier which identifies which region the extracted text corresponds to. In each of the above embodiments, the cloud server may return the extracted patient information, such as patient name, diagnosis, treatment, or sequencing information, to the mobile application for display and verification by the user.

In one embodiment, the application may include error detection of the electronic document capture. For example, the application may detect that an electronic data capture is of poor quality, and request that the user rescan the page. Such quality detection may be performed by evaluating character quality, for example, comparing density of the solid lines or the fuzziness of lines, checking the whitespace around perceived collection of words for artifact detection. In another embodiment, the application may detect that a page of the document is incorrectly scanned (such as the user either scanned the wrong page of the correct document or a page from a different document). Exemplary detection may be performed by comparing the expected layout of the page (arrangement of document features in the predefined model) with the electronic document capture. For example, if a table is present in the feature list of the identified document, but is not located in the electronic document capture at the expected page, a general error may be flagged to indicate to the user that the expected page was not captured. Furthermore, features which are tagged as optional may be ignored during form verification if they are not present.

Certain error detection may not be easily performed. For example, genes have a plurality of possible variants and each variant further has possible representations. As discussed above, redundant information stored in multiple features of a report, or even report appendices, may be referenced to provide a more robust error detection. However, it may not be possible to automatically detect when a genetic variant is an error from OCR or not.

This problem may be resolved by cultivating a growing set of knowledge and insights around genetic variants and their related attributes. For instance, the application may be able to programmatically differentiate valid vs. invalid variants (correct: EGFR, incorrect: HFGR) by querying a genetic variant database for observed and classified variants for each gene. A database may store knowledge and insights around genetic variants and their related mutation effects currently consists of both internally managed and externally sources, for example, COSMIC (the Catalogue of Somatic Mutations in Cancer), NCI's Clinvar, or gnomAD (the Genome Aggregation Database). This reference data may be used to classify a genetic variant according to data elements such as over or under expression or other deviation in gene expression counts, single nucleotide variants, copy number variants, or coding mutations and fusions. Additionally, various other classifying attributes may be found in the set of knowledge and insights, for example, the chromosome on which the variant was detected, whether a variant is therapeutically actionable, or if it is germline. By using a combination of the redundant features in the electronic document capture and reference data sets, a variant identified in source documents by the application can be evaluated for validity.

In one aspect, the application or a cloud server in communication with the application may query the database via its API to validate whether a recognized gene and variant combination is valid/known or if it is actually an unrecognized variant, an OCR introduced error, or if the unknown combination originated from the clinical documentation and/or text. Known genes and variants have matches, unrecognized variants may not have matches or one that has not been identified, sufficiently classified, or expertly-curated by the scientific community. An OCR error, however, results from imperfect technology for identifying and extracting text from images and/or documents.

Turning to FIG. 16, the user may validate the information captured from a document (such as the document of FIGS. 4A-B) by confirming the patient details are correctly populated in the fields and initiating a query of the patient cohort. For example, the application may include a review interface 170, through which the physician may confirm that the name populated in text field or drop down 172 is the patient's and is spelled correctly, the diagnosis in text field or drop down 174 is the patient's and is spelled correctly, the collection date of the report in date field, text field, or drop down 176 is the report's, and each of the gene identifiers and corresponding variants in fields 178A-C are consistent with the report data. In the event that the captured information is inconsistent with the document from which it was captured, the application may permit manual editing of that information. For example, if the patient name was captured as "Jane A. Dot," tapping or pressing and holding the patient name field may open an editor permitting the user to make the necessary changes. Similarly, selecting a gene identifier icon, such as the oval in any of fields 178A-C may permit the user to modify the mutated gene identified by the MLA in the event it does not match the captured document. Selecting that icon may open a search dialog box and a keyboard on the mobile device in order to receive user input of the specific mutation. If the correct gene was identified as mutated, but the specific variant within the gene does not match that listed on the document, the user may tap or press and hold the portion of field 178A-C outside the oval. Doing so may open a similar keyboard as for the gene identifier. Alternatively, the application may open a list of possible variants for the identified gene, the list being scrollable in the event that its full contents do not fit on the screen all at once. It should be understood that suggested field types above, including text, drop down, or date are merely representative of the types of fields that may be implemented and should not be construed as limiting each respective field to those types as disclosed above.

A button or gesture may be used to add a field to the data which may have been omitted by the extraction process above. For example, the user may press and hold on the blank space below the last entry to cause a new field to appear, or the user may place a finger on two consecutive fields and spread them apart to cause a new field to appear between them. The newly added field may appear at the bottom of the list and the user may drag and drop the field into the appropriate place on the application interface 10. The user may confirm the information is correct by selecting button 180 or by initiating a corresponding gesture (such as using three fingers to swipe interface 170 to transition to the next window of the app). Upon validation of the information, the application may also store a copy of the data (after deidentification and/or removal of protected health information) to include in future reports. New fields and updated fields may be processed again for entity linking and normalization to ensure that each field is accurately curated for generating the query and storage.

The initiated query may be generated by extracting the data from each field of the application and generating a query with the extracted data. For example, each field may include both the text that has been confirmed by the physician and the entity linking data identifying the match to a concept in the medical dictionary as described above. The fields may be added to a container, object model used by the underlying databases, a nested database/dictionary, or other format before encoding and transmission. Transmission may be received and processed at an endpoint of a cohort repository and engine for processing patients and generating the cohort report.

In another embodiment, the initiated query may be received at a database storing aggregate information from patients of one or more physicians. Fields of the query may be extracted and processed by the database to identify a group, or "cohort", of patients in the database who are similar to the physician's patient. Both the text and the linked entity may be stored to ensure the medical concept/ relevance of each entry is accurately recorded. Similar patients having features matching one or more of the features included in the query may be identified and added into a cohort of similar patients. For instance, the initiated query may include a gene identifier that reflects a genomic mutation present on the patient's NGS sequencing report or other document which was initially image captured. A gene identifier may be a gene name, abbreviated gene name, or another label that indicates a specific gene. The cohort of similar patients may be then selected, at least in part, by identifying those patients in the database of aggregate patient information with the same genomic mutation. For example, if a patient's next-generation sequencing report indicates that the patient has a BRAF mutation, the database of aggregate patient information may be queried to identify all patients in the database whose records indicate they also have a BRAF mutation.

The medical information of the cohort of similar patients, or summary analysis thereof, may then be provided to a report generator for processing to identify trends of the patients' case histories during diagnosis and treatment and generate a cohort report. The cohort report may be displayed to the physician, for instance on a screen of the mobile device 10.

Figure 17:
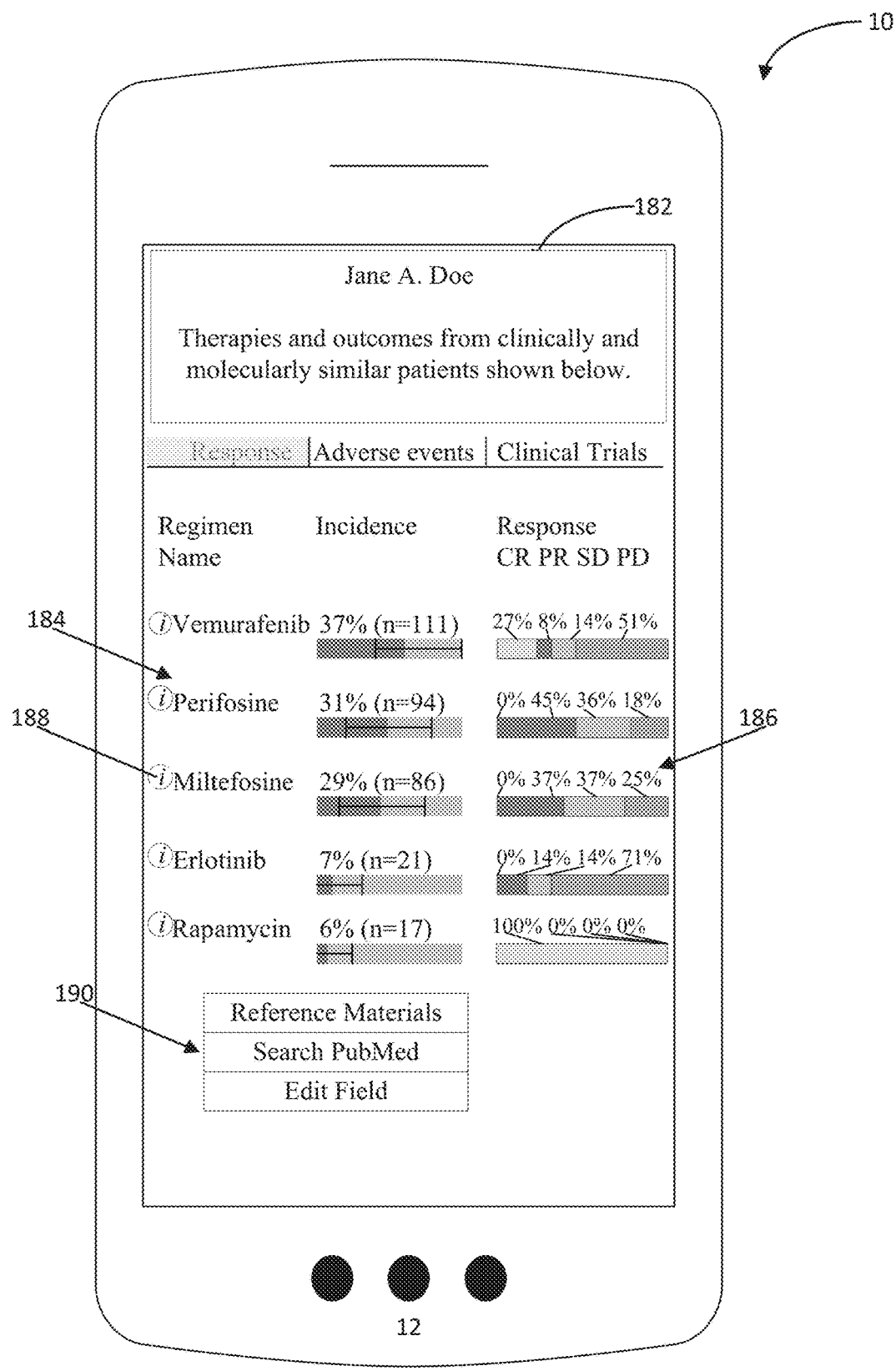
FIG. 17 is a depiction of a first cohort reporting screen of the application that includes one or more treatment regimens administered to patients in the cohort, along with relevant response data for each regimen.
Figure 18:
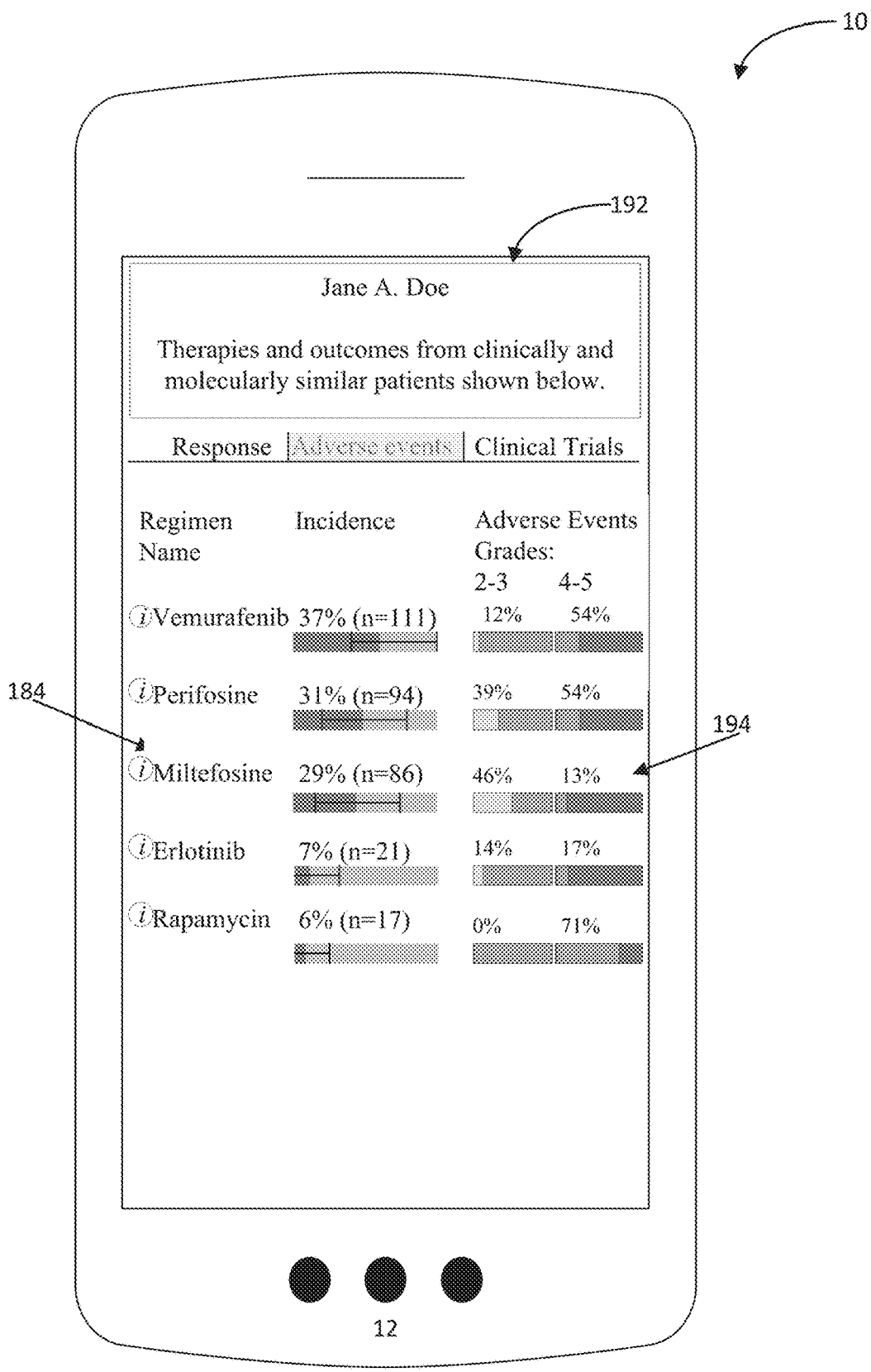
FIG. 18 is a depiction of a second cohort reporting screen that includes the treatment regimen(s) of FIG. 17, along with relevant adverse event data for each regimen.
Figure 19:
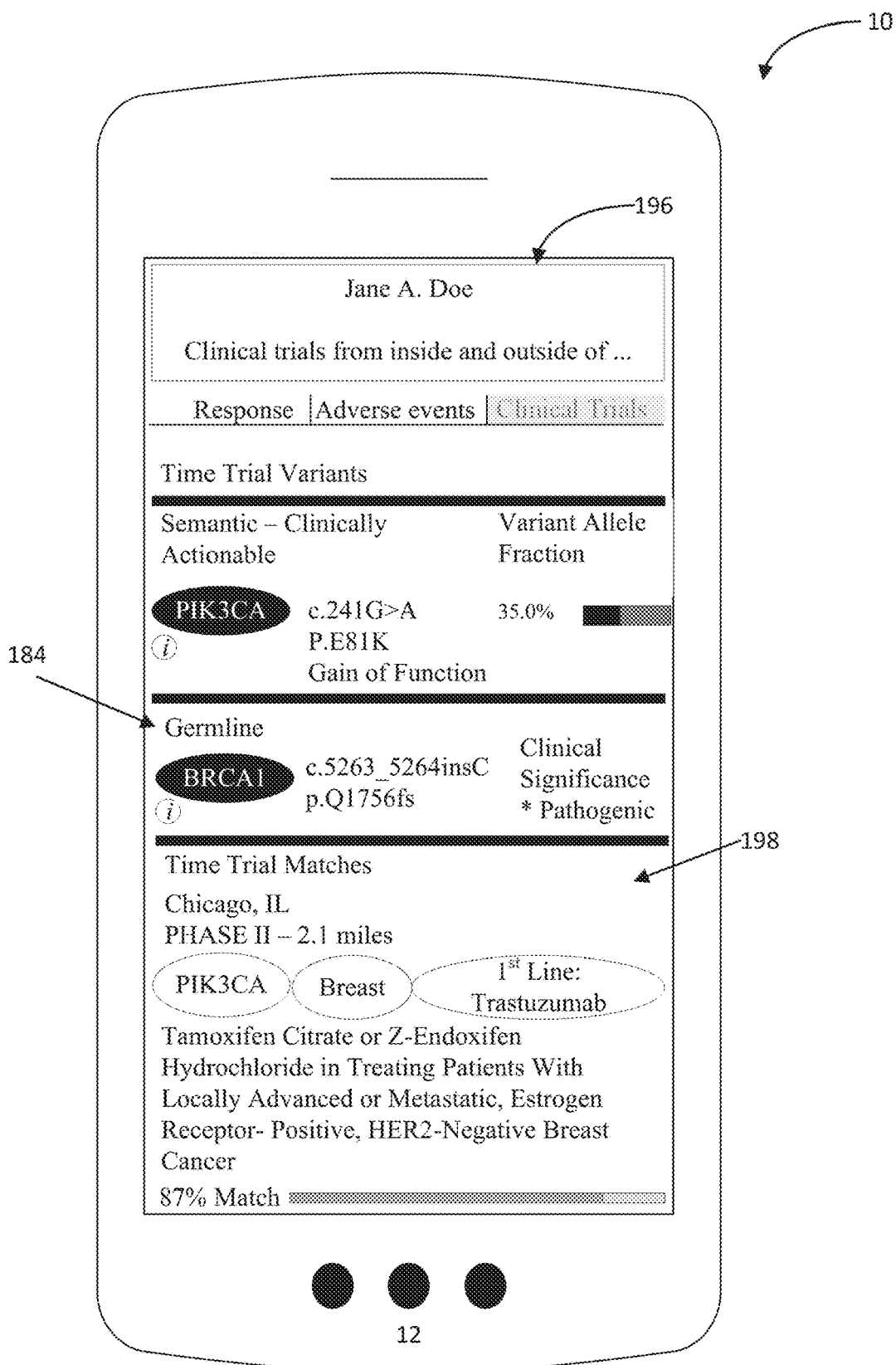
FIG. 19 is a depiction of a third cohort reporting screen that includes potential clinical trial matches.

As seen in FIGS. 17-19, the application may display the cohort report of summarized medical information, which that may help the physician make a treatment recommendation to the patient. When the summarized medical information supplements the information on the initial report, it provides new information to the physician, not present in the initial report, which can help the physician make a more informed treatment decision that may result in improvements to the patient's care, such as improved patient outcomes and greater value of care. FIG. 17 depicts a first cohort report 182 including summarized medical information about the cohort. The summarized medical information includes one or more treatment regimens 184 administered to patients in the cohort, along with relevant response data 186 for each regimen. FIG. 18 depicts a second cohort report 192 including the same treatment regimens 184 as in the first cohort report 182, this time with summarized medical information including relevant adverse event data 194 for each regimen. FIG. 19 depicts a third cohort report 196 depicting summarized medical information in the form of potential clinical trial matches 198 for the patient. Each of these cohort reports are discussed in greater detail below. It should be understood that the types of summarized medical information detailed in FIGS. 17-19 are exemplary, and other types of summarized medical information of the cohort may be presented to the clinician, such as immunotherapy results, radiology imaging results (for instance, the average progression of tumor size in patients in the cohort), pathology imaging results, other imaging results, outcomes information (such as survival information), medical billing information (for instance, the cost of care for patients in the cohort), etc.

After data has been validated by a user (a clinical data abstractor, nurse, physician, etc., that has ensured that a patient's information has been accurately extracted from the electronic document capture of one or more patient reports), the extracted patient information may be stored in a common and structured data format either on a mobile device or in the cloud. An example of a structured data format includes FHIR, OMOP and/or other priority data models that support the representation of numerous attributes (such as demographics, diagnosis, treatments and outcomes, genetic testing, assessments and labs, etc.). This structured data may then be shared back with a health system's EMR or EHR as part of a patient's record or with certain third party applications that support the ingestion of this type of data (such as Apple's HealthKit, ResearchKit, CareKit, or internal proprietary format for each database, etc.). More than one database may receive the structured data or a relevant portion thereof. For example, a patient cohort database may receive all of the patient information while a genetic database may only receive the genes expressed by the patient, the diagnosis of the patient, and/or other patient information also included in the genetic database. The structured data may also be provided to a master patient index which may identify if the patient already has entries from prior interaction with the database through either the application or another partnered institution. The new information may be associated with the already existing patient data or if no matching patient is found a new patient may be added. Other exemplary databases include variant databases to store genetic variants, or clinical trial management systems and databases which track patients who are undergoing treatment as part of a given clinical trial. A notification may be provided to the user spanning multiple different delivery mechanisms including a direct push notification to their mobile device, an SMS or text message sent to their mobile device, an in-application notification as part of the application user interface and/or via an accompanying email that may be sent to any associated email address corresponding to their valid user profile. An analytics module may be present and connected to any of the above databases. The analytic module may be the same as described in U.S. Provisional Application No. 62/746,997, incorporated by reference in its entirety, including the analytical tool that enables the oncologist to explore prior treatment responses of patients that have the same type of cancer as the patient that the oncologist is planning treatment for in light of similarities in molecular data between the patients. Furthermore, the cohort analytics identifies different cancer state filters to be applied to the system database thereby changing the set of patients for which the system presents treatment efficacy data to explore effects of different factors on efficacy to lead to new treatment insights like factor-treatment-efficacy relationships. To further the pursuit of new cancer state-treatment-efficacy exploration and research, in at least some embodiments it is contemplated that system processors may be programmed to continually and automatically perform efficacy studies on data sets in an attempt to identify statistically meaningful state factor-treatment-efficacy insights. These insights can be confirmed by researchers or oncologists and used thereafter to suggest treatments to oncologists for specific cancer states. Trends, outliers, insights, and other metrics may be analyzed and stored for later use. Additionally, metrics may include pathogenicity of variants, genomic phenotypes, organoid response to treatment in a laboratory for efficacy calculations, radiomic and pathomic features from an imaging lab, tumor mutation burden, microsatellite instability status, immunological target expression, resistance risks, immune system infiltration, PD-LI expressions, as well as any trends, outcomes, and insights that may be made between them. These metrics, and more, may be provided to the cohort report below for inclusion as additional data. Additional data may be include general NGS medical information or field specific NGS medical information such as oncological NGS medical information for cancer patients. Oncological NGS medical information may include a diagnosis of cancer, metastasis, or other diagnosis, types of treatments including medications and therapies, duration and dosing of treatments, and for tumors, the tumor and/or patients non-tumor molecular structure, genes, variants, fusions, copy number counts. General NGS medical information may include the "normal" genome of a patient molecular structure, genes, variants, fusions, or copy number counts. General NGS medical information may include any details which may be shared between NGS reports for differing illness, disease, and cancers.

FIGS. 17-19 detail different embodiments of the cohort report. FIG. 17 is one aspect of the cohort report and may feature particular treatment regimens 182 which have been prescribed to similar patients, how frequently the treatment occurs in the subset of similar patients (the "incidence"), and a visual or numerical representation of the patient responses to the treatment 186. Treatments may include singular drugs, therapies, or combinations of drugs and/or therapies. For example, while FIG. 17 displays five separate regimens comprising singular drugs (vemurafenib, perifosine, miltefosine, erlotinib, and rapamycin), in another instance, a regimen may comprise a combination of two or more of those drugs, or one of those drugs plus radiation or another therapy. In certain embodiments, combinations of drugs and/or therapies may be difficult to display in one line. In such cases, the combination may be terminated early with an ellipsis and the user may expand the combination by selecting it in the application. Upon selection, the corresponding entry may resize to display the full combination. The display of one or more of FIGS. 17-19 may include an information icon 188 next to one or more of the treatment regimens, the selection of which may launch a web browser on the mobile device 12 or another screen in the application 10 to provide more information about the selected regimen. Alternatively, the text of each regimen or the field or row in which the regimen is shown may include an embedded hyperlink, accessible, such as by pressing and holding on the text of the regimen, hovering over the regimen using the cursor discussed above, etc. In either case, selection of the information icon or selecting the field may launch a drop down, a hover menu, a web browser or another screen in the application to provide further information about the selected regimen. For example, FIG. 17 includes a drop down 190 providing the user with various options related to a selected regimen ("Rapamycin"), including the ability to access select reference materials, to search one or more databases of information (such as PubMed), and/or to edit one or more fields of the captured document (for example, to correct an error if the physician notices during reading the report that treatments shown correspond to the wrong patient information).

The cohort report may contain all resulting treatment regimens from the subset of similar patients, the treatments that have a statistically significant incidence, or all treatments which meet at least a minimum threshold of patients. Such threshold may be based off a predetermined number of patients, or may be based upon the number of patients in each of a plurality of treatment regimens, such that only regimens which have a certain percentage of the patients of the whole cohort are included, for example, by summing the number of patients in the treatment regimens and only displaying treatments with at least 5% or higher of the total patients. The lower (5%) and upper bounds of this threshold may be determined based off of the number of regimens included in the report and their incidence rate as well. In another example, if several regimens have patients by the tens or hundreds, a regimen with only five patients may be excluded from display. The values may use the average, the mean, the average of the mean, or other calculations to identify where the lower and upper threshold cutoffs should be placed. An exemplary numerical description may quantify the number of patients who received the treatment, the number of patients who responded favorably to the treatment, the number of patients who had no change from the treatment, and/or the number of patients who responded unfavorably to the treatment, identified as "Complete Response (CD), Partial Response (PR), Stable Disease (SD), Progressive Disease (PD)", respectively. In an exemplary visual representation, a color coded graph 186 may be provided to the user to visually represent the same features as the numerical description outlined above. For example, patients who responded favorably may be color coded green and given a distribution of the graphical representation directly proportional to the percentage and patients who responded unfavorably may be color coded red and given a distribution of the graphical representation directly proportional to the percentage.

FIG. 18 is another aspect of the cohort report, with similar layout and information provided as FIG. 17. In FIG. 18, however, the application may provide a therapy response summary conveying adverse event information 194 for each of the regimens 184 identified in FIG. 17. In addition to displaying similar patients' responses to treatment regimens the system may return the incidence of adverse events incurred by similar patients respective to those treatments. These adverse events may be categorized by the type of event (such as neutropenia, nausea, headache, hallucinations, fever, fatigue, depression, cardiac disorders, etc.) and/or by the grade of its severity. (Mild, Moderate, Severe, Life-Threatening, Death). There are thousands of classified adverse events, and the application may be configured to display events based on their respective grade of severity, rather than a name-by-name basis. In another embodiment, the user may select the field of the medication to see the adverse events that contributed to the grade of severity displayed alongside the medication along with the number of incidences and the grade of severity associated with the adverse event.

FIG. 19 is still another aspect of the cohort report which may specialize on clinical trials. Based upon the key health information extracted from the electronic document capture, clinical trials that are available to the patient may be identified and displayed. For each clinical trial, details 198 associated with the name of the clinical trial, geographic location of the facilities administering the trial, treatments associated with the trial, inclusion/exclusion criteria for patients who may participate in the trial, and other relevant information may be included in the report. Additional information may be extracted from the electronic health or medical records associated with the patient when the query is processed that further allow the inclusion and exclusion criteria of a clinical trial to be evaluated. For example, the electronic document capture may be missing key health information pertaining to the patient's medical history, such as medical history relating to whether the patient has taken a drug as part of treatment or has undergone chemotherapy, and the patient's medical history may be referenced to determine eligibility for clinical trial inclusion and exclusion criteria.

Swiping between each report may be performed by pressing the tab associated with the report from the user interface or through gesture controls. For example, a user may swipe the current page to the left or right to swap between respective reports.

The application as described above may be useful in multiple aspects of medical care. For example, the following use cases may be representative of the various ways in which the application may be employed, although it will be understood that the application should not be limited solely to the following use cases.

1: Report Supplementing

Figure 20:
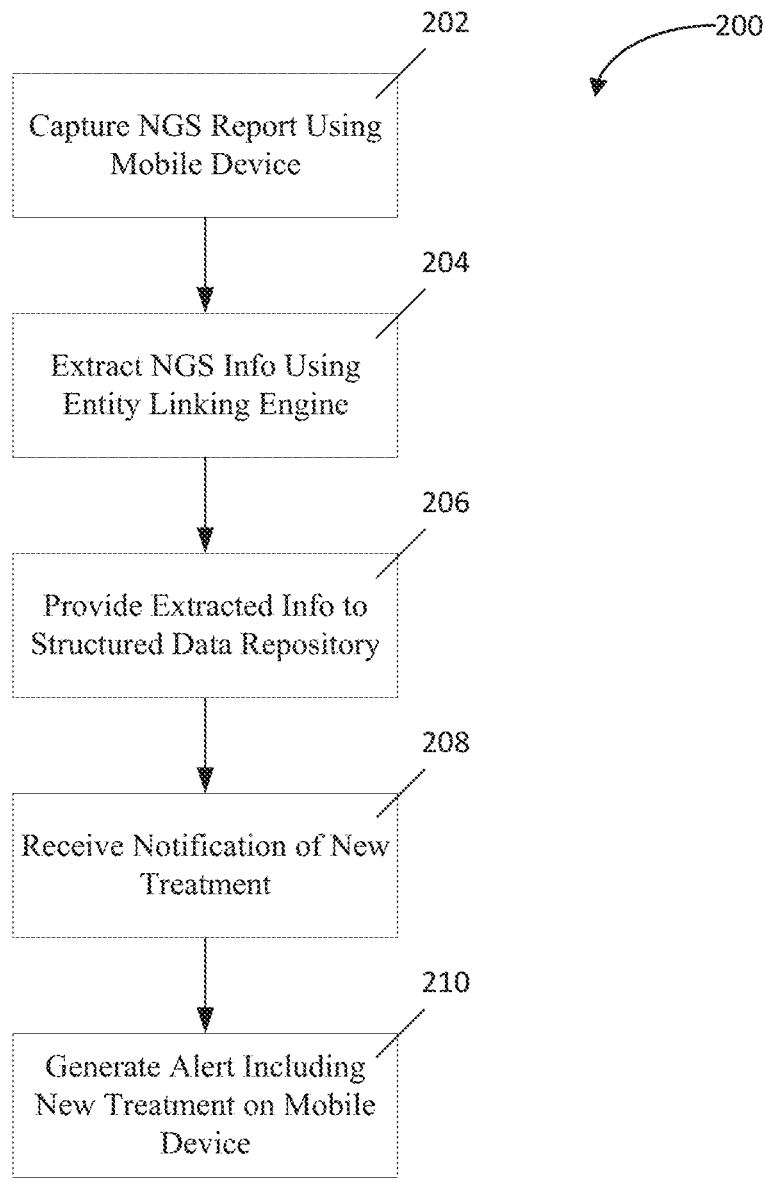
FIG. 20 is a flowchart depicting one implementation of the present disclosure.

Turning to FIG. 20, one method 200 for implementing the present system is depicted. At step 202, the mobile device may be used to capture a document such as a NGS report, the document including medical information such as sequencing information about a patient. At step 204, an entity linking engine may be used to extract at least some of that information, such as using the techniques described above. At step 206, that information then may be provided to one or more data repositories, such as in a structured format.

Information from the electronic document capture may be supplemented in the cohort report with additional supplemented structured data. For example, a genetic sequencing report such as the report of FIG. 4 may identify a genetic mutation that is present in the patient's DNA and may further list treatments available for the genetic mutation. A new treatment may become available after the report is generated but before the physician meets with the patient to discuss the report results. Notification of that treatment may be received, as at step 208. At step 210, the above-described mobile application may supplement the report information and alert the physician to the new treatment for the identified genetic mutation that may have been otherwise overlooked. Additionally, the report may be supplemented by providing access, via hyperlinks or otherwise, to recent articles, publications, or other relevant information that may aid the physician by providing context, background information, or access to recent publications that address details of the report, the other articles, publications, or other relevant information being structured using similar techniques for convenient retrieval. Other medical topics of interest may also be referenced, such as new cell-based therapies (such as immuno, viral, or vector delivery methods) available or new therapies available (such as checkpoint blockades for accelerating immune response, cancer vaccines, etc.). Furthermore, a physician may make treatment decisions and treat the patient according to treatments identified as having a likelihood of success across other patients having similar molecular and clinical features to the patient. Additionally, a physician may identify that a therapy has not had success for the patient and may desire to replace the unsuccessful therapy with one of the report supplemented therapies which is expected to have a likelihood of success. In order to receive preauthorization from or to validate a claim with the patient's insurance (e.g., by indicating the medical necessity of the treatment), the physician may reference the supplementary information, such as the progression free survival rate of similar patients or a publication recently linked on PubMed in their requests to the insurance company. After receiving such pre-authorization or medical necessity indication, the physician then may administer the therapy or other treatment.

2: Training Set Inclusion

Figure 21:
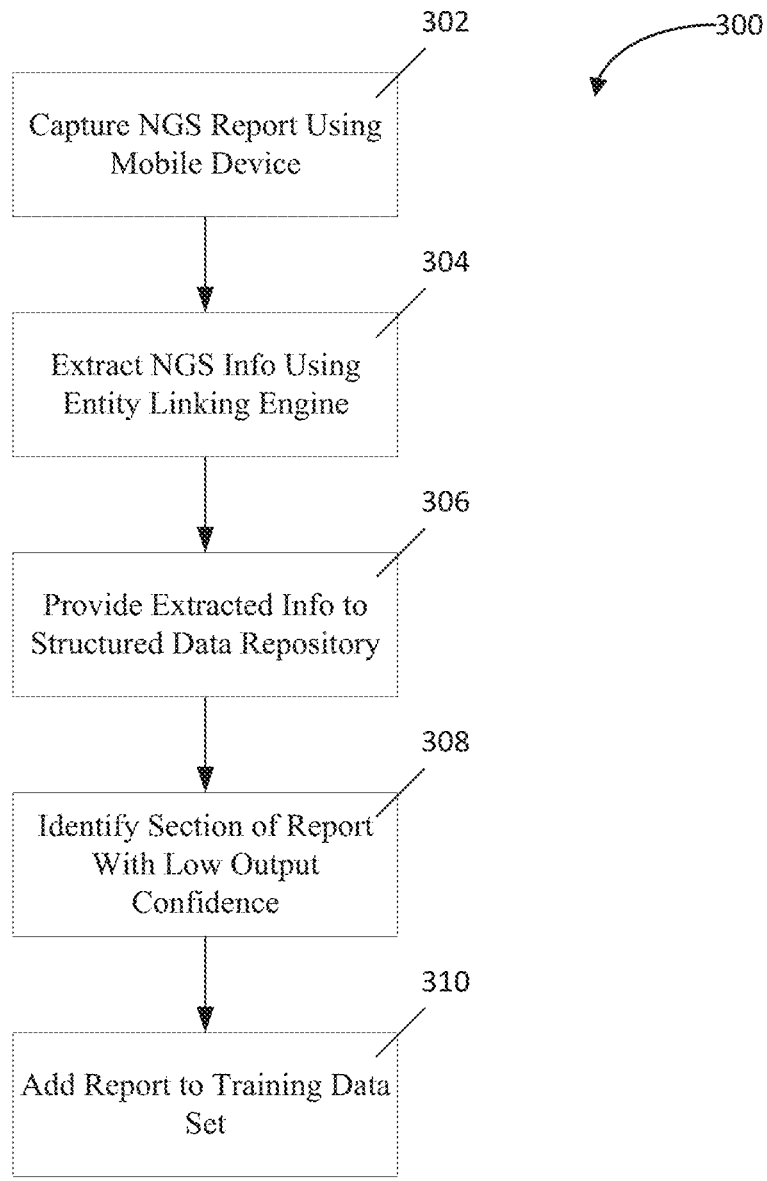
FIG. 21 is a flowchart depicting a second implementation of the present disclosure.

The mobile application described above may also be useful when paired with the existing clinical abstraction training sets for machine learning algorithms driving the abstraction process. Thus, turning to FIG. 21, another method 300 for implementing the present system is depicted. At step 302, the mobile device may be used to capture a document such as a NGS report, the document including medical information such as sequencing information about a patient. At step 304, an entity linking engine may be used to extract at least some of that information, such as using the techniques described above. At step 306, that information then may be provided to one or more data repositories, such as in a structured format. At step 308, an active learning element of the machine learning engine may identify a section of the electronic document capture for which the algorithm did not have a high confidence of the predicted output. The electronic document capture may then be labeled as a training input and added to a respective training data set, as at step 310. The improved training set may then be used to train a machine learning algorithm to generate improved results. Many document types (such as genetic sequencing reports) include relevant attributes such as genes, variants, etc., that would normally be abstracted physically by hand may then be automatically extracted according to these characteristics and paired with additional clinical and phenotypic characteristics (such as demographics, diagnosis, assessments, labs, etc.).

3: Database Comprehension Validation

Figure 22:
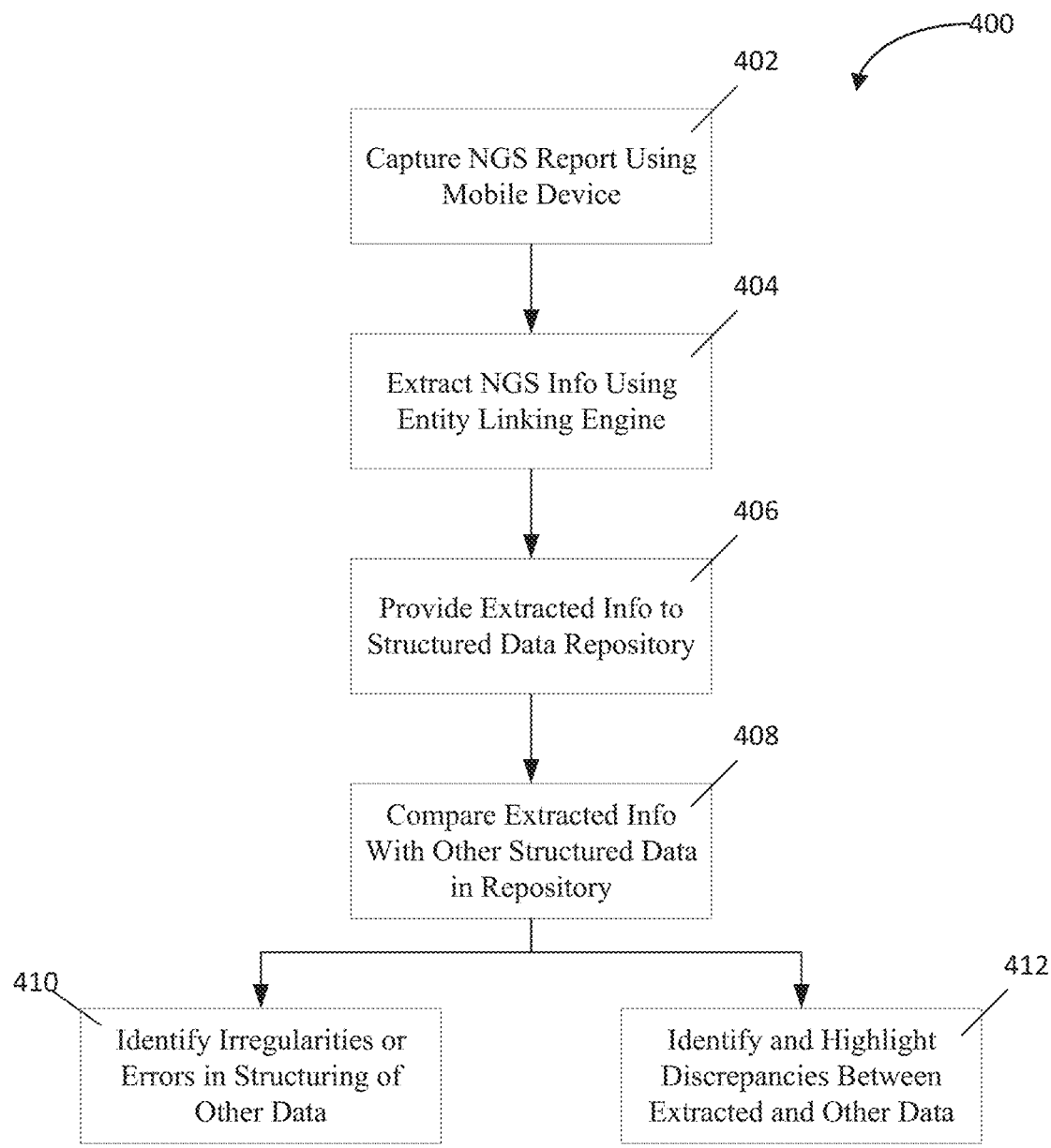
FIG. 22 is a flowchart depicting a third implementation of the present disclosure.

Turning to FIG. 22, another method 400 for implementing the present system is depicted. At step 402, the mobile device may be used to capture a document such as a NGS report, the document including medical information such as sequencing information about a patient. At step 404, an entity linking engine may be used to extract at least some of that information, such as using the techniques described above. At step 406, that information then may be provided to one or more data repositories, such as in a structured format. Further, the disclosure may also aid in the ability to fully assess the quality of a given structured clinical record by comparing extracted information against other structured data, as at step 408. For instance, the mobile application may indicate the presence (or absence) of various molecular biomarkers (such as TP53) that indicate whether other various and/or observed clinical attributes are appropriate. For example, molecular biomarkers like KRAS may be present in only a certain subset of cancer types (such as pancreatic cancer). This capability can improve data integrity by identifying unusual and/or incorrect structured clinical data that may have been abstracted and/or ingested directly from third parties via various integration mechanisms, as at step 410, and by identifying and highlighting discrepancies between the extracted data and other relevant data in the system separate from that extracted data, as at step 412.

4: Radiology Report Supplementing

Figure 23:
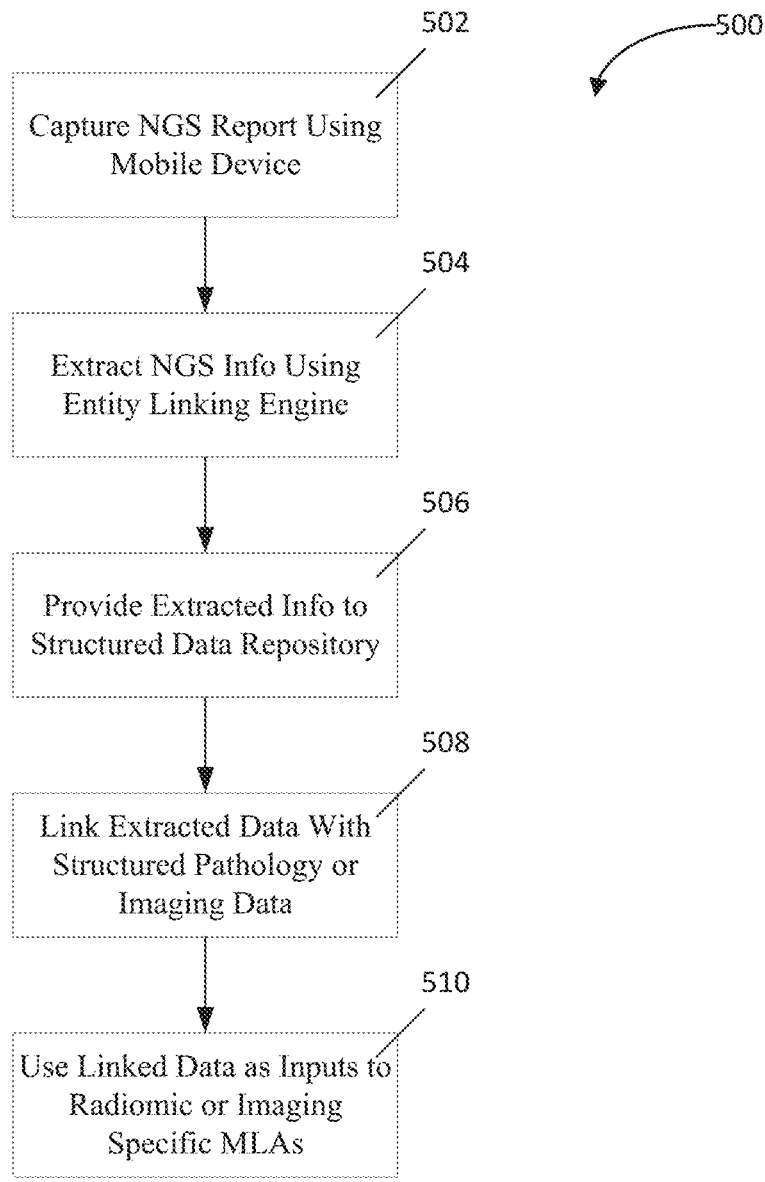
FIG. 23 is a flowchart depicting a fourth implementation of the present disclosure.

Turning to FIG. 23, still another method 500 for implementing the present system is depicted. At step 502, the mobile device may be used to capture a document such as a NGS report, the document including medical information such as sequencing information about a patient. At step 504, an entity linking engine may be used to extract at least some of that information, such as using the techniques described above. At step 506, that information then may be provided to one or more data repositories, such as in a structured format. The extracted data then may also be useful when attempting to determine and/or unite clinical and/or phenotypic attributes with observations from pathological and/or radiological imagery, such that the system may link the extracted data, via its structuring, with structured clinical patient data received from pathology reports, imaging features, and/or other imaging sources, as at step 508. Often, the ability to obtain more context about a given patient and/or diagnosis is crucial in determining whether imaging is of a sufficient quality for computing radiomic attributes (such as surface area, volume, etc.) as part of contouring efforts. Further, clinical attributes obtained via the disclosure can help to unify disparate sources of data (such as molecular characteristics found on a genetic sequencing report, structured clinical data obtained from pathology reports, imaging features and characteristics extracted from imaging). As a result, radiomic and imaging specific machine learning algorithms can become more robust through the availability of this additional data, such as by using the data linked in step 508 as inputs to those algorithms at step 510. Furthermore, the imaging itself may or may not come with diagnosis and/or phenotypic attributes included so the linkage between the imaging data and the related information that can be extracted from source documents via the invention can help resolve gaps in data.

5: Knowledge Database Curation and Additions

Figure 24:
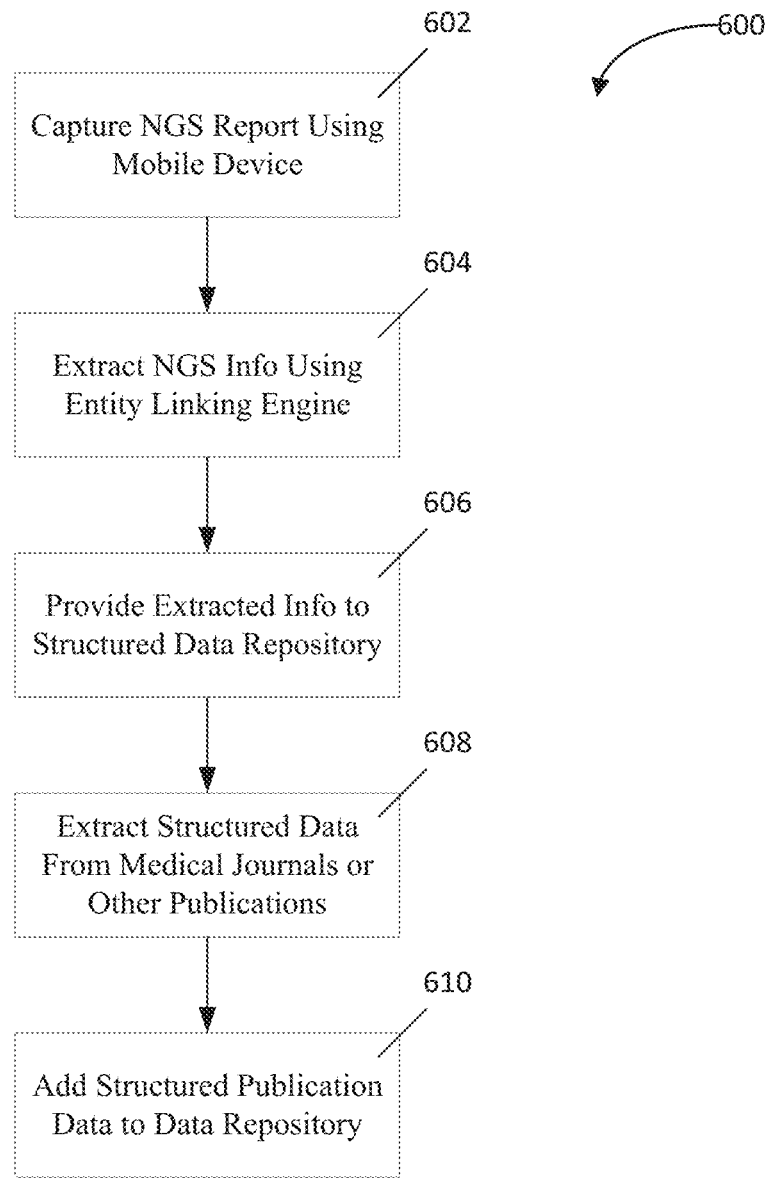
FIG. 24 is a flowchart depicting a fifth implementation of the present disclosure.

Turning to FIG. 24, yet another method 600 for implementing the present system is depicted. At step 602, the mobile device may be used to capture a document such as a NGS report, the document including medical information such as sequencing information about a patient. At step 604, an entity linking engine may be used to extract at least some of that information, such as using the techniques described above. At step 606, that information then may be provided to one or more data repositories, such as in a structured format. In addition to this patient-specific data, the system also may process journal articles from medical publications by similarly extracting structured medical information from those sources at step 608 and then adding that structured information to the data repository at step 610 to curate a knowledge database based upon features of each report which are relevant to each database specialization. For example, a knowledge database for cancer treatments may desire to receive new articles which are relevant by filtering newly published articles to find articles which are oncology and treatment focused which may be added into the knowledge database along with key words, phrases, and other indexable features. The new entry may then be reviewed for curation or automatically entered into the knowledge database.

6: Facility-Based Records Sync for Facilities that do not Easily Share Data

Figure 25:
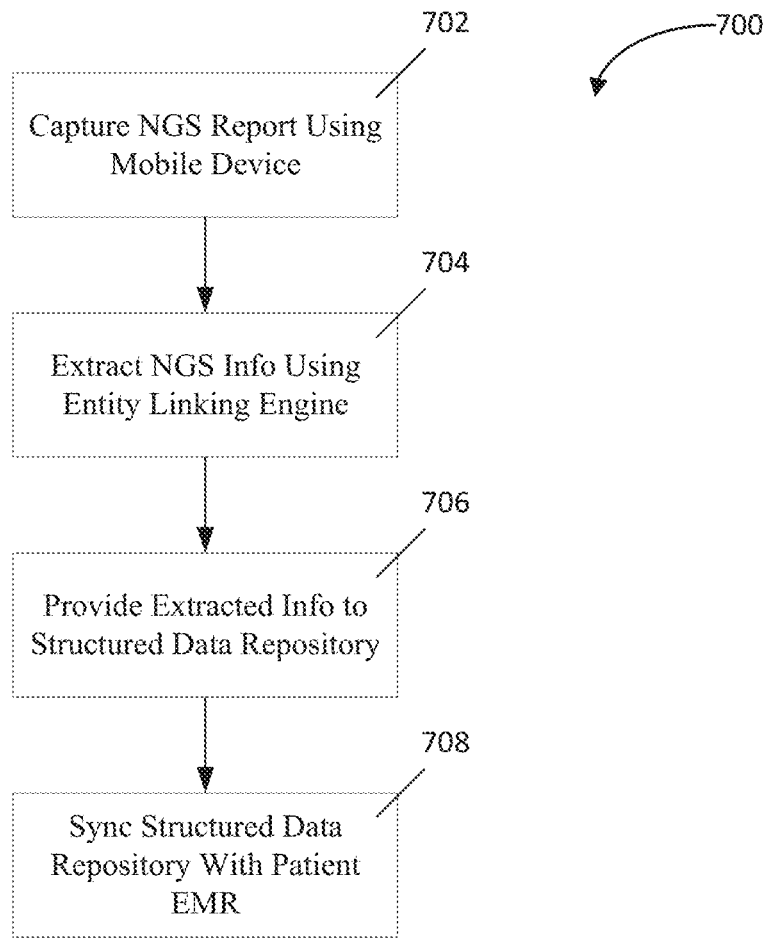
FIG. 25 is a flowchart depicting a sixth implementation of the present disclosure.

The disclosure above may also serve as a means to easily integrate EMR systems which are not synced. For example, turning to FIG. 25, yet another method 700 for implementing the present system is depicted. At step 702, the mobile device may be used to capture a document such as a NGS report, the document including medical information such as sequencing information about a patient. At step 704, an entity linking engine may be used to extract at least some of that information, such as using the techniques described above. At step 706, that information then may be provided to one or more data repositories, such as in a structured format. A patient receiving treatment at an institution which is geographically distance from their home may desire to report to a local institution for testing and lab results. The local institution may not sync their EMR with the primary institution and only provide a document with the testing or lab reports to the primary institution. The instant disclosure may allow the primary institution to sync the report with their EMR by quickly scanning the report once received, as at step 708.

7. Adding to De-Identified Data Sets

Figure 26:
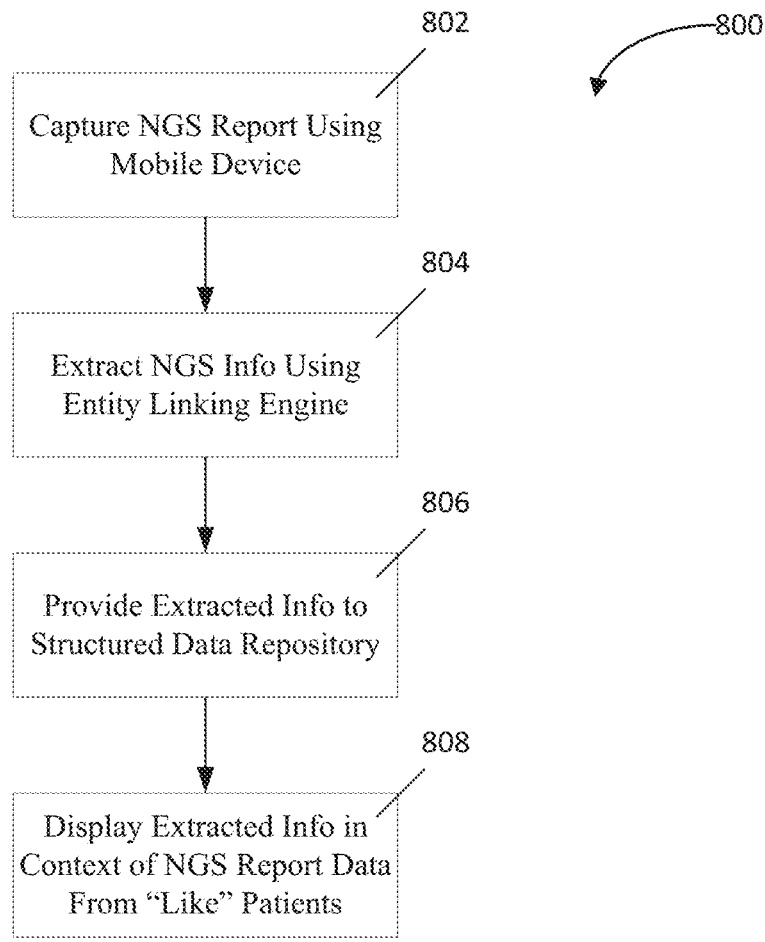
FIG. 26 is a flowchart depicting a seventh implementation of the present disclosure.

A physician may wish to take the information provided on a lab report and ingest it into a data platform that is unconnected from the provider of the lab report. Thus, turning to FIG. 26, yet another method 800 for implementing the present system is depicted. At step 802, the mobile device may be used to capture a document such as a NGS report, the document including medical information such as sequencing information about a patient. At step 804, an entity linking engine may be used to extract at least some of that information, such as using the techniques described above. At step 806, that information then may be provided to one or more data repositories, such as in a structured format. At step 808, the data platform may allow the physician to view the patient information from the report in the context of a larger data set of "like" patients, whom may have received NGS from different clinical laboratories.

8. Tumor Board

Figure 27:
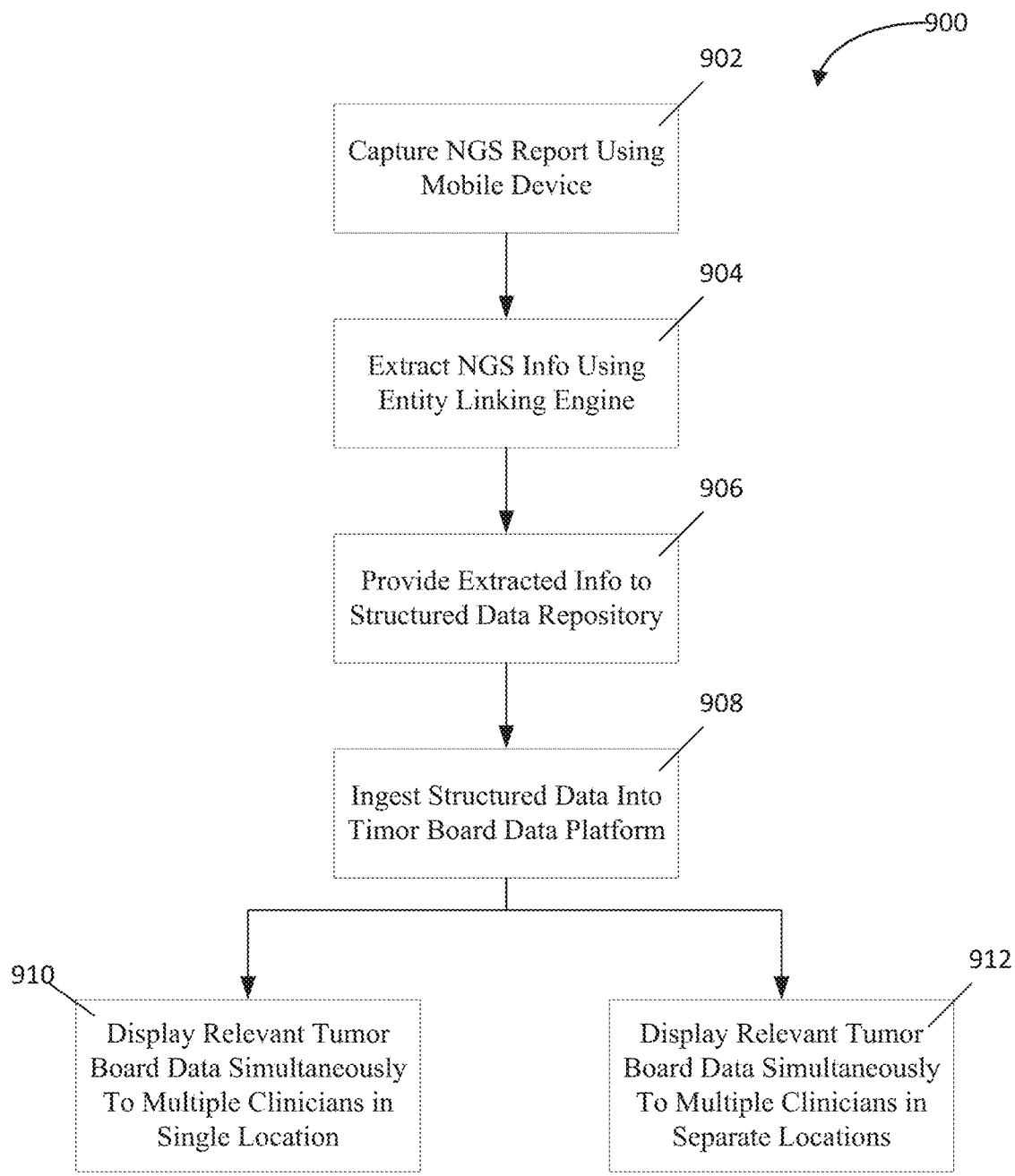
FIG. 27 is a flowchart depicting an eighth implementation of the present disclosure.

Turning to FIG. 27, yet another method 900 for implementing the present system is depicted. At step 902, the mobile device may be used to capture a document such as a NGS report, the document including medical information such as sequencing information about a patient. At step 904, an entity linking engine may be used to extract at least some of that information, such as using the techniques described above. At step 906, that information then may be provided to one or more data repositories, such as in a structured format. At that point, a physician may wish to take the information provided on a lab report and ingest it into a data platform that provides tumor board functionality to the physician, as at step 908. An exemplary tumor board platform may provide functionality to permit physicians to review the cases of multiple patients, one at a time, and review patient characteristics (such as age, molecular profile, clinical profile, gender, race, and so forth) to determine the most appropriate treatment for the patient. The tumor board platform may permit multiple clinicians to sit in a single location, such as a room, and view the clinical information about each patient, as at step 910. Or, the platform may be virtual, allowing multiple clinicians to sit in disparate locations while simultaneously reviewing a patient's information, as at step 912.

9. Alternative Clinical Decision Support

Figure 28:
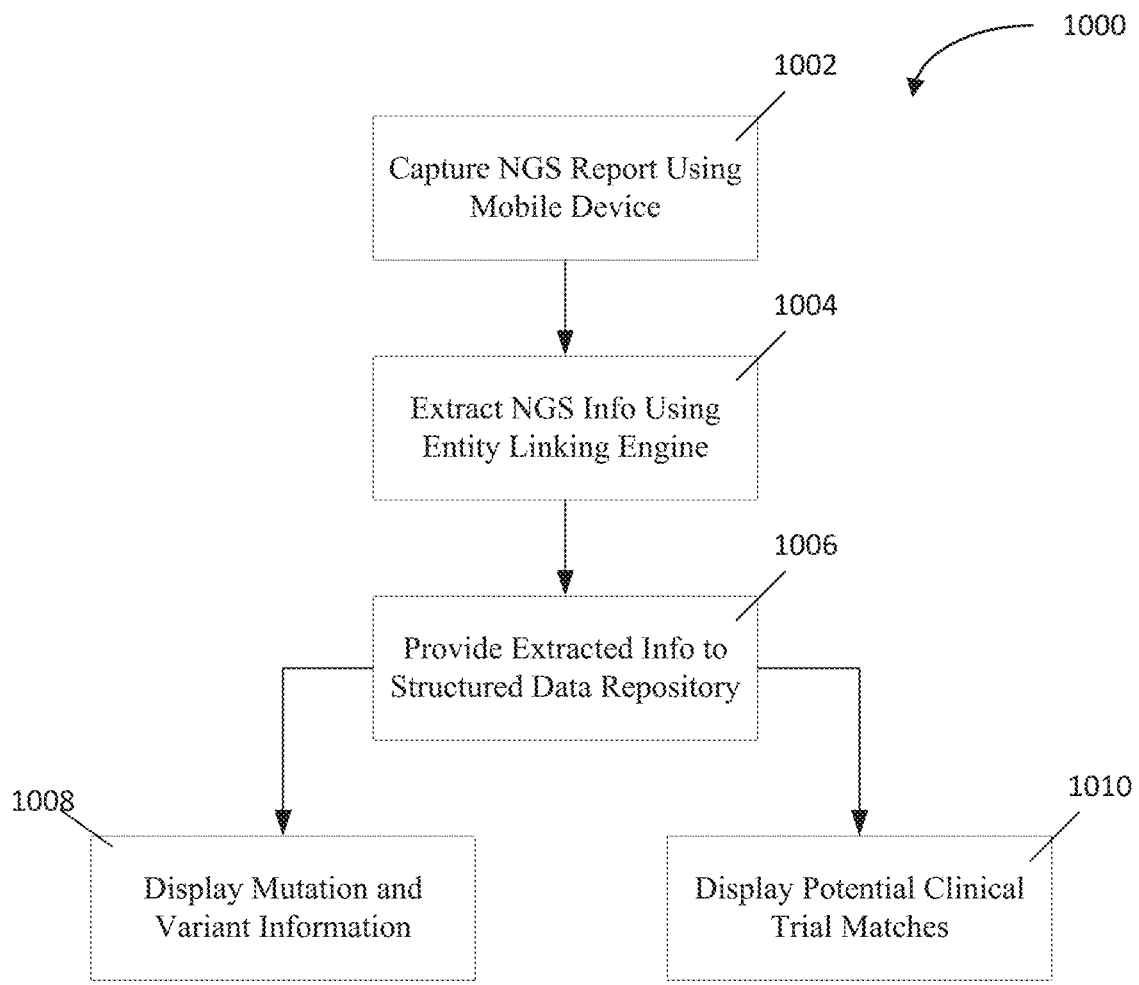
FIG. 28 is a flowchart depicting a ninth implementation of the present disclosure.

Different clinical laboratories use different bioinformatics platforms, and calling a variant on a gene does not necessarily mean that a clinical laboratory will suggest the same treatment as another clinical lab that calls the same variant. Thus, turning to FIG. 28, still another method 1000 for implementing the present system is depicted. At step 1002, the mobile device may be used to capture a document such as a NGS report, the document including medical information such as sequencing information about a patient, as well as one or more of a type of treatment, dosage of treatment, duration of treatment, immunology markers, potential clinical trial(s) available to the patient, etc. Exemplary immunology markers include, but are not limited to, PD-1 expression, other checkpoint inhibitor indicators (such as CTLA-4), immune cell infiltration, immunohistochemistry (IHC) indicators, tumor infiltrating lymphocyte indicators, monoclonal antibody indicators, vaccine/adjuvant indicators such as tumor cell vaccines, antigen vaccines, dendritic cell vaccines, vector-based vaccines, oncolytic viruses, CAR T-cell therapy, etc. At step 1004, an entity linking engine may be used to extract at least some of that information, such as using the techniques described above. At step 1006, that information then may be provided to one or more data repositories, such as in a structured format, the data repositories including the relevant types of treatment, dosages of treatment, durations of treatment, immunology markers, potential clinical trial(s) available to the patient, etc., for patients with similar sequencing information, where the information presented in the NGS report may be different from the relevant counterparts stored in the data repositories. At step 1008, the system may display a subset of the extracted data, such as the patient's identified mutations and variants. By permitting capture of clinical variants, a physician may be able to get a "second opinion" on the type of treatment, dosage of treatment, duration of treatment, immunology markers, and so forth. Likewise, at step 1010, the system may display one or more clinical trials potentially available to the patient, as discussed above. In this manner, by comparing and displaying the reported information against their potentially available counterparts, the physician may get a "second opinion" on clinical trials that may be appropriate for the patient.

Figure 29:
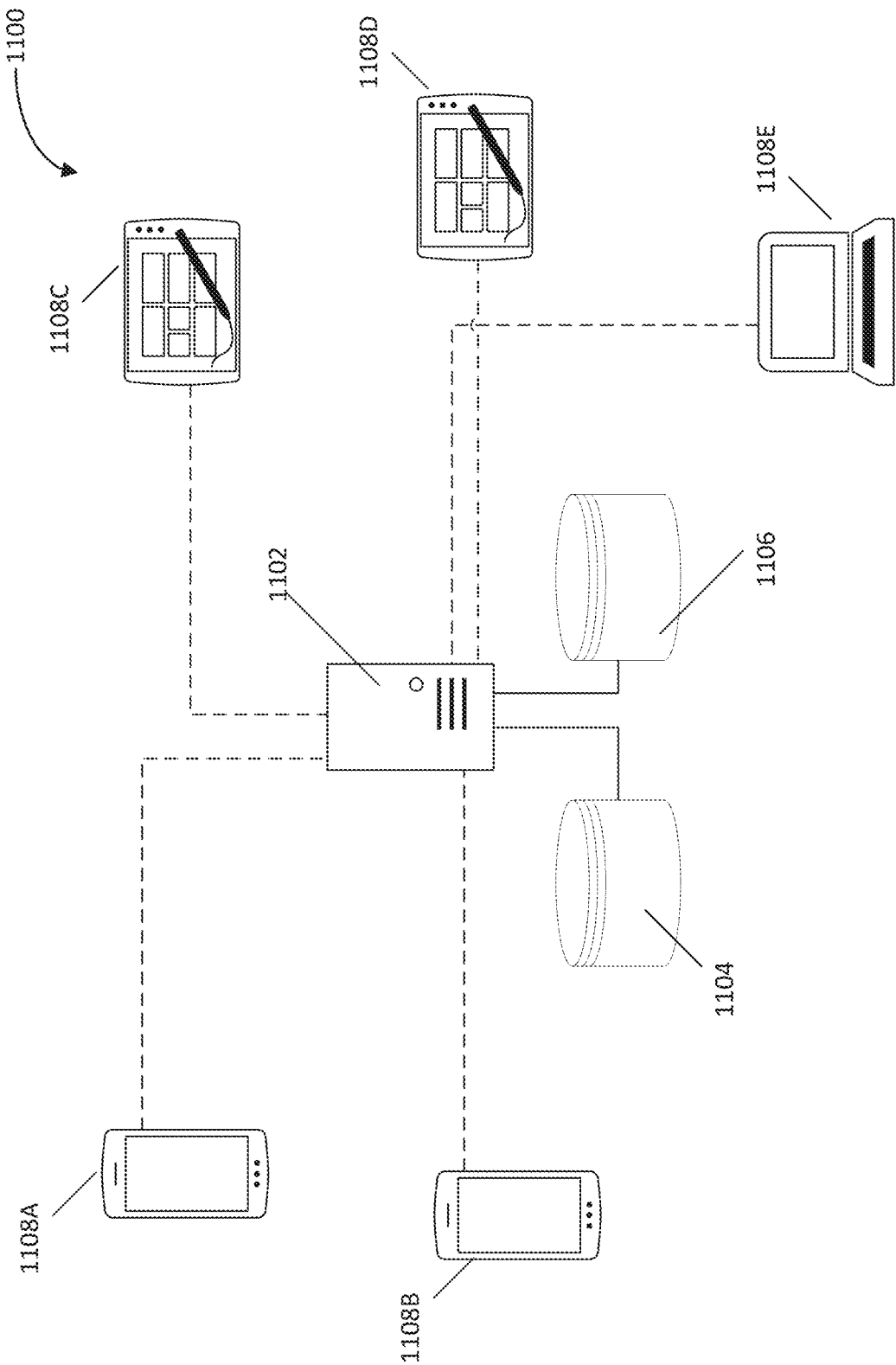
FIG. 29 is an exemplary system diagram for carrying out the methods described herein.

As seen in FIG. 29, a system 1100 may include a server 1102 including or in communication with a first database 1102 and a second database 1104. In one aspect, the first database 1102 may include patient-specific information, such as elements of each patient's EHR or EMR data. The second database 1104 may be a knowledge-database that includes patient-agnostic medical information, such as genetic variants and their related mutation effects for observed and classified variants for each gene, medications or other treatments relevant to the genetic variants, articles relevant to those variants, etc. The second database 1104 further may include mask or template-based information to enable the system to more efficiently extract information from one or more template-style documents. It will be appreciated that the first and second databases may be combined into a single database or, alternatively, that one or both of those databases individually may actually be a plurality of different databases, such as to assist in data segregation or improved processing by optimizing database calls for the requested different types of data.

Staying with FIG. 29 the server 1102 may be in communication with one or more mobile devices, such as smartphones 1108A, 1108B, tablet devices 1108C, 1108D, and laptop or other computing devices 1108E. In one aspect, the server 1102 may be connected directly to one or more of the devices, such as via an Ethernet or other suitable connection. Alternatively, the server 1102 may be connected wirelessly to one or more of the devices, such as via WiFi or another wireless connection, as would be appreciated by those of ordinary skill in the relevant art. As discussed herein, one or more analytical actions described herein may be performed by the mobile devices. Additionally or alternatively, one or more actions may be performed by the server, such as the mobile devices may be used to create new patient records and capture electronic images of documents relating to patients, while the server may be employed to perform the OCR and/or other analytics described above on the captured documents.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

The invention claimed is:

1. A method for providing a physician with clinical decision support information about a patient whose DNA has been sequenced with a next generation sequencing (NGS) system, comprising:
  receiving, from a mobile device, an image of a medical document comprising NGS medical information of the patient;
  extracting a first region from the image;
  extracting NGS medical information of the patient from the first region into a structured dataset, the extracted NGS medical information including at least one gene identifier;
  correlating a portion of the extracted NGS medical information that includes the at least one gene identifier with summarized medical information from a cohort of patients similar to the patient; and
  generating, for display on the mobile device, a clinical decision support report comprising the summarized medical information.

2. The method of claim 1, wherein extracting the first region from the image is based at least in part from a template of a predefined model matched to the image, wherein the template encodes one or more rules.

3. The method of claim 2, wherein the one or more rules comprise applying one or more masks to identify the first region.

4. The method of claim 2, wherein the one or more rules are directed to document extraction features and comprise: a first rule for regular expressions; a second rule for natural language processing; and a third rule for column-row pairing to text identified in the one or more regions.

5. The method of claim 2, wherein the one or more rules are directed to document format features and comprise one or more rules for validating the extracted NGS medical information based at least in part from a second region extracted from the medical document, wherein the second region is distinct from the first region.

6. The method of claim 1, wherein the summarized medical information comprises treatment incidence information.

7. The method of claim 1, wherein the summarized medical information comprises treatment response information.

8. The method of claim 1, wherein correlating a portion of the extracted NGS medical information with summarized medical information from a cohort of patients similar to the patient comprises:
  selecting a gene identifier in the extracted NGS medical information;
  querying a structured data repository of medical information for patients with a gene identifier that is the same as the selected gene identifier;
  assembling the cohort of patients similar to the patient from the results of the query.

9. The method of claim 1, wherein the summarized medical information comprises clinical decision support information not found in the medical document.

10. The method of claim 7, wherein the treatment response information comprises a treatment and a clinical response level of the cohort of patients prescribed the treatment.

11. The method of claim 1, wherein the summarized medical information comprises a treatment name, the method further comprising:
  providing the treatment name to an insurer of the patient; and receiving a pre-authorization for the treatment from the insurer.

12. The method of claim 1, wherein extracting NGS medical information from the first region further comprises:
identifying a first type of NGS medical information from a template;
identifying a first extraction rule for extracting the first type of NGS medical information from the template;
extracting the first type of NGS medical information from the first region based at least in part on the first extraction rule; and
classifying the extracted first type of NGS medical information.

13. The method of claim 12, wherein extracting the NGS medical information based at least in part on the first extraction rule further comprises:
determining a first concept from the NGS medical information; and
identifying a match to the first concept in a first list of concepts.

14. The method of claim 13, further comprising:
identifying a first classification from the template;
generating a comparison of a classification of the first concept to the first classification; and
storing the match to the first concept as the extracted first type of NGS medical information based on a positive generated comparison.

15. The method of claim 14, wherein classifying the extracted first type of NGS medical information further comprises:
identifying an additional NGS medical information in the first region;
extracting the additional NGS medical information; and
generating structured data from the extracted first type of NGS medical information and the extracted additional NGS medical information.

16. The method of claim 14, wherein identifying a first classification from the template further comprises selecting the first classification from an enumerated list of classifications within the template.

17. The method of claim 12, wherein extracting the first type of NGS medical information from the first region further comprises:
extracting the first type of NGS medical information from a second region of the medical document;
validating the extracted first type of NGS medical information from the second region with a verified set of NGS medical information previously extracted from the second region; and
validating the extracted first type of NGS medical information from the first region with the validated extracted first type of NGS medical information from the second region.

18. The method of claim 12, wherein extracting the first type of NGS medical information from the first region further comprises:
determining a first concept from the NGS medical information;
identifying a plurality of matches to the first concept in a first list of concepts;
identifying a first classification from the template;
generating, for each match of the plurality of matches, a comparison of a classification of the first concept to the first classification; and
storing a first match to the first concept, of the plurality of matches, as the extracted first type of NGS medical information based on a positive generated comparison.

19. The method of claim 12, wherein extracting the first type of NGS medical information from the first region further comprises:
determining a first concept from the NGS medical information;
identifying a plurality of matches to the first concept in a first list of concepts;
identifying a first classification from the template;
generating, for each match of the plurality of matches, a classification of the match;
generating, for each match of the plurality of matches, an estimated confidence reliability rating of the match; and
storing the match with the highest estimated confidence, of the plurality of matches, as the extracted first type of NGS medical information.

20. The method of claim 12, wherein extracting the NGS medical information of the patient from the first region further comprises:
determining a first concept from the NGS medical information;
identifying a match to the first concept in a first list of concepts, wherein the first list of concepts is not a preferred authority;
referencing the first concept to an entity in a database of related concepts; and
identifying a match to a second concept in a second list of concepts, the second list of concepts not directly linked to the first list of concepts except by a relationship between the entity and the first concept and the entity and the second concept, wherein the second list of concepts is a preferred authority.

21. The method of claim 20, further comprising:
identifying a first classification from the template;
generating a comparison of a classification of the match to the second concept to the first classification; and
storing the match to the second concept as the extracted first type of NGS medical information based on a positive generated comparison.

22. The method of claim 20, wherein generating structured data from the extracted NGS medical information further comprises:
identifying a structured format from the template, the structured format including a plurality of fields;
assigning one or more values associated with the second concept to one or more of the plurality of fields;
identifying one or more values from the first region;
assigning one or more of the identified one or more values to one or more others of the plurality of fields; and
storing the structured format having the assigned one or more values and the assigned one or more of the identified values as the structured data.

23. The method of claim 20, further comprising:
retrieving a predetermined degree of specificity, the predetermined degree of specificity identifying selection criteria;
identifying a degree of specificity of the second concept;
evaluating the degree of specificity of the second concept with the selection criteria of the predetermined degree of specificity;
normalizing the second concept within the preferred authority to a third concept satisfying the selection criteria of the predetermined degree of specificity; and
storing the third concept as the extracted first type of NGS medical information.

24. The method of claim 23, wherein generating structured data from the extracted NGS medical information further comprises:

identifying a structured format from the template, the structured format including a plurality of fields;
assigning one or more values associated with the third concept to one or more of the plurality of fields;
identifying one or more values from the first region;
assigning one or more of the identified values to one or more others of the plurality of fields; and
providing the structured format having the one or more assigned values and the assigned one or more of the identified values as the structured data.

25. The method of claim 20, wherein the first concept is extracted from sentences of text using natural language processing.

26. The method of claim 20, wherein the first concept comprises at least one of medications, treatments, or NGS medical information of the patient.

27. The method of claim 1, wherein the summarized medical information is generated from a method comprising:
deriving a plurality of first concepts from a publication, the publication separate from the medical document;
normalizing each concept in the plurality of first concepts; and
generating a knowledge database comprising each of the normalized concepts.

28. The method of claim 27, further comprising:
generating links in the knowledge database between the publication and each instance of its respective normalized concepts;
identifying one or more normalized concepts within the structured data matching one or more normalized concepts linked to the publication; and
providing the links in the knowledge database to the identified normalized concepts in the summarized medical information.

29. The method of claim 12, wherein extracting the first type of NGS medical information further comprises:
generating edited NGS medical information from the NGS medical information;
providing the NGS medical information and the edited NGS medical information to an abstraction engine to retrain the abstraction engine to extract the edited NGS medical information from the first region using a second extraction rule; and
replacing the first extraction rule of the first type of NGS medical information in the template with the second extraction rule.

* * * * *

UNITED STATES PATENT AND TRADEMARK OFFICE
CERTIFICATE OF CORRECTION

PATENT NO. : 10,902,952 B2
APPLICATION NO. : 16/531005
DATED : January 26, 2021
INVENTOR(S) : Michael Ryan Lucas et al.

Page 1 of 1

It is certified that error appears in the above-identified patent and that said Letters Patent is hereby corrected as shown below:

In the Specification

Column 18, Line 50, "CARDS" should be --CARD8--.

Column 19, Line 12, "CPLD" should be --CYLD--.

Column 20, Line 10, "KATE" should be --KAT8--.

Column 21, Line 55, "STATE" should be --STAT6--.

Column 41, Line 20, "GUI's" should be --CUI's--.

Column 44, Line 64, "EMIR/EHR" should be --EMR/EHR--.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*